United States Patent
Scherrer et al.

(10) Patent No.: US 12,084,422 B2
(45) Date of Patent: Sep. 10, 2024

(54) PHENYL-N-QUINOLINE DERIVATIVES FOR TREATING A RNA VIRUS INFECTION

(71) Applicants: ABIVAX, Paris (FR); CENTRE NATIONAL DE LA RECHERCHE SCIENTIFIQUE, Paris (FR); UNIVERSITE DE MONTPELLIER, Montpellier (FR); INSTITUT CURIE, Paris (FR)

(72) Inventors: Didier Scherrer, Castelnau-le-Lez (FR); Jamal Tazi, Clapiers (FR); Florence Mahuteau-Betzer, Saint Remy-les-Chevreuse (FR); Romain Najman, L'Hay-les'Roses (FR); Julien Santo, Grabels (FR); Cécile Apolit, Grabels (FR)

(73) Assignees: ABIVAX, Paris (FR); CENTRE NATIONAL DE LA RECHERCHE SCIENTIFIQUE;, Paris (FR); UNIVERSITE DE MONTPELLIER, Montpellier (FR); INSTITUT CURIE, Paris (FR)

(*) Notice: Subject to any disclaimer, the term of this patent is extended or adjusted under 35 U.S.C. 154(b) by 667 days.

(21) Appl. No.: 17/259,364

(22) PCT Filed: Jul. 9, 2019

(86) PCT No.: PCT/EP2019/068459
§ 371 (c)(1),
(2) Date: Jan. 11, 2021

(87) PCT Pub. No.: WO2020/011810
PCT Pub. Date: Jan. 16, 2020

(65) Prior Publication Data
US 2021/0309611 A1    Oct. 7, 2021

(30) Foreign Application Priority Data
Jul. 9, 2018  (EP) ..................... 18305910

(51) Int. Cl.
*C07D 215/38*  (2006.01)
*A61P 31/14*   (2006.01)
(Continued)

(52) U.S. Cl.
CPC ............ *C07D 215/38* (2013.01); *A61P 31/14* (2018.01); *C07D 401/12* (2013.01); *C07D 405/12* (2013.01)

(58) Field of Classification Search
CPC ............... C07D 215/38; A61P 31/14
See application file for complete search history.

(56) References Cited

U.S. PATENT DOCUMENTS 9,827,237 B2 * 11/2017 Tazi ................... A61P 21/00
10,718,770 B2 * 7/2020 Scherrer ........... G01N 33/56983
(Continued)

FOREIGN PATENT DOCUMENTS

CN        101142208 A    3/2008
RU        2379302 C2     1/2010
(Continued)

OTHER PUBLICATIONS

Scherreret al (2016): STN International, CAPLUS database, Accession No. 2016: 1435309.*
Tazi et al (2015): STN International, CAPLUS database, Accession No. 2015: 34989.*
Aug. 20, 2020 Search Report Issued in International Patent Application No. PCT/EP2020/070294.
U.S. Appl. No. 17/628,402, filed Jan. 19, 2022 in the name of Scherrer et al.
Oct. 7, 2019 Search Report Issued in International Patent Application No. PCT/EP2019/068465.
Schmidt et al.; "Transition metals in Organic Synthesis, Part 91: Palladium-catalyzed Approach to 2, 6-Dioxygenated Carbazole Alkaloids—First Total Synthesis of the Phytoalexin Carbalexin C"; Synlett; 2009; pp. 2,421-2,424.
(Continued)

*Primary Examiner* — Golam M Shameem
(74) *Attorney, Agent, or Firm* — Oliff PLC

(57) ABSTRACT

A compound of formula (I) or any of its pharmaceutically acceptable salt for use in the treatment and/or prevention of a RNA virus infection, and a RNA virus infection from group IV or V of the Baltimore classification

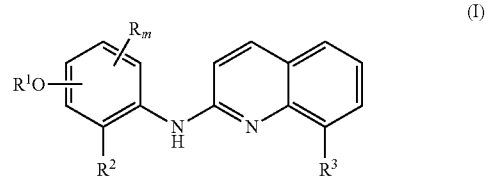

(I)

wherein $R^3$ represents a chlorine atom or a hydrogen atom, R represents a $(C_1-C_4)$alkyl group, a $(C_3-C_6)$cycloalkyl group, a halogen atom, a $(C_1-C_5)$alkoxy group, a $—SO_2—NR_aR_b$ group, a $—SO_3H$ group, a $—OH$ group, a $—O—SO_2—OR_c$ group or a $—O—P(=O)—(OR_c)(OR_d)$ group, $R^1$ represents (i) a $CF_3$ group, (ii) a $(C_1-C_{10})$alkyl group, (iii) a $(C_3-C_6)$cycloalkyl or a $(C_3-C_6)$heterocycloalkyl group or (iv) a phenyl group or a naphthyl group, and $R^2$ represents a hydrogen atom, a $(C_1-C_{10})$alkyl group, a $(C_3-C_6)$cycloalkyl or a $(C_3-C_6)$heterocycloalkyl group and further relates to new compounds, to pharmaceutical compositions containing them and to synthesis process for manufacturing them.

12 Claims, No Drawings

(51) Int. Cl.
C07D 401/12 (2006.01)
C07D 405/12 (2006.01)

(56) References Cited

U.S. PATENT DOCUMENTS

| | | |
|---|---|---|
| 2005/0154232 A1 | 7/2005 | Lardy et al. |
| 2007/0197625 A1 | 8/2007 | Casara et al. |
| 2014/0187641 A1 | 7/2014 | Dalton et al. |
| 2016/0031797 A1 | 2/2016 | Dalton et al. |

FOREIGN PATENT DOCUMENTS

| | | |
|---|---|---|
| RU | 2008129807 A | 2/2010 |
| RU | 2467007 C2 | 11/2012 |
| RU | 2628800 C2 | 8/2017 |
| WO | 2003/033467 A1 | 4/2003 |
| WO | 2004/084901 A1 | 10/2004 |
| WO | 2005/021544 A2 | 3/2005 |
| WO | 2005/023255 A2 | 3/2005 |
| WO | 2005058869 A1 | 6/2005 |
| WO | 2006/037117 A1 | 4/2006 |
| WO | 2006/097534 A1 | 9/2006 |
| WO | 2007/081517 A2 | 7/2007 |
| WO | 2007/135106 A1 | 11/2007 |
| WO | 2009/087238 A2 | 7/2009 |
| WO | 2010/143168 A2 | 12/2010 |
| WO | 2011/163355 A1 | 12/2011 |
| WO | 2012/080953 A1 | 6/2012 |
| WO | 2012/131656 A2 | 10/2012 |
| WO | 2014/164667 A1 | 10/2014 |
| WO | 2015/001518 A1 | 1/2015 |
| WO | 2016/135053 A1 | 9/2016 |
| WO | 2016/135055 A1 | 9/2016 |
| WO | 2017/158201 A1 | 9/2017 |

OTHER PUBLICATIONS

Sep. 10, 2019 Search Report Issued in International Patent Application No. PCT/EP2019/068460.
Sep. 27, 2019 Search Report Issued in International Patent Application No. PCT/EP2019/068461.
Sep. 26, 2019 Search Report Issued in International Patent Application No. PCT/EP2019/068459.
U.S. Appl. No. 17/259,483, filed Jan. 11, 2021 in the name of Scherrer et al.
U.S. Appl. No. 17/259,370, filed Jan. 11, 2021 in the name of Scherrer et al.
U.S. Appl. No. 17/259,451, filed Jan. 11, 2021 in the name of Scherrer et al.
Berman Group IV viruses: Single-Stranded (+)Sense RNA; Chapter 42; pp. 237-246; 2012.
Berman Group V viruses: Single-Stranded (−)Sense RNA; Chapter 43; pp. 247-255; 2012.
R.I. Hernandez-Benitez et al, "Palladium-Catalyzed Synthesis of Diarylamines and 1- and 2-Oxy-genated Carbazoles: Total Syntheses of Natural Alkaloids Clauraila A, Clausenal, Clausine P, and 7-Methoxy-O-methylmukonal", Synthesis, Jul. 5, 2017, 49, A-O.
Suzuki et al, "Design, Synthesis, and Biological Activity of a Novel Series of Human Sirtuin-2-Selective Inhibitors", Journal of Medicinal Chemistry, pp. A-N, Jan. 26, 2012.
Bianchi et al, "Compounds with antiulcer and antisecretory activity", Eur. J. Med. Chem. Chimica Therapeutica, Jul.-Aug. 1981-16, No. 4, pp. 321-326.
Apr. 11, 2023 Office Action issued in Chinese Patent Application No. 201980045913.6.
"Pd-Catalyzed Intermolecular Amidation of Aryl Halides: The Discovery that Xantphos Can Be Trans-Chelating in a Palladium Complex", Yin etal., J. Am. Chem. Soc. 2002,124, 6043-6048 (Year: 2002).
Nov. 6, 2023 Office Action issued in U.S. Appl. No. 17/259,451.
Aug. 16, 2022 Office Action issued in Russian Patent Application No. 2020142702.
Jul. 11, 2022 Office Action issued in Russian Patent Application No. 2020143617/04(081468).
Formulae of compounds having registry Nos. RN1875830-19-5, RN1216052-00-4, RN512834-81-0 and RN94631-91-1 found in "Registry database" and "entered STN before Feb. 29, 2016".
Mar. 24, 2023 Office Action issued in Chinese Patent Application No. 201980045893.2.
Apr. 12, 2023 Notice Of Allowance issued in U.S. Appl. No. 17/259,483.
Apr. 26, 2023 Corrected Notice Of Allowance issued in U.S. Appl. No. 17/259,483.
Jan. 3, 2023 Office Action Issued In U.S. Appl. No. 17/259,483.
Dardonville et al., "Bisguanidine, Bis(2-aminoimidazoline) and Polyamine Derivatives as Potent and Selective Chemotherapeutic Agents against Trypanosoma brucei rhodesiense. Synthesis and in vitro evaluation", J. Med .Chem. 2004, 47, 2296-2307.
Feb. 28, 2024 Office Action issued in U.S. Appl. No. 17/259,370.
Dardonville et al, "Bisguanidine, bis(2-aminoimidazoline), and polyamine derivatives as potent and selective chemotherapeutic agents against Trypanosoma brucei rhodesiense. Synthesis and in vitro evaluation", J. Med. Chem. 2004, 47, 9, pp. 2296-2307.
STN database Compounds, 2016.
Registry (STN) Compounds (1)-(83), entered on or before Sep. 2016.
STN compounds having registry Nos. RN 1990430-84-6, entered Sep. 9, 2016; RN 1988220-74-1, entered Sep. 7, 2016; and RN 1923315-23-4, entered Jun. 2, 2016.
Registry (STN) [online], date-of-search: Jul. 11, 2023: compounds having registry Nos. RN 1990473-92-1, entered Sep. 9, 2016; RN 1985111-93-0, entered Sep. 2, 2016; RN 1985111-90-7, entered Sep. 2, 2016; RN 1991597-00-2, entered Sep. 12, 2016; RN 1909835-58-0, entered May 13, 2016; RN 1906298-82-5, entered May 9, 2016.
STN Database Search Results including the following compounds: CAS Registry No. 1542686-52-1, entered Feb. 13, 2014; CAS Registry No. 1367998-11-5, entered Apr. 15, 2012; and CAS Registry No. 1258454-37-3, entered Jan. 5, 2011.

* cited by examiner

PHENYL-N-QUINOLINE DERIVATIVES FOR TREATING A RNA VIRUS INFECTION

The present invention relates to compounds useful for preventing and/or treating a RNA virus infection, and most preferably a RNA virus infection caused by RNA viruses belonging to group IV or V of the Baltimore classification.

The present invention further relates to some new compounds, in particular useful for preventing and/or treating a RNA virus infection, and most preferably a RNA virus infection caused by a RNA virus belonging to group IV or V of the Baltimore classification.

It further relates to the pharmaceutical compositions containing said new compounds and to the chemical synthesis processes for obtaining them.

BACKGROUND

Viruses are one of the major causes of diseases around the world. Viruses are generally defined as small, non-living, infectious agents that replicate only within living cells, as they do not possess a completely autonomous replication mechanism. Although diverse in shape and size, they typically consist of a virus particle (known as a "virion"), made from a protein coat which comprises at least one nucleic acid molecule and optionally, depending on the type of virus, one or more proteins or nucleoproteins.

Because viruses do not possess a completely autonomous replication mechanism, they must necessarily rely on the machinery and metabolism of the infected cell or host, in order to replicate and produce multiple copies of themselves.

Even though their replication cycle varies greatly between species, it is generally recognized that the life cycle of viruses includes six basic steps: attachment, penetration, uncoating, replication, assembly and release.

Depending on the nature of the targeted virus, therapeutic molecules have been designed which may interfere with one or more of those mechanisms.

Among those, the replication step involves not only the multiplication of the viral genome, but also the synthesis of viral messenger RNA, of viral protein synthesis, and the modulation or use of the transcription or translation machinery of the host. However, it is also clear that the type of genome (single-stranded, double-stranded, RNA, DNA . . . ) characterizes dramatically this replication step. For instance, most DNA viruses assemble in the nucleus while most RNA viruses develop solely in the cytoplasm. Also, there is increasing evidence that single-stranded RNA viruses such as Influenza use the host RNA splicing and maturation machinery.

Accordingly, and considering the implications of a given type of genome in the replication step, the Baltimore classification of viruses was developed. This classification clusters viruses into families (or "groups") depending on their type of genome. The present virus classification, as in 2018, comprises seven different groups:

Group I: double-stranded DNA viruses (dsDNA);
Group II: single-stranded DNA viruses (ssDNA);
Group III: double-stranded RNA viruses (dsRNA);
Group IV: (+)strand or sense RNA viruses ((+)ssRNA);
Group V: (−)strand or antisense RNA viruses ((−)ssRNA);
Group VI: single-stranded RNA viruses having DNA intermediates (ssRNA-RT);
Group VII: double-stranded DNA viruses having RNA intermediates (dsDNA-RT).

According to that classification, viruses belonging to the Group VI are not, stricto sensu, RNA viruses. For the same reasons, viruses belonging to the Group VII are not, stricto sensu, DNA viruses. One well-studied example of a virus family belonging to the Group VI is the family Retroviridae (retrovirus) which includes HIV. One well-studied example of a virus family belonging to the Group VII is the family Hepadnaviridae which includes the Hepatitis B virus (HBV).

As a representative of viruses pertaining to group IV, one may cite the Picornaviruses (which is a family of viruses that includes well-known viruses like Hepatitis A virus, enteroviruses, rhinoviruses, poliovirus, and foot-and-mouth virus), SARS virus, Hepatitis C virus, yellow fever virus, and rubella virus. The Togaviridae family also pertains to the group IV and a known genus thereof is *Alphavirus*, encompassing the Chikungunya virus. Flaviridae is also a family pertaining to group IV, encompassing a famous virus transmitted by mosquitoes, i.e. the Dengue virus.

As a representative of viruses pertaining to group V, one may cite the Filoviridae virus family encompassing the Ebola virus, the Paramyxoviridae family encompassing the Respiratory Syncytial virus (RSV), the Rhabdoviridae family, the Orthomyxoviridae family encompassing the Influenzavirus A, Influenzavirus B and Influenzavirus C.

Groups within the virus families particularly focused in the framework of the present invention are the ones encompassing RNA viruses, especially single-stranded RNA viruses, and more specifically RNA viruses belonging to group IV and group V of the Baltimore classification.

There are few cures for diseases caused by RNA virus infections, in particular single-stranded RNA viruses, and more specifically RNA virus infections from viruses belonging to group IV and V of the Baltimore classification. Treatment is focused on relieving the symptoms. Therefore, there is still a need to identify new antiviral drugs to treat RNA virus infections, such as RNA virus infection from group IV and V, in particular small chemical molecules.

Definitions

As used herein, the term "patient" refers to either an animal, such as a valuable animal for breeding, company or preservation purposes, or preferably a human or a human child, which is afflicted with, or has the potential to be afflicted with one or more diseases and conditions described herein.

In particular, as used in the present application, the term "patient" refers to a mammal such as a rodent, cat, dog, primate or human, preferably said subject is a human and also extends to birds.

The identification of those patients who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those patients who are in need of such treatment.

In the context of the invention, the term "treating" or "treatment", as used herein, means reversing, alleviating, inhibiting the progress of, or preventing the disease resulting from RNA virus infection, and more particularly RNA virus infection from group IV or V, or one or more symptoms of such disease.

As used herein, an "effective amount" refers to an amount of a compound of the present invention which is effective in preventing, reducing, eliminating, treating or controlling the symptoms of the herein-described diseases and conditions, i.e. RNA virus infection, and more particularly RNA virus infection from group IV and V. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

The term "effective amount" includes "prophylaxis-effective amount" as well as "treatment-effective amount".

The term "preventing", as used herein, means reducing the risk of onset or slowing the occurrence of a given phenomenon, namely in the present invention, a disease resulting from a RNA virus infection, and more particularly a RNA virus infection from group IV or V.

As used herein, «preventing» also encompasses «reducing the likelihood of occurrence» or «reducing the likelihood of reoccurrence».

The term "prophylaxis-effective amount" refers to a concentration of compound of this invention that is effective in inhibiting, preventing, decreasing the likelihood of the disease by RNA viruses, and more particularly by a RNA virus from group IV or V of the Baltimore classification, or preventing the RNA virus infection and in particular a RNA virus infection from group IV or V or preventing the delayed onset of the disease by the RNA virus, and more particularly by a RNA virus from group IV and V, when administered before infection, i.e. before, during and/or slightly after the exposure period to the RNA virus, and in particular to the RNA virus from the group IV and V.

Likewise, the term "treatment-effective amount" refers to a concentration of compound that is effective in treating the RNA virus infection, e.g. leads to a reduction in RNA viral infection, following examination when administered after infection has occurred.

As used herein, the term "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, an "viral infection or related condition" refers to an infection of condition related to a virus, more particularly said virus having a RNA genome, and especially a RNA virus belonging to groups IV or V according to the Baltimore classification. Viruses may be further classified in distinct families, orders and genus.

For reference, the content of the "Baltimore classification" which is reported herein further references to the virus taxonomy as set forth in the database of the 2017 International Committee of Taxonomy of Viruses (ICTV) as released online on Mar. 12, 2018 at http://ictvonline.org/virusTaxonomy.asp. This taxonomy is incorporated herein in its entirety.

Alphaviruses may in particular be considered by the invention and pertain to the Group IV RNA viruses and the Togaviridae family, which can be defined as positive-sense single-stranded RNA viruses or (+)ssRNA viruses. Their order is "Unassigned" according to the Virus Taxonomy of 2017. The Togaviridae family includes the *Alphavirus* and *Rubivirus* genus.

Examples of Alphaviruses which are considered by the invention include: Barmah Forest virus, Chikungunya virus, Mayaro virus, O'nyong'nyong virus, Ross River virus, Semliki Forest virus, Una virus, Eastern equine encephalitis virus, Tonate virus, Venezuelan equine encephalitis virus and Wester equine encephalitis virus.

Most preferably, an *Alphavirus* infection or *Alphavirus* related condition, according to the invention, is a Chikungunya virus infection or Chikungunya virus-related condition.

More particularly, Chikungunya virus (CHIKV) is a RNA virus which pertains to the *Alphavirus* genus which in turn belongs to the Togaviridae family, i.e. Group IV from the Baltimore classification. Chikungunya is a mosquito-borne viral disease first described during an outbreak in southern Tanzania in 1952. CHIKV is an enveloped, positive sense, single-stranded RNA virus with a genome of approximately 12 kb nucleotides long. The genome of CHIKV is organized as follows: 5'-cap-nsP1-nsP2-nsP3-nsP4-(junction region)-C-E3-E2-6k-E1-poly(A)-3', in which the first four proteins (nsP1-4) are nonstructural proteins, and the structural proteins are the capsid (C) and the envelope proteins (E). There is no distinct serotypic difference among CHIKV isolated from Africa, Asia and the islands of the Indian Ocean. Phylogenetic analyses based on E1 gene sequences can group CHIKV into three genotypes (lineages): Asian, east/central/south African (ECSA), and West African. The Asian genotype differed from the ECSA and West African genotypes by nucleotide levels of −5% and −15%, respectively. The African genotypes (ECSA versus West African) were −15% divergent. The amino acid identities across the three genotypes varied from 95.2 to 99.8%.

Chikungunya virus may cause outbreaks associated with severe morbidity.

Chikungunya is a viral disease transmitted to humans by infected mosquitoes. Both *Ae. aegypti* and *Ae. albopictus* have been implicated in large outbreaks of Chikungunya. Whereas *Ae. aegypti* is confined within the tropics and sub-tropics, *Ae. albopictus* also occurs in temperate and even cold temperate regions. In recent decades, *Ae. albopictus* has spread from Asia to become established in areas of Africa, Europe and the Americas.

After infection with Chikungunya virus, there is an incubation period lasting 2-4 days on average, followed by disease symptoms. Among such symptoms, fever and severe joint pain may be cited. Other symptoms include muscle pain, headache, nausea, back pain, fatigue, myalgia and rash. Severe clinical manifestations of Chikungunya infection can also occur, for example, haemorrhagic fever, conjunctivitis, photophobia, hepatitis, stomatitis. Neurologic manifestations such as encephalitis, febrile seizures, meningeal syndrome and acute encephalopathy were also reported.

Joint pain is often debilitating and can vary in duration.

The proximity of mosquito breeding sites to human habitation is a significant risk factor for Chikungunya.

The distribution of Chikungunya virus mainly occurs in Africa, India and South Eastern Asia. In recent decades, mosquito vectors of Chikungunya have spread to Europe and the Americas. In 2007, disease transmission was reported for the first time in a localized outbreak in northeastern Italy. Outbreaks have since been recorded in France and Croatia.

Dengue viruses which present various serotypes, may also be considered by the invention and pertain to the Group IV RNA viruses and the Flaviviridae family, which can be defined as a positive-sense single-stranded RNA or (+)ss RNA viruses. More particularly Dengue virus, is a (+)ssRNA virus belonging to group IV of the Baltimore classification. It is part of the *Flavivirus* genus, which belongs to the Flaviviridae family. Other viruses pertaining to the Flaviviridae family are hepatitis C virus and yellow fever virus.

Viruses of the Mononegavirales order are also particularly considered by the invention. The order Mononegavirales includes viruses belonging to Group V of the Baltimore classification. As of 2018, this order includes mainly the following virus families: Bornaviridae, Mymonaviridae, Filoviridae, Nyamiviridae, Paramyxoviridae, Pneumoviridae, Rhabdoviridae, and Sunviridae.

Human respiratory syncytial virus (HRSV) is a syncytial virus that causes respiratory tract infections. It is a major cause of lower respiratory tract infections and hospital visits during infancy and childhood. HRSV virus may in particular be considered by the invention and pertain to the Group V of RNA viruses. More particularly, RSV virus is a (−)ssRNA virus belonging to group V of the Baltimore classification. It is a pneumovirus which is part of the Paramyxoviridae family, which belongs to the Mononegavirales order. Among other viruses of the Mononegavirales order, those which are particularly considered by the invention include: measles virus, mumps virus, Nipah virus, rabies virus, and human parainfluenza virus (which includes HPIV-1, HPIV-2, HPIV-3 and HPIV-4). Of note, the Paramyxovirinae subfamily was conventionally merged into the Paramyxoviridae family, by reference to the taxonomy of the Mononegavirales order updated in 2016.

The virus genus which are particularly considered within the Paramyxoviridae family include: *Aquaparamyxovirus, Avulavirus, Ferlavirus, Henipavirus, Morbillivirus, Respirovirus* and *Rubulavirus* genus.

Viruses of the Orthomyxoviridae family are also particularly considered by the invention. The Orthomyxoviridae family belongs to an "Unassigned" order according to the 2017 Virus Taxonomy. The virus genus which are particularly considered within the Orthomyxoviridae family include: *Alphainfluenzavirus, Betainfluenzavirus, Deltainfluenzavirus, Gammainfluenzavirus, Isavirus, Quaranjavirus*, and *Thogotovirus*.

Influenzavirus A, Influenzavirus B, Influenzavirus C may in particular be considered by the invention and pertain to the Group V RNA viruses and the Orthomyxoviridae family, which can be defined as a negative-sense single-stranded RNA or (−)ss RNA viruses. *Isavirus* and *Thogotovirus* also belong to the Orthomyxoviridae order.

DETAILED DESCRIPTION OF THE INVENTION

The inventors have surprisingly found that phenyl-N-quinoline compounds are endowed with a broad-spectrum activity against RNA viruses, and more particularly single-stranded RNA viruses belonging to Group IV or V of the Baltimore classification. Groups IV and V include respectively (+)ssRNA viruses and (−)ssRNA viruses; which also refer to positive-sense single-stranded RNA viruses and negative-sense single-stranded RNA viruses.

For reference, the content of the «Baltimore classification» is considered in light of the Classification and Nomenclature of viruses as set forth in the 10th report on Virus Taxonomy dated 2017.

The present text describes a compound of formula (I)

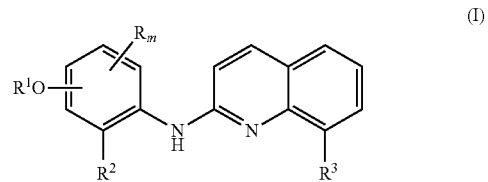

wherein
m is 0, 1 or 2,
$R^3$ represents a chlorine atom or a hydrogen atom,
R represents a $(C_1-C_4)$alkyl group, a $(C_3-C_6)$cycloalkyl group, a halogen atom, a $(C_1-C_5)$alkoxy group, a —$SO_2$—$NR_aR_b$ group, a —$SO_3H$ group, a —OH group, a —O—$SO_2$—$OR_c$ group or a —O—P(=O)—$(OR_c)(OR_d)$ group,
$R^1$ represents
  (i) a $CF_3$ group,
  (ii) a $(C_1-C_{10})$alkyl group, one of the carbon atom of said $(C_1-C_{10})$alkyl group being optionally replaced by an oxygen atom and said $(C_1-C_{10})$alkyl group being optionally substituted by one or more —$CF_3$ group, halogen atom, in particular fluorine atom, pyridyl group, phenyl group, $(C_3-C_6)$cycloalkyl group, $(C_3-C_6)$heterocycloalkyl group or hydroxy group,
  (iii) a $(C_3-C_6)$cycloalkyl group or a $(C_3-C_6)$heterocycloalkyl group, said groups being optionally substituted by one or two group(s) independently selected from a $(C_1-C_2)$alkyl group or a fluorine atom, or
  (iv) a phenyl group or a naphthyl group, said groups being optionally substituted by one or two group(s) independently selected from a $(C_1-C_4)$alkyl group, a halogen atom, a —COOR' group, a $(C_1-C_5)$alkoxy group, a —$SO_2$—$NR_aR_b$ group, a —$SO_3H$ group, a —OH group, a —O—$SO_2$—$OR_c$ group or a —O—P(=O)—$(OR_c)(OR_d)$ group, and
$R^2$ represents a hydrogen atom, a $(C_1-C_{10})$alkyl group, a $(C_3-C_6)$cycloalkyl or a $(C_3-C_6)$heterocycloalkyl group, said $(C_3-C_6)$cycloalkyl or $(C_3-C_6)$heterocycloalkyl group being optionally substituted by one or two group(s) independently selected from a $(C_1-C_2)$alkyl group or a fluorine atom,
the $OR^1$ group being in para or meta position on the phenyl with respect to the —NH— group,
R', $R_a$ and $R_b$ independently represent a hydrogen atom, a $(C_1-C_5)$alkyl group or a $(C_3-C_6)$cycloalkyl group, and
$R_c$ and $R_d$ independently represent a hydrogen atom, Li, Na, K, $N(R_a)_4$ or a benzyl group,
or any of its pharmaceutically acceptable salt,
for use in the treatment and/or prevention of a RNA virus infection caused by a RNA virus belonging to group IV or V of the Baltimore classification and in particular a Chikungunya viral infection, a Dengue viral infection, an Influenza viral infection or a RSV viral infection or a virus-related condition.

The above-mentioned compounds are particularly suitable for treating or preventing a virus infection or related condition, in particular a RNA virus infection caused by a RNA virus belonging to group IV or V of the Baltimore classification or related condition, and most preferably a Chikungunya viral infection, a Dengue viral infection, an Influenza viral infection or a RSV viral infection or a virus-related condition.

According to a first aspect, a subject-matter of the present invention relates to a compound of formula (I) or any of its pharmaceutically acceptable salt for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection

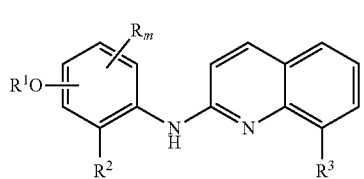

wherein
m is 0, 1 or 2,
R³ represents a chlorine atom or a hydrogen atom,
R represents a (C₁-C₄)alkyl group, a (C₃-C₆)cycloalkyl group, a halogen atom, a (C₁-C₅)alkoxy group, a —SO₂—NR$_a$R$_b$ group, a —SO₃H group, a —OH group, a —O—SO₂—OR$_c$ group or a —O—P(=O)—(OR$_c$)(OR$_d$) group,
R¹ represents
  (i) a CF₃ group,
  (ii) a (C₁-C₁₀)alkyl group, one of the carbon atom of said (C₁-C₁₀)alkyl group being optionally replaced by an oxygen atom and said (C₁-C₁₀)alkyl group being optionally substituted by one or more —CF₃ group, halogen atom, in particular fluorine atom, pyridyl group, phenyl group, (C₃-C₆)cycloalkyl group, (C₃-C₆)heterocycloalkyl group or hydroxy group,
  (iii) a (C₃-C₆)cycloalkyl group or a (C₃-C₆)heterocycloalkyl group, said groups being optionally substituted by one or two group(s) independently selected from a (C₁-C₂)alkyl group or a fluorine atom, or
  (iv) a phenyl group or a naphthyl group, said groups being optionally substituted by one or two group(s) independently selected from a (C₁-C₄)alkyl group, a halogen atom, a —COOR' group, a (C₁-C₅)alkoxy group, a —SO₂—NR$_a$R$_b$ group, a —SO₃H group, a —OH group, a —O—SO₂—OR$_c$ group or a —O—P(=O)—(OR$_c$)(OR$_d$) group, and
R² represents a hydrogen atom, a (C₁-C₁₀)alkyl group, a (C₃-C₆)cycloalkyl or a (C₃-C₆)heterocycloalkyl group, said (C₃-C₆)cycloalkyl or (C₃-C₆)heterocycloalkyl group being optionally substituted by one or two group(s) independently selected from a (C₁-C₂)alkyl group or a fluorine atom,
the OR¹ group being in para or meta position on the phenyl with respect to the —NH— group,
R', R$_a$ and R$_b$ independently represent a hydrogen atom, a (C₁-C₅)alkyl group or a (C₃-C₆)cycloalkyl group, and
R$_c$ and R$_d$ independently represent a hydrogen atom, Li, Na, K, N(R$_a$)₄ or a benzyl group,
wherein
when R² and R³ are both a hydrogen atom, then the R(s) are different from a methoxy group and OR¹ is different from a methoxy group or a benzyloxy group.

According to one embodiment, the present invention relates to a compound of formula (I) or any of its pharmaceutically acceptable salt as defined above for use in the treatment and/or prevention of a RNA virus infection caused by a RNA virus belonging to group IV or V of the Baltimore classification, wherein m is 0 or 1.

According to another embodiment, the present invention relates to a compound of formula (I) or any of its pharmaceutically acceptable salt as defined above for use in the treatment and/or prevention of a RNA virus infection caused by a RNA virus belonging to group IV or V of the Baltimore classification, wherein R³ represents a chlorine atom or a hydrogen atom.

According to another embodiment, the present invention relates to a compound of formula (I) or any of its pharmaceutically acceptable salt as defined above for use in the treatment and/or prevention of a RNA virus infection caused by a RNA virus belonging to group IV or V of the Baltimore classification, wherein R represents a (C₁-C₄)alkyl group or a (C₃-C₆)cycloalkyl group (that is to say when m is not 0).

According to another embodiment, the present invention relates to a compound of formula (I) or any of its pharmaceutically acceptable salt as defined above for use in the treatment and/or prevention of a RNA virus infection caused by a RNA virus belonging to group IV or V of the Baltimore classification, wherein R¹ represents
  (i) a CF₃ group,
  (ii) a (C₁-C₁₀)alkyl group, one of the carbon atom of said (C₁-C₁₀)alkyl group being optionally replaced by an oxygen atom and said (C₁-C₁₀)alkyl group being optionally substituted by one or more —CF₃ group, pyridyl group, phenyl group, (C₃-C₆)heterocycloalkyl group or hydroxy group,
  (iii) a (C₃-C₆)cycloalkyl group or a (C₃-C₆)heterocycloalkyl group, or
  (iv) a phenyl group or a naphthyl group, said groups being optionally substituted by one or two group(s) independently selected from a (C₁-C₄)alkyl group, a halogen atom, a —COOR' group, a (C₁-C₅)alkoxy group, or a —OH group, R' being a (C₁-C₅)alkyl group, and the OR¹ group being in para or meta position on the phenyl with respect to the —NH— group According to another embodiment, the present invention relates to a compound of formula (I) or any of its pharmaceutically acceptable salt as defined above for use in the treatment and/or prevention of a RNA virus infection caused by a RNA virus belonging to group IV or V of the Baltimore classification, wherein R² represents a hydrogen atom, a (C₁-C₁₀)alkyl group, or a (C₃-C₆)cycloalkyl group.

Any combination of the above-defined embodiments for m, R, R¹, R² and R³ with each other does form part of the instant invention.

According to a particular embodiment, a subject-matter of the present invention relates to a compound of formula (I) or any of its pharmaceutically acceptable salt for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection

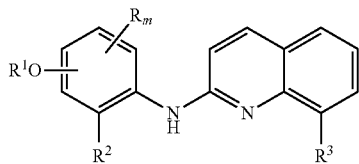

(I)

wherein m is 0, 1 or 2, $R^3$ represents a chlorine atom or a hydrogen atom,

R represents a ($C_1$-$C_4$)alkyl group, a ($C_3$-$C_6$)cycloalkyl group, a halogen atom, a ($C_1$-$C_5$)alkoxy group, a —$SO_2$—$NR_aR_b$ group, a —$SO_3H$ group, a —OH group, a —O—$SO_2$—$OR_c$ group or a —O—P(=O)—($OR_c$)($OR_d$) group, $R^1$ represents (i) a $CF_3$ group, (ii) a ($C_1$-$C_{10}$)alkyl group, one of the carbon atom of said ($C_1$-$C_{10}$)alkyl group being optionally replaced by an oxygen atom and said ($C_1$-$C_{10}$)alkyl group being optionally substituted by one or more —$CF_3$ group, halogen atom, in particular fluorine atom, pyridyl group, phenyl group, ($C_3$-$C_6$)cycloalkyl group, ($C_3$-$C_6$)heterocycloalkyl group or hydroxy group, (iii) a ($C_3$-$C_6$)cycloalkyl group or a ($C_3$-$C_6$)heterocycloalkyl group, said groups being optionally substituted by one or two group(s) independently selected from a ($C_1$-$C_2$)alkyl group or a fluorine atom, or (iv) a phenyl group or a naphthyl group, said groups being optionally substituted by one or two group(s) independently selected from a ($C_1$-$C_4$)alkyl group, a halogen atom, a —COOR' group, a ($C_1$-$C_5$)alkoxy group, a —$SO_2$—$NR_aR_b$ group, a —$SO_3H$ group, a —OH group, a —O—$SO_2$—$OR_c$ group or a —O—P(=O)—($OR_c$)($OR_d$) group, and $R^2$ represents a ($C_1$-$C_{10}$)alkyl group, a ($C_3$-$C_6$)cycloalkyl or a ($C_3$-$C_6$)heterocycloalkyl group, said ($C_3$-$C_6$)cycloalkyl or ($C_3$-$C_6$)heterocycloalkyl group being optionally substituted by one or two group(s) independently selected from a ($C_1$-$C_2$)alkyl group or a fluorine atom, the $OR^1$ group being in para or meta position on the phenyl with respect to the —NH— group, R', $R_a$ and $R_b$ independently represent a hydrogen atom, a ($C_1$-$C_5$)alkyl group or a ($C_3$-$C_6$)cycloalkyl group, and $R_c$ and $R_d$ independently represent a hydrogen atom, Li, Na, K, $N(R_a)_4$ or a benzyl group.

According to a particular embodiment, a subject-matter of the present invention relates to a compound of formula (I) as defined above, wherein m is 0 or 1 and R is a methyl group, and $R^1$ represents (i) a $CF_3$ group, (ii) a ($C_1$-$C_6$)alkyl group, one of the carbon atom of said ($C_1$-$C_6$)alkyl group being optionally replaced by an oxygen atom and said ($C_1$-$C_6$)alkyl group being optionally substituted by a —$CF_3$ group, a pyridyl group, a phenyl group, a ($C_3$-$C_6$)heterocycloalkyl group or a hydroxy group, or (iii) a ($C_3$-$C_6$)cycloalkyl group or a ($C_3$-$C_6$)heterocycloalkyl group, (iv) a phenyl group or a naphthyl group, said groups being optionally substituted by one or two group(s) independently selected from a ($C_1$-$C_4$)alkyl group, a —COOR' group, a ($C_1$-$C_4$)alkoxy group, a hydroxy group or a halogen atom, $R^2$ represents a hydrogen atom or a ($C_1$-$C_4$)alkyl group, R' represents a ($C_1$-$C_2$)alkyl group, or any of its pharmaceutically acceptable salt, for use in the treatment and/or prevention of a RNA virus infection caused by a RNA virus belonging to group IV or V of the Baltimore classification.

According to a particular embodiment, a subject-matter of the present invention relates to a compound of formula (I) or any of its pharmaceutically acceptable salt as defined above for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection, wherein m is 0 or 1 and R is a methyl group (that is to say when m is 1), and $R^1$ represents (i) a $CF_3$ group, (ii) a ($C_1$-$C_6$)alkyl group, one of the carbon atom of said ($C_1$-$C_6$)alkyl group being optionally replaced by an oxygen atom and said ($C_1$-$C_6$)alkyl group being optionally substituted by a —$CF_3$ group, a pyridyl group, a phenyl group, a ($C_3$-$C_6$)heterocycloalkyl group or a hydroxy group, or (iii) a ($C_3$-$C_6$)cycloalkyl group or a ($C_3$-$C_6$)heterocycloalkyl group, (iv) a phenyl group or a naphthyl group, said groups being optionally substituted by one or two group(s) independently selected from a ($C_1$-$C_4$)alkyl group, a —COOR' group, a ($C_1$-$C_4$)alkoxy group, a hydroxy group or a halogen atom, $R^2$ represents a hydrogen atom or a ($C_1$-$C_4$)alkyl group, R' represents a ($C_1$-$C_2$)alkyl group, wherein when $R^2$ and $R^3$ are both a hydrogen atom, then $OR^1$ substituent is different from a methoxy group or a benzyloxy group.

The present text describes a compound of formula (I)

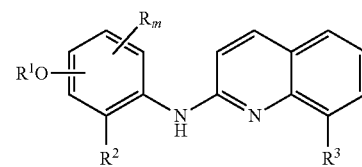

(I)

wherein m is 0, 1 or 2, $R^3$ represents a chlorine atom or a hydrogen atom,

R represents a ($C_1$-$C_4$)alkyl group, a ($C_3$-$C_6$)cycloalkyl group, a halogen atom, a ($C_1$-$C_5$)alkoxy group, a —$SO_2$—$NR_aR_b$ group, a —$SO_3H$ group, a —OH group, a —O—$SO_2$—$OR_c$ group or a —O—P(=O)—($OR_c$)($OR_d$) group, $R^1$ represents (i) a $CF_3$ group, (ii) a ($C_1$-$C_{10}$)alkyl group, one of the carbon atom of said ($C_1$-$C_{10}$)alkyl group being optionally replaced by an oxygen atom and said ($C_1$-$C_{10}$)alkyl group being optionally substituted by one or more —CF$_3$ group, halogen atom, in particular fluorine atom, pyridyl group, phenyl group, (C$_3$-C$_6$)cycloalkyl, (C$_3$-C$_6$)heterocycloalkyl group or hydroxy group, (iii) a (C$_3$-C$_6$)cycloalkyl or a (C$_3$-C$_6$)heterocycloalkyl group, said group being optionally substituted by one or two group(s) independently selected from a (C$_1$-C$_2$)alkyl group or a fluorine atom, or (iv) a phenyl group or a naphthyl group, said groups being optionally substituted by one or two group(s) independently selected from a (C$_1$-C$_4$)alkyl group, a halogen atom, a —COOR' group, a (C$_1$-C$_5$)alkoxy group, a —SO$_2$—NR$_a$R$_b$ group, a —SO$_3$H group, a —OH group, a —O—SO$_2$—OR$_c$ group or a —O—P(=O)—(OR$_c$)(OR$_d$) group, and R$^2$ represents a hydrogen atom, a (C$_1$-C$_{10}$)alkyl group, a (C$_3$-C$_6$)cycloalkyl or a (C$_3$-C$_6$)heterocycloalkyl group, said (C$_3$-C$_6$)cycloalkyl or (C$_3$-C$_6$)heterocycloalkyl groups being optionally substituted by one or two group(s) independently selected from a (C$_1$-C$_2$)alkyl group or a fluorine atom, the OR$^1$ group being in para or meta position on the phenyl with respect to the —NH— group, R', R$_a$ and R$_b$ independently represent a hydrogen atom, a (C$_1$-C$_5$)alkyl group or a (C$_3$-C$_6$)cycloalkyl group, and R$_c$ and R$_d$ independently represent a hydrogen atom, Li, Na, K, N(R$_a$)$_4$ or a benzyl group, wherein when R$^1$ means (i) then R$^2$ is different from a methyl group and when R$^1$ means an unsubstituted phenyl, then R$^2$ and R$^3$ are not simultaneously hydrogen atoms, or any of its pharmaceutically acceptable salt, for use in the treatment and/or prevention of a RNA virus infection from group IV and V of the Baltimore classification.

According to a particular embodiment, the present invention relates to a compound of formula (I) or any of its pharmaceutically acceptable salt as defined above for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection

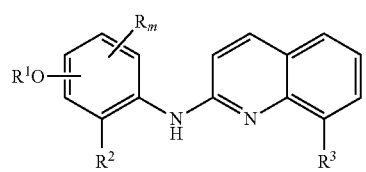

(I)

wherein m is 0, 1 or 2,

R$^3$ represents a chlorine atom or a hydrogen atom,

R represents a (C$_1$-C$_4$)alkyl group, a (C$_3$-C$_6$)cycloalkyl group, a halogen atom, a (C$_1$-C$_5$)alkoxy group, a —SO$_2$—NR$_a$R$_b$ group, a —SO$_3$H group, a —OH group, a —O—SO$_2$—OR$_c$ group or a —O—P(=O)—(OR$_c$)(OR$_d$) group, R$^1$ represents (i) a CF$_3$ group, (ii) a (C$_1$-C$_{10}$)alkyl group, one of the carbon atom of said (C$_1$-C$_{10}$)alkyl group being optionally replaced by an oxygen atom and said (C$_1$-C$_{10}$)alkyl group being optionally substituted by one or more —CF$_3$ group, halogen atom, in particular fluorine atom, pyridyl group, phenyl group, (C$_3$-C$_6$)cycloalkyl, (C$_3$-C$_6$)heterocycloalkyl group or hydroxy group, (iii) a (C$_3$-C$_6$)cycloalkyl or a (C$_3$-C$_6$)heterocycloalkyl group, said group being optionally substituted by one or two group(s) independently selected from a (C$_1$-C$_2$)alkyl group or a fluorine atom, or (iv) a phenyl group or a naphthyl group, said groups being optionally substituted by one or two group(s) independently selected from a (C$_1$-C$_4$)alkyl group, a halogen atom, a —COOR' group, a (C$_1$-C$_5$)alkoxy group, a —SO$_2$—NR$_a$R$_b$ group, a —SO$_3$H group, a —OH group, a —O—SO$_2$—OR$_c$ group or a —O—P(=O)—(OR$_c$)(OR$_d$) group, and R$^2$ represents a hydrogen atom, a (C$_1$-C$_{10}$)alkyl group, a (C$_3$-C$_6$)cycloalkyl or a (C$_3$-C$_6$)heterocycloalkyl group, said (C$_3$-C$_6$)cycloalkyl or (C$_3$-C$_6$)heterocycloalkyl groups being optionally substituted by one or two group(s) independently selected from a (C$_1$-C$_2$)alkyl group or a fluorine atom, the OR$^1$ group being in para or meta position on the phenyl with respect to the —NH— group, R', R$_a$ and R$_b$ independently represent a hydrogen atom, a (C$_1$-C$_5$)alkyl group or a (C$_3$-C$_6$)cycloalkyl group, and R$_c$ and R$_d$ independently represent a hydrogen atom, Li, Na, K, N(R$_a$)$_4$ or a benzyl group, wherein when R$^1$ means (i) then R$^2$ is different from a methyl group and when R$^1$ means an unsubstituted phenyl, then R$^2$ and R$^3$ are not simultaneously hydrogen atoms, and wherein when R$^2$ and R$^3$ are both a hydrogen atom, then the R(s) are different from a methoxy group and OR$^1$ is different from a methoxy group or a benzyloxy group.

According to a preferred embodiment, a subject-matter of the present invention relates to a compound of formula (I) or any of its pharmaceutically acceptable salt for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection

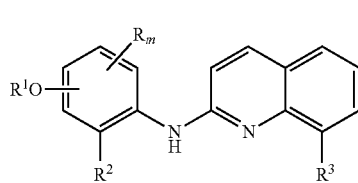

(I)

wherein m is 0, 1 or 2,

R$^3$ represents a chlorine atom or a hydrogen atom,

R represents a (C$_1$-C$_4$)alkyl group, a (C$_3$-C$_6$)cycloalkyl group, a halogen atom, a (C$_1$-C$_5$)alkoxy group, a —SO$_2$—NR$_a$R$_b$ group, a —SO$_3$H group, a —OH group, a —O—SO$_2$—OR$_c$ group or a —O—P(=O)—(OR$_c$)(OR$_d$) group, $R^1$ represents
(i) a $CF_3$ group,
(ii) a $(C_1-C_{10})$alkyl group, one of the carbon atom of said $(C_1-C_{10})$alkyl group being optionally replaced by an oxygen atom and said $(C_1-C_{10})$alkyl group being optionally substituted by one or more —$CF_3$ group, halogen atom, in particular fluorine atom, pyridyl group, phenyl group, $(C_3-C_6)$cycloalkyl group, $(C_3-C_6)$heterocycloalkyl group or hydroxy group,
(iii) a $(C_3-C_6)$cycloalkyl group or a $(C_3-C_6)$heterocycloalkyl group, said groups being optionally substituted by one or two group(s) independently selected from a $(C_1-C_2)$alkyl group or a fluorine atom, or
(iv) a phenyl group or a naphthyl group, said groups being optionally substituted by one or two group(s) independently selected from a $(C_1-C_4)$alkyl group, a halogen atom, a —COOR' group, a $(C_1-C_5)$alkoxy group, a —$SO_2$—$NR_aR_b$ group, a —$SO_3H$ group, a —OH group, a —O—$SO_2$—$OR_c$ group or a —O—P(=O)—$(OR_c)(OR_d)$ group, and $R^2$ represents a $(C_1-C_{10})$alkyl group or a $(C_3-C_6)$cycloalkyl group, said $(C_3-C_6)$cycloalkyl group being optionally substituted by one or two group(s) independently selected from a $(C_1-C_2)$alkyl group or a fluorine atom, preferably $R^2$ represents a methyl group, an ethyl group, an isobutyl group, a propyl group or a cyclopropyl group, and still more preferably $R^2$ represents a cyclopropyl group, the $OR^1$ group being in para or meta position on the phenyl with respect to the —NH— group, R', $R_a$ and $R_b$ independently represent a hydrogen atom, a $(C_1-C_5)$alkyl group or a $(C_3-C_6)$cycloalkyl group, and $R_c$ and $R_d$ independently represent a hydrogen atom, Li, Na, K, $N(R_a)_4$ or a benzyl group.

According to a more preferred embodiment, the present invention relates to a compound of formula (I) as defined in the present invention or any of its pharmaceutically acceptable salts for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection, wherein $R^2$ represents a methyl group, an ethyl group, an isobutyl group or a propyl group.

According to a still more preferred embodiment, the present invention relates to a compound of formula (I) as defined in the present invention or any of its pharmaceutically acceptable salts for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection, said compound being chosen among compounds 1, 2, 3, 5, 6, 7, 9 to 19, 21 to 26, 38 to 41, 43, 45, 47 to 51, 53 to 59, 61, 63 to 71, 74 to 76, 78 and 79 as defined below.

According to an even more preferred embodiment, the present invention relates to a compound of formula (I) as defined in the present invention or any of its pharmaceutically acceptable salts for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection, wherein $R^2$ represents a methyl group.

According to a still more preferred embodiment, the present invention relates to a compound of formula (I) as defined in the present invention or any of its pharmaceutically acceptable salts for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection, wherein said compound is chosen among compounds 1, 5, 9, 10, 11, 12, 14 to 18, 21 to 26, 38, 40, 43, 45, 47 to 51, 53 to 59, 63 to 70 and 78.

According to another even more preferred embodiment, the present invention relates to a compound of formula (I) as defined in the present invention or any of its pharmaceutically acceptable salts for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection, wherein $R^2$ represents a cyclopropyl group.

According to a still more preferred embodiment, the present invention relates to a compound of formula (I) as defined in the present invention or any of its pharmaceutically acceptable salts for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection, said compound being chosen among compounds 4, 8, 20, 42, 44, 46, 52, 72, and 73 as defined below.

According to a particular embodiment, the present invention relates to a compound of formula (I) or any of its pharmaceutically acceptable salt for use in the treatment and/or prevention of a RNA virus infection caused by a RNA virus belonging to group IV or V of the Baltimore classification, preferably a Chikungunya viral infection, a RSV viral infection and/or a Dengue viral infection

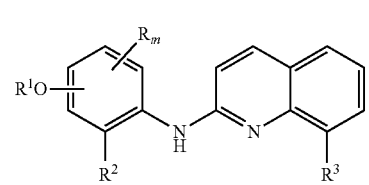

wherein
m is 0 or 1,
$R^3$ represents a chlorine atom or a hydrogen atom,
R represents a $(C_1-C_4)$alkyl group or a $(C_3-C_6)$cycloalkyl group, R¹ represents
(i) a CF₃ group,
(ii) a (C₁-C₁₀)alkyl group, one of the carbon atom of said (C₁-C₁₀)alkyl group being optionally replaced by an oxygen atom and said (C₁-C₁₀)alkyl group being optionally substituted by one or more —CF₃ group, pyridyl group, or phenyl group,
(iii) a (C₃-C₆)cycloalkyl group, or
(iv) a phenyl group or a naphthyl group, said groups being optionally substituted by one or two group(s) independently selected from a (C₁-C₄)alkyl group, a halogen atom, a (C₁-C₅)alkoxy group, or a —OH group, and
R² represents a hydrogen atom, a (C₁-C₁₀)alkyl group, or a (C₃-C₆)cycloalkyl group,
the OR¹ group being in para or meta position on the phenyl with respect to the —NH— group,
wherein
when R² and R³ are both a hydrogen atom, then OR¹ is different from a methoxy group or a benzyloxy group.

According to another preferred embodiment, the present invention relates to a compound of formula (I) or any of its pharmaceutically acceptable salt as defined above for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection and/or a Chikungunya viral infection, which is chosen among compounds 1 to 8, 10, 12 to 14, 16, 17, 20 to 23, 28, 29, 31, 32, 38 to 57, 63, 76 and 77 as defined below.

According to a particular embodiment, the present invention relates to a compound of formula (I) or any of its pharmaceutically acceptable salt for use in the treatment and/or prevention of a RNA virus infection caused by a RNA virus belonging to group IV or V of the Baltimore classification, preferably a Chikungunya viral infection

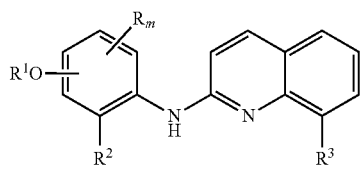

(I)

wherein
m is 0 or 1,
R³ represents a chlorine atom or a hydrogen atom,
R represents a (C₁-C₄)alkyl group,
R¹ represents
(i) a CF₃ group,
(ii) a (C₁-C₁₀)alkyl group, one of the carbon atom of said (C₁-C₁₀)alkyl group being optionally replaced by an oxygen atom and said (C₁-C₁₀)alkyl group being optionally substituted by one or more —CF₃ group or pyridyl group,
(iii) a (C₃-C₆)cycloalkyl group, or
(iv) a phenyl group, said phenyl group being optionally substituted by one or two group(s) independently selected from a (C₁-C₄)alkyl group, a halogen atom, or a (C₁-C₅)alkoxy group, and R² represents a hydrogen atom, a (C₁-C₁₀)alkyl group, or a (C₃-C₆)cycloalkyl group,
the OR¹ group being in para or meta position on the phenyl with respect to the —NH— group,
wherein
when R² and R³ are both a hydrogen atom, then OR¹ is different from a methoxy group.

According to another preferred embodiment, the present invention relates to a compound of formula (I) or any of its pharmaceutically acceptable salt as defined above for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a Chikungunya viral infection, which is chosen among compounds 1 to 4, 6 to 8, 10, 12 to 14, 16, 17, 20 to 23, 29, 31, 32, and 38 to 46, as defined below.

According to a particular embodiment, the present invention relates to a compound of formula (I) or any of its pharmaceutically acceptable salt for use in the treatment and/or prevention of a RNA virus infection caused by a RNA virus belonging to group IV or V of the Baltimore classification, preferably a RSV viral infection

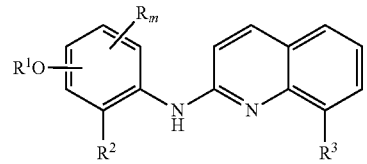

(I)

wherein
m is 0 or 1,
R³ represents a chlorine atom or a hydrogen atom,
R represents a (C₁-C₄)alkyl group or a (C₃-C₆)cycloalkyl group,
R¹ represents
(i) a CF₃ group,
(ii) a (C₁-C₁₀)alkyl group, one of the carbon atom of said (C₁-C₁₀)alkyl group being optionally replaced by an oxygen atom and said (C₁-C₁₀)alkyl group being optionally substituted by one or more phenyl group,
(iii) a phenyl group or a naphthyl group, said groups being optionally substituted by one or two group(s) independently selected from a halogen atom, a (C₁-C₅)alkoxy group, or a —OH group, and
R² represents a hydrogen atom, a (C₁-C₁₀)alkyl group, or a (C₃-C₆)cycloalkyl group,
the OR¹ group being in para or meta position on the phenyl with respect to the —NH— group,
wherein
when R² and R³ are both a hydrogen atom, then OR¹ is different from a methoxy group or a benzyloxy group.

According to another preferred embodiment, the present invention relates to a compound of formula (I) or any of its pharmaceutically acceptable salt as defined above for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection, which is chosen among compounds 1, 6, 10, 13, 28, 38, 43, 47, 48, 49, 50, 51, 52, 53, 54, 55, 56, and 57 as defined below.

According to a particular embodiment, the present invention relates to a compound of formula (I) or any of its pharmaceutically acceptable salt for use in the treatment and/or prevention of a RNA virus infection caused by a RNA virus belonging to group IV or V of the Baltimore classification, preferably a Dengue viral infection

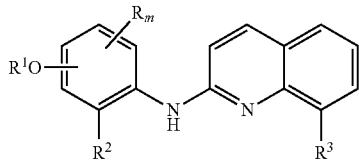

wherein
m is 0 or 1,
$R^3$ represents a chlorine atom or a hydrogen atom,
R represents a $(C_1-C_4)$alkyl group,
$R^1$ represents
  (i) a $CF_3$ group,
  (ii) a $(C_1-C_{10})$alkyl group, one of the carbon atom of said $(C_1-C_{10})$alkyl group being optionally replaced by an oxygen atom and said $(C_1-C_{10})$alkyl group being optionally substituted by one or more phenyl group,
  (iii) a $(C_3-C_6)$cycloalkyl group, or
  (iv) a phenyl group or a naphthyl group, said groups being optionally substituted by one or two group(s) independently selected from a halogen atom, or a $(C_1-C_5)$alkoxy group, and
$R^2$ represents a hydrogen atom, a $(C_1-C_{10})$alkyl group, or a $(C_3-C_6)$cycloalkyl group,
the $OR^1$ group being in para or meta position on the phenyl with respect to the —NH— group,
wherein
when $R^2$ and $R^3$ are both a hydrogen atom, then $OR^1$ is different from a methoxy group or a benzyloxy group.

According to another preferred embodiment, the present invention relates to a compound of formula (I) or any of its pharmaceutically acceptable salt as defined above for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a Dengue viral infection, which is chosen among compounds 5, 10, 12, 13, 16, 20, 22, 39, 40, 42 to 44, 46, 47, 54, 56, 63, 76 and 77 as defined below.

According to another particular embodiment, the present invention relates to a compound of formula (I) as defined in the present invention or any of its pharmaceutically acceptable salts for use in the treatment and/or prevention of a RNA virus infection caused by a RNA virus belonging to group IV or V of the Baltimore classification, wherein the RNA virus infection caused by a RNA virus belonging to group IV or V of the Baltimore classification is chosen among a RSV viral infection, a Chikungunya viral infection, a Dengue viral infection, and an Influenza viral infection, more particularly chosen among a RSV viral infection, a Chikungunya viral infection and a Dengue viral infection, and still more preferably is a RSV viral infection.

The present invention further extends to compounds as such. Among said new compounds, compounds of formula (I) as defined in the following groups 1 to 4 as defined below pertain to the present invention.

According to a particular embodiment, group 1, an additional subject-matter of the present invention is a compound of formula (I) as defined above, wherein
m, $R^1$, $R^3$ and R are as defined above,
$R^2$ represents a $(C_3-C_6)$cycloalkyl group or a $(C_3-C_6)$heterocycloalkyl group, said groups being optionally substituted by one or two group(s) independently selected from a $(C_1-C_2)$alkyl group or a fluorine atom,
or any of its pharmaceutically acceptable salt.

According to a particular embodiment, group 2, an additional subject-matter of the present invention is a compound of formula (I) as defined above, wherein
$R^1$ represents
  (i) a $CF_3$ group, provided that $R^2$ is not a hydrogen atom or a methyl group,
  (ii) a $(C_1-C_{10})$alkyl group, one of the carbon atom of said $(C_1-C_{10})$alkyl group being optionally replaced by an oxygen atom and said $(C_1-C_{10})$alkyl group being optionally substituted by one or more —$CF_3$ group, halogen atom, in particular fluorine atom, pyridyl group, phenyl group, $(C_3-C_6)$cycloalkyl $(C_3-C_6)$heterocycloalkyl group or hydroxy group, provided that $R^2$ is not a hydrogen atom, or
  (iii) a $(C_3-C_6)$cycloalkyl or a $(C_3-C_6)$heterocycloalkyl group, said groups being optionally substituted by one or two group(s) independently selected from $(C_1-C_2)$alkyl group or fluorine atom,
or any of its pharmaceutically acceptable salt.

Still according to this particular embodiment, $R^1$ may be preferably (i) or (ii).

According to another particular embodiment, group 3, an additional subject-matter of the present invention is a compound of formula (I) as defined above, wherein m, R, $R^2$ and $R^3$ are as defined above, and
$R^1$ represents
  (i) a $(C_1-C_{10})$alkyl group, one of the carbon atom of said $(C_1-C_{10})$alkyl group being optionally replaced by an oxygen atom and said $(C_1-C_{10})$alkyl group being optionally substituted by one or more —$CF_3$ group, halogen atom, in particular fluorine atom, pyridyl group, phenyl group, $(C_3-C_6)$cycloalkyl group or $(C_3-C_6)$heterocycloalkyl group or hydroxy group, provided that $R^1$ encompasses a $(C_3-C_6)$cycloalkyl or a $(C_3-C_6)$heterocycloalkyl group, or
  (ii) a $(C_3-C_6)$cycloalkyl or a $(C_3-C_6)$heterocycloalkyl group, said groups being optionally substituted by one or two group(s) independently selected from $(C_1-C_2)$alkyl group or fluorine atom, or any of its pharmaceutically acceptable salt.

In the previous embodiment (group 3), in point (i), the expression "provided that $R^1$ encompasses a $(C_3-C_6)$cycloalkyl or a $(C_3-C_6)$heterocycloalkyl group," means in the sense of the present invention that when $R^1$ represents a $(C_1-C_{10})$alkyl group, the $(C_1-C_{10})$alkyl group must comprise at least one substituent chosen among a $(C_3-C_6)$cycloalkyl and a $(C_3-C_6)$heterocycloalkyl group.

According to another particular embodiment, group 4, an additional subject-matter of the present invention is a compound of formula (I) as defined above, wherein m, $R^2$, $R^3$, R', $R_a$, $R_b$, $R_c$, $R_d$ and R are as defined above, and $R^1$ represents a naphthyl group optionally substituted by one or two group(s) independently selected from a $(C_1-C_4)$alkyl group, a halogen atom, a —COOR' group, a $(C_1-C_5)$alkoxy group, a —$SO_2$—$NR_aR_b$ group, a —$SO_3H$ group, a —OH group, a —O—$SO_2$—$OR_c$ group or a —O—P(=O)—$(OR_c)$$(OR_d)$ group or represents a phenyl group substituted by one or two group(s) independently selected from a $(C_1-C_4)$alkyl group, a halogen atom, a —COOR' group, a $(C_1-C_5)$alkoxy group, a —$SO_2$—$NR_aR_b$ group, a —$SO_3H$ group, a —OH group, a —O—$SO_2$—$OR_c$ group or a —O—P(=O)—$(OR_c)$$(OR_d)$ group, or any of its pharmaceutically acceptable salt.

According to another particular embodiment, group 5, an additional subject-matter of the present invention is a compound of formula (I) as defined above, wherein m, R, $R^2$ and $R^3$ are as defined above, and $R^1$ represents
(i) a $(C_1-C_{10})$alkyl group, one of the carbon atom of said $(C_1-C_{10})$alkyl group being optionally replaced by an oxygen atom and said $(C_1-C_{10})$alkyl group being optionally substituted by one or more —$CF_3$ group, halogen atom, in particular fluorine atom, pyridyl group, phenyl group, $(C_3-C_6)$cycloalkyl group or $(C_3-C_6)$heterocycloalkyl group or hydroxy group, provided that $R^1$ encompasses a $(C_3-C_6)$cycloalkyl or a $(C_3-C_6)$heterocycloalkyl group, or
(ii) a $(C_3-C_6)$cycloalkyl or a $(C_3-C_6)$heterocycloalkyl group, said groups being optionally substituted by one or two group(s) independently selected from $(C_1-C_2)$alkyl group or fluorine atom,
or any of its pharmaceutically acceptable salt,
wherein
when $R^2$ and $R^3$ are both a hydrogen atom, then the R(s) are different from a methoxy group and $OR^1$ is different from a methoxy group or a benzyloxy group.

In the previous embodiment (group 5), in point (i), the expression "provided that $R^1$ encompasses a $(C_3-C_6)$cycloalkyl or a $(C_3-C_6)$heterocycloalkyl group," means in the sense of the present invention that when $R^1$ represents a $(C_1-C_{10})$ alkyl group, the $(C_1-C_{10})$alkyl group must comprise at least one substituent chosen among a $(C_3-C_6)$cycloalkyl and a $(C_3-C_6)$heterocycloalkyl group.

Such specific compounds pertain to the new compounds of formula (I).

According to a preferred embodiment of the present invention, the compound of formula (I) for use in the treatment and/or prevention of a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection, is chosen from:

(1) 8-chloro-N-(2-methyl-4-(trifluoromethoxy)phenyl)quinolin-2-amine
(2) 8-chloro-N-(2-ethyl-4-(trifluoromethoxy)phenyl)quinolin-2-amine
(3) 8-chloro-N-(2-isobutyl-4-(trifluoromethoxy)phenyl)quinolin-2-amine
(4) 8-chloro-N-(2-cyclopropyl-4-(trifluoromethoxy)phenyl)quinolin-2-amine
(5) 8-chloro-N-(2-ethyl-6-methyl-4-(trifluoromethoxy)phenyl)quinolin-2-amine
(6) 8-chloro-N-(2-propyl-4-(trifluoromethoxy)phenyl)quinolin-2-amine
(7) N-(2-ethyl-4-(trifluoromethoxy)phenyl)quinolin-2-amine
(8) N-(2-cyclopropyl-4-(trifluoromethoxy)phenyl)quinolin-2-amine
(9) 8-chloro-N-(4-methoxy-2-methylphenyl)quinolin-2-amine
(10) 8-chloro-N-(4-isopropoxy-2-methylphenyl)quinolin-2-amine
(11) 8-chloro-N-(4-(2-methoxyethoxy)-2-methylphenyl)quinolin-2-amine
(12) 8-chloro-N-(4-ethoxy-2-methylphenyl)quinolin-2-amine
(13) 8-chloro-N-(2-ethyl-4-isopropoxyphenyl)quinolin-2-amine
(14) 8-chloro-N-(2-methyl-4-(2-(trifluoromethoxy)ethoxy)phenyl)quinolin-2-amine
(15) 8-chloro-N-(4-isopropoxy-2,6-dimethylphenyl)quinolin-2-amine
(16) 8-chloro-N-(4-(cyclopentyloxy)-2-methylphenyl)quinolin-2-amine
(17) 8-chloro-N-(4-(cyclohexyloxy)-2-methylphenyl)quinolin-2-amine
(18) 2-(4-((8-chloroquinolin-2-yl)amino)-3-methylphenoxy)ethanol
(19) N-(2-ethyl-4-isopropoxyphenyl)quinolin-2-amine
(20) 8-chloro-N-(2-cyclopropyl-4-isopropoxyphenyl)quinolin-2-amine
(21) 8-chloro-N-(4-isopropoxy-2,3-dimethylphenyl)quinolin-2-amine
(22) 8-chloro-N-(4-cyclobutoxy-2-methylphenyl)quinolin-2-amine
(23) 8-chloro-N-(2-methyl-4-(pyridin-2-ylmethoxy)phenyl)quinolin-2-amine
(24) 8-chloro-N-(2-methyl-4-(pyridin-4-ylmethoxy)phenyl)quinolin-2-amine
(25) 8-chloro-N-(2-methyl-4-((3-methyloxetan-3-yl)methoxy)phenyl)quinolin-2-amine
(26) 8-chloro-N-(2-methyl-4-(oxetan-3-yloxy)phenyl)quinolin-2-amine
(27) N-(4-phenoxyphenyl)quinolin-2-amine
(28) N-(4-(p-tolyloxy)phenyl)quinolin-2-amine
(29) N-(4-(2-fluorophenoxy)phenyl)quinolin-2-amine
(30) methyl 2-(4-(quinolin-2-ylamino)phenoxy)benzoate
(31) 8-chloro-N-(4-(p-tolyloxy)phenyl)quinolin-2-amine
(32) 8-chloro-N-(4-(2-fluorophenoxy)phenyl)quinolin-2-amine
(33) methyl 2-(4-((8-chloroquinolin-2-yl)amino)phenoxy)benzoate
(34) N-(4-(4-chlorophenoxy)phenyl)quinolin-2-amine
(35) N-(4-(4-fluorophenoxy)phenyl)quinolin-2-amine
(36) 8-chloro-N-(4-(4-chlorophenoxy)phenyl)quinolin-2-amine
(37) 8-chloro-N-(4-(4-fluorophenoxy)phenyl)quinolin-2-amine
(38) N-(4-(2-fluorophenoxy)-2-methylphenyl)quinolin-2-amine
(39) N-(2-ethyl-4-(2-fluorophenoxy)phenyl)quinolin-2-amine
(40) 8-chloro-N-(4-isopropoxy-5-isopropyl-2-methylphenyl)quinolin-2-amine
(41) 8-chloro-N-(4-cyclobutoxy-2-ethylphenyl)quinolin-2-amine
(42) 8-chloro-N-(4-cyclobutoxy-2-cyclopropylphenyl)quinolin-2-amine
(43) 8-chloro-N-(4-isopropoxy-2,5-dimethylphenyl)quinolin-2-amine

(44) 8-chloro-N-(4-(cyclopentyloxy)-2-cyclopropylphenyl)quinolin-2-amine
(45) N-(4-(2-fluoro-4-methoxyphenoxy)-2-methylphenyl)quinolin-2-amine
(46) N-(2-cyclopropyl-4-(2-fluorophenoxy)phenyl)quinolin-2-amine
(47) N-(4-(benzyloxy)-2-methylphenyl)-8-chloroquinolin-2-amine
(48) 8-chloro-N-(5-cyclopropyl-4-isopropoxy-2-methylphenyl)quinolin-2-amine
(49) 8-chloro-N-(3-isopropoxy-2-methylphenyl)quinolin-2-amine
(50) N-(3-(benzyloxy)-2-methylphenyl)-8-chloroquinolin-2-amine
(51) N-(4-(4-methoxyphenoxy)-2-methylphenyl)quinolin-2-amine
(52) N-(2-cyclopropyl-4-(2-fluoro-4-methoxyphenoxy)phenyl)quinolin-2-amine
(53) 3-fluoro-4-(3-methyl-4-(quinolin-2-ylamino)phenoxy)phenol
(54) 8-chloro-N-(2-methyl-4-(naphthalen-1-yloxy)phenyl)quinolin-2-amine
(55) 8-chloro-N-(2-methyl-3-phenoxyphenyl)quinolin-2-amine
(56) 8-chloro-N-(2-methyl-4-phenoxyphenyl)quinolin-2-amine 2,2,2-trifluoroacetate
(57) 8-chloro-N-(2-methyl-4-(naphthalen-2-yloxy)phenyl)quinolin-2-amine
(58) N-(2-methyl-3-phenoxyphenyl)quinolin-2-amine
(59) 8-chloro-N-(2-methyl-3-(pyridin-3-ylmethoxy)phenyl)quinolin-2-amine
(60) 8-chloro-N-(3-phenoxyphenyl)quinolin-2-amine
(61) 8-chloro-N-(2-methyl-5-phenoxyphenyl)quinolin-2-amine
(62) 8-chloro-N-(4-phenoxyphenyl)quinolin-2-amine
(63) 8-chloro-N-(4-(2-fluorophenoxy)-2,5-dimethylphenyl)quinolin-2-amine 2,2,2-trifluoroacetate
(64) 8-chloro-N-(2,6-dimethyl-4-phenoxyphenyl)quinolin-2-amine
(65) N-(4-isopropoxy-2,5-dimethylphenyl)quinolin-2-amine
(66) N-(2,6-dimethyl-4-phenoxyphenyl)quinolin-2-amine
(67) N-(4-isopropoxy-2-methylphenyl)quinolin-2-amine
(68) N-(2-methyl-4-phenoxyphenyl)quinolin-2-amine
(69) 2-(3-((8-chloroquinolin-2-yl)amino)-4-methylphenoxy)ethanol
(70) 2-(3-((8-chloroquinolin-2-yl)amino)-2-methylphenoxy)ethanol
(71) 8-chloro-N-(2-methyl-6-propyl-4-(trifluoromethoxy)phenyl)quinolin-2-amine
(72) 8-chloro-N-(2-cyclopropyl-6-methyl-4-(trifluoromethoxy)phenyl)quinolin-2-amine
(73) N-(2-cyclopropyl-4-isopropoxyphenyl)quinolin-2-amine
(74) N-(4-isopropoxy-2-propylphenyl)quinolin-2-amine
(75) N-(2-propyl-4-(trifluoromethoxy)phenyl)quinolin-2-amine
(76) N-(2-ethyl-4-(2-fluoro-4-methoxyphenoxy)phenyl)quinolin-2-amine
(77) N-(4-(2-fluoro-4-methoxyphenoxy)phenyl)quinolin-2-amine
(78) 8-chloro-N-(5-isopropoxy-2-methylphenyl)quinolin-2-amine
(79) 2-(4-((8-chloroquinolin-2-yl)amino)-3-propylphenoxy)ethanol
and their pharmaceutically acceptable salts.

The present invention therefore extends to compounds (2) to (26) and (28) to (79) as such, which pertain to the new compounds of formula (I) as defined above, and their pharmaceutically acceptable salts, such as hydrobromide, tartrate, citrate, trifluoroacetate, ascorbate, hydrochloride, tosylate, triflate, maleate, mesylate, formate, acetate and fumarate.

According to another aspect, a subject-matter of the present invention relates to a new compound of formula (I) as defined above or any of its pharmaceutically acceptable salts, or at least any of compounds (2) to (26) and (28) to (79), more preferably compounds 2 to 8, 10, 12 to 14, 16, 17, 20 to 23, 28, 29, 31, 32, 38 to 57, 63, 76 and 77 or any of its pharmaceutically acceptable salts, for use as a medicament.

According to another aspect, a subject-matter of the present invention relates to a compound of formula (I), as defined above or any of its pharmaceutically acceptable salts, or at least any of compounds (1) to (79), more preferably compounds 1 to 8, 10, 12 to 14, 16, 17, 20 to 23, 28, 29, 31, 32, 38 to 57, 63, 76 and 77, or any of its pharmaceutically acceptable salts, for use as an agent for preventing, inhibiting or treating a RNA virus infection caused by a RNA virus belonging to group IV or V of the Baltimore classification, preferably a RSV viral infection, a Chikungunya viral infection, a Dengue viral infection, and an Influenza viral infection, more particularly a RSV viral infection, a Chikungunya viral infection and a Dengue viral infection, and still more preferably a RSV viral infection.

The compounds of the invention may exist in the form of free bases or of addition salts with pharmaceutically acceptable acids.

«Pharmaceutically acceptable salt thereof» refers to salts which are formed from acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

Suitable physiologically acceptable acid addition salts of compounds of formula (I) include hydrobromide, tartrate, citrate, trifluoroacetate, ascorbate, hydrochloride, tosylate, triflate, maleate, mesylate, formate, acetate and fumarate.

The compounds of formula (I), and any of compounds (1) to (79) or any of their pharmaceutically acceptable salts may form solvates or hydrates and the invention includes all such solvates and hydrates.

The compounds of formula (I) may be present as well under tautomer forms and are part of the invention.

The terms "hydrates" and "solvates" simply mean that the compounds (I) according to the invention can be in the form of a hydrate or solvate, i.e. combined or associated with one or more water or solvent molecules. This is only a chemical characteristic of such compounds, which can be applied for all organic compounds of this type.

In the context of the present invention, the term:
"halogen" is understood to mean chlorine, fluorine, bromine, or iodine, and in particular denotes chlorine, fluorine or bromine,
"$(C_1-C_x)$alkyl", as used herein, respectively refers to a $C_1-C_x$ normal, secondary or tertiary saturated hydrocarbon, for example $(C_1-C_6)$alkyl. Examples are, but are not limited to, methyl, ethyl, 1-propyl, 2-propyl, butyl, pentyl, "($C_3$-$C_6$)cycloalkyl", as used herein, refers to a cyclic saturated hydrocarbon. Examples are, but are not limited to, cyclopropyl, cyclobutyl, cyclopentyl, cyclohexyl, "($C_3$-$C_6$)heterocycloalkyl group", as used herein, refers to a ($C_3$-$C_6$)cycloalkyl group wherein one or two of the carbon atoms are replaced with a heteroatom such as an oxygen or a nitrogen atom. Examples are, but are not limited to, morpholine, piperazine, piperidine, pyrrolidine, aziridine, oxetane, furane and dioxane.

"($C_1$-$C_x$)alkoxy", as used herein, refers to a O—($C_1$-$C_x$) alkyl moiety, wherein alkyl is as defined above, for example ($C_1$-$C_6$)alkoxy. Examples are, but are not limited to, methoxy, ethoxy, 1-propoxy, 2-propoxy, butoxy and pentoxy.

The compounds of formula (I) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

The compounds of the present invention can be prepared by conventional methods of organic synthesis practiced by those skilled in the art. The general reaction sequences outlined below represent a general method useful for preparing the compounds of the present invention and are not meant to be limiting in scope or utility.

The compounds of general formula (I) can be prepared according to scheme 1 below.

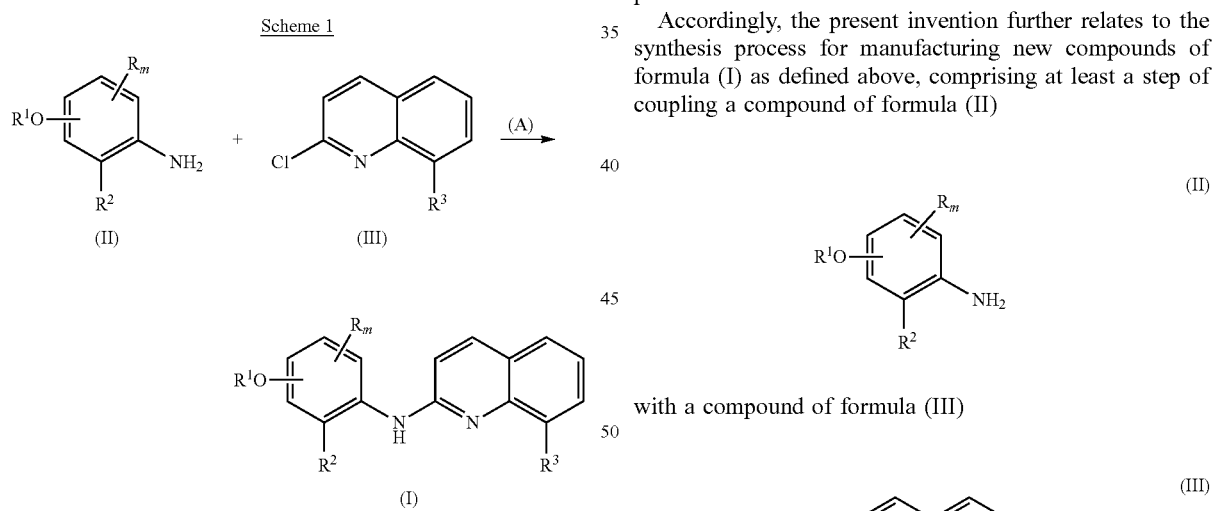

The synthesis is based on a coupling reaction starting from an amino aromatic compound of formula (II), wherein R, m, $R^1$ and $R^2$ are as defined above, and a chloro aromatic compound of formula (III), wherein $R^3$ is as defined above.

According to route (A), the compound of formula (III) may be placed in a protic solvent such as tert-butanol. The compound of formula (II) may then be added, for example in a molar ratio ranging from 1 to 1.5 with respect to the compound of formula (III) in presence of an inorganic base, such as $Cs_2CO_3$ or $K_2CO_3$, for example in a molar ratio ranging from 1 to 5, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in particular in an amount ranging from 2 mol % to 15 mol % relative to the total amount of compound of formula (III), and in the presence of an organometallic catalyst, such as Pd(OAc)$_2$ or Pd$_2$dba$_3$, in an amount ranging from 2 mol % to 25 mol % relative to the total amount of compound of formula (III). The reaction mixture can then be heated at a temperature ranging from 80 to 130° ° C., for example at 90° C., and stirred for a time ranging from 13 to 90 hours, for example during 24 hours, under inert gas and for example argon. The reaction mixture can be concentrated under reduced pressure and the residue can be diluted with an organic solvent such as ethyl acetate. The organic phase can be washed with water, decanted, dried over magnesium sulphate, filtered, concentrated under reduced pressure and then purified to give a compound of formula (I).

As an alternative method to follow route (A), the compound of formula (III) may be placed in an aprotic solvent such as anhydrous 1,4-dioxane. The compound of formula (II) may then be added, for example in a molar ratio ranging from 1 to 1.5 with respect to the compound of formula (III) in presence of an inorganic acid, such as hydrochloric acid (e.g. 4N HCl in 1,4-dioxane), for example in a molar ratio ranging from 2 to 7. The reaction mixture can then be heated under microwave irradiation at a temperature ranging from 100 to 190° C., for example at 170° C., and stirred for a time ranging from 10 to 120 minutes, for example during 45 minutes. The reaction mixture can be filtered, concentrated under reduced pressure and then purified to give a compound of formula (I).

The starting compounds of formula (II), (III) are available or can be prepared according to methods known to the person skilled in the art.

Accordingly, the present invention further relates to the synthesis process for manufacturing new compounds of formula (I) as defined above, comprising at least a step of coupling a compound of formula (II)

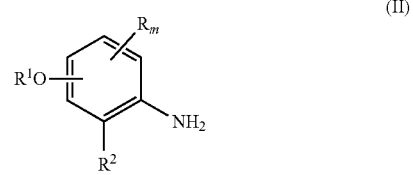

with a compound of formula (III)

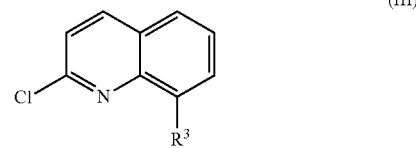

wherein $R^1$, $R^2$, $R^3$, R and m are as defined above, in presence of an inorganic base and a diphosphine and in the presence of an organometallic catalyst, to obtain a compound of formula (I).

More particularly, when $R^1$ represents an alkyl group and $R^2$ is different from H, compounds of formula (II), when used to prepare compounds of formula (I), can be prepared according to scheme 2 below.

Scheme 2

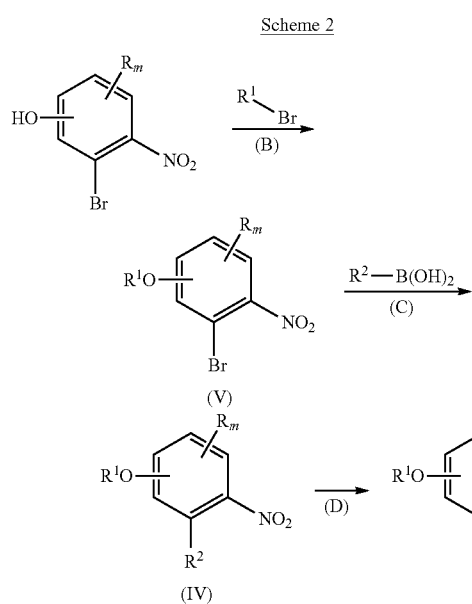

Intermediate compounds of formulae (II), (IV) and (V) are useful for preparing compounds of formula (I) according to the invention.

According to route (B), the 4-nitrophenol derivative may be placed in a polar solvent such as N,N-dimethylformamide. Bromo derivative $R^1Br$ may then be added in particular in a molar ratio ranging from 1 to 2 with respect to the 4-nitrophenol derivative in presence of an inorganic base, such as $Cs_2CO_3$ or $K_2CO_3$, in particular in a molar ratio ranging from 1 to 5. The reaction mixture can then be heated at a temperature ranging from 50 to 150° C., for example at 90° C. and stirred for a time ranging from 5 to 90 hours, for example during 14 hours, under inert gas and for example argon. The reaction mixture can be concentrated under reduced pressure and the residue can be partitioned between an organic solvent, such as dichloromethane, and water. The organic phase can be washed with water, decanted, dried over magnesium sulphate, filtered, concentrated under reduced pressure and purified to give a compound of formula (V).

According to route (C), the compound of formula (V) and an organometallic catalyst such as $Pd(dppf)Cl_2 \cdot CH_2Cl_2$, for example in an amount ranging from 2 mol % to 20 mol % relative to the amount of the compound of formula (V) may be placed in an apolar solvent such as 1,4-dioxane. A boronic acid $R^2$—$B(OH)_2$ may then be added in a molar ratio ranging from 1 to 5 with respect to the compound of formula (V), in presence of an inorganic base, such as $K_3PO_4$ or $K_2CO_3$, in particular in a molar ratio ranging from 2 to 5. The reaction mixture can then be heated at a temperature ranging from 50 to 150° C., for example at 100° C., and stirred for a time ranging from 10 to 70 hours, for example during 20 hours, under inert gas and for example argon. The reaction mixture can be concentrated under reduced pressure and purified to give a compound of formula (IV).

According to route (D), the compound of formula (IV) and tin (II) chloride dihydrate in a ratio ranging from 3 to 8 equivalents may be placed in a protic solvent such as ethanol. The reaction mixture can then be heated at a temperature ranging from 40 to 80° C., for example at 60° ° C. and stirred for a time ranging from 10 to 25 hours, for example during 14 hours. The mixture can be poured into 1N NaOH aqueous solution and extracted with an organic solvent such as ethyl acetate. The organic phase can then be washed with water and a saturated aqueous solution of brine, dried over magnesium sulphate, filtered, concentrated under reduced pressure and purified to give a compound of formula (II).

More particularly, when $R^1$ represents an aryl group and $R^2$ is different from H, compounds of formula (II), when used to prepare compounds of formula (I), can either be prepared according to scheme 3 or scheme 4 below.

Scheme 3

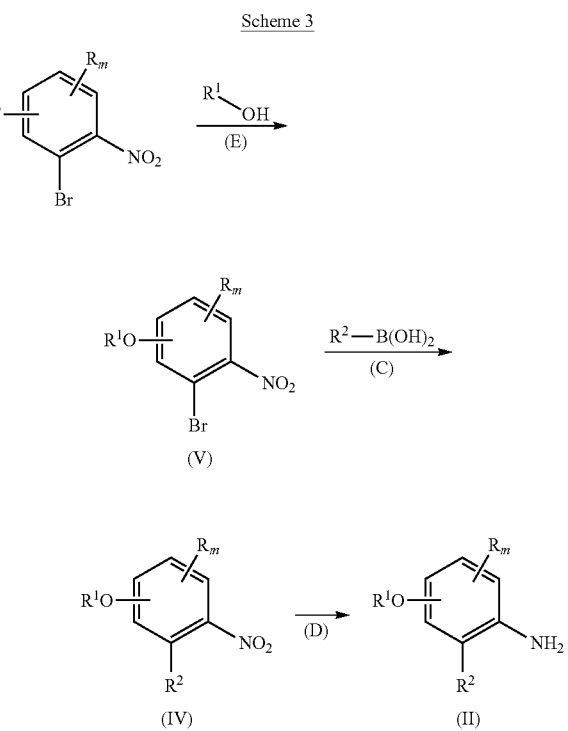

Intermediate compounds of formulae (II), (IV) and (V) are useful for preparing compounds of formula (I) according to the invention.

According to route (E), the 4-fluoronitrobenzene derivative may be placed in a polar solvent such as N,N-dimethylformamide. Phenol derivative $R^1OH$ may then be added in a molar ratio ranging from 1 to 2 with respect to the 4-fluoronitrobenzene derivative in presence of an inorganic base, such as $Cs_2CO_3$ or $K_2CO_3$, in particular in a molar ratio ranging from 1 to 5. The reaction mixture can then be heated at a temperature ranging from 50 to 150° C., for example at 70° C. and stirred for a time ranging from 5 to 90 hours, for example during 16 hours, under inert gas and for example argon. The reaction mixture can be concentrated under reduced pressure and the residue can be partitioned between an organic solvent, such as dichloromethane, and water. The organic phase can be washed with water, decanted, dried over magnesium sulphate, filtered, concentrated under reduced pressure and purified to give a compound of formula (V).

According to route (C), the compound of formula (V) and an organometallic catalyst such as $Pd(dppf)Cl_2 \cdot CH_2Cl_2$ in an amount ranging from 2 mol % to 20 mol % relative to the amount of the compound of formula (V) may be placed in an apolar solvent such as 1,4-dioxane. A boronic acid $R^2$—$B(OH)_2$ may then be added in a molar ratio ranging from 1 to 5 with respect to the compound of formula (V), in presence of an inorganic base, such as $K_3PO_4$ or $K_2CO_3$, in particular in a molar ratio ranging from 2 to 5. The reaction mixture can then be heated at a temperature ranging from 50 to 150° C., for example at 100° C., and stirred for a time ranging from 10 to 70 hours, for example during 20 hours, under inert gas and for example argon. The reaction mixture can be concentrated under reduced pressure and purified to give a compound of formula (IV).

According to route (D), the compound of formula (IV) and tin (II) chloride dihydrate in a ratio ranging from 3 to 8 equivalents may be placed in a protic solvent such as ethanol. The reaction mixture can then be heated at a temperature ranging from 40 to 80° C., for example at 60° C. and stirred for a time ranging from 10 to 25 hours, for example during 14 hours. The mixture can be poured into 1N NaOH aqueous solution and extracted with an organic solvent such as ethyl acetate. The organic phase can then be washed with water and a saturated aqueous solution of brine, dried over magnesium sulphate, filtered, concentrated under reduced pressure and purified to give a compound of formula (II).

Scheme 4 (illustrated with $R^2$ = Me)

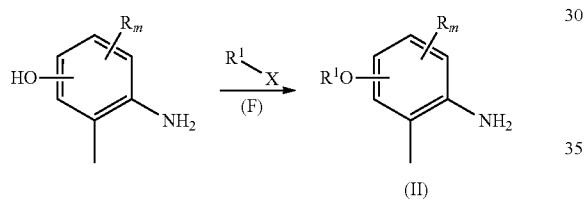

Intermediate compounds of formula (II) are useful for preparing compounds of formula (I) according to the invention.

According to route (F), the halogenoaryl derivative $R^1X$ may be placed in an apolar solvent such as toluene. The phenol derivative may then be added in a molar ratio ranging from 1 to 2 with respect to the halogenoaryl derivative in presence of an inorganic base, such as $Cs_2CO_3$ or $K_2CO_3$, in particular in a molar ratio ranging from 1 to 3, in the presence of a ligand, such as 1-methylimidazole in particular in an amount ranging from 5 mol % to 30 mol % relative to the total amount of compound $R^1X$, and in the presence of a copper catalyst, such as CuCl or CuI, in an amount ranging from 2 mol % to 15 mol % relative to the total amount of compound RlX. The reaction mixture can then be heated at a temperature ranging from 50 to 150° C., for example at 130° ° C. and stirred for a time ranging from 5 to 25 hours, for example during 16 hours, under inert gas and for example argon. The reaction mixture can be filtered over a pad of celite. The filtrate can be concentrated under reduced pressure and the residue can be purified to give a compound of formula (II).

The chemical structures and spectroscopic data of some compounds of formula (I) of the invention are illustrated respectively in the following Table I and Table II.

TABLE I

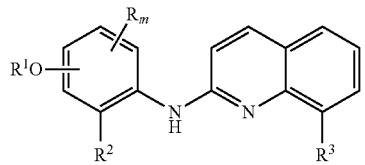

| | |
|---|---|
| 1 | 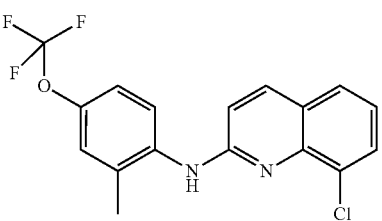 [SMILES: Cc1cc(OC(F)(F)F)ccc1Nc1ccc2cccc(Cl)c2n1] |
| 2 | 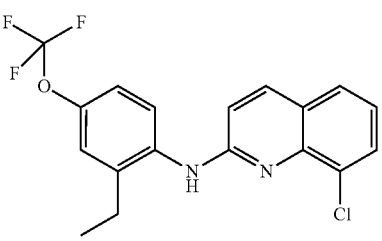 [SMILES: CCc1cc(OC(F)(F)F)ccc1Nc1ccc2cccc(Cl)c2n1] |
| 3 | 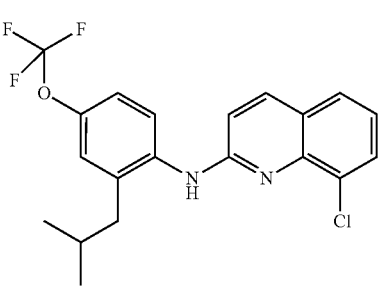 [SMILES: CC(C)Cc1cc(OC(F)(F)F)ccc1Nc1ccc2cccc(Cl)c2n1] |
| 4 | 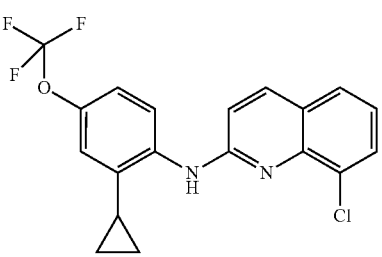 [SMILES: FC(F)(F)Oc1ccc(Nc2ccc3cccc(Cl)c3n2)c(C2CC2)c1] |
| 5 | 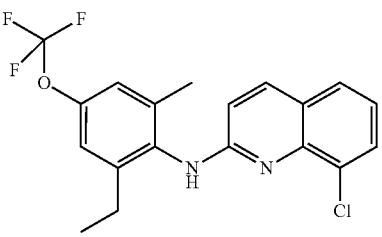 [SMILES: CCc1cc(OC(F)(F)F)cc(C)c1Nc1ccc2cccc(Cl)c2n1] |

TABLE I-continued
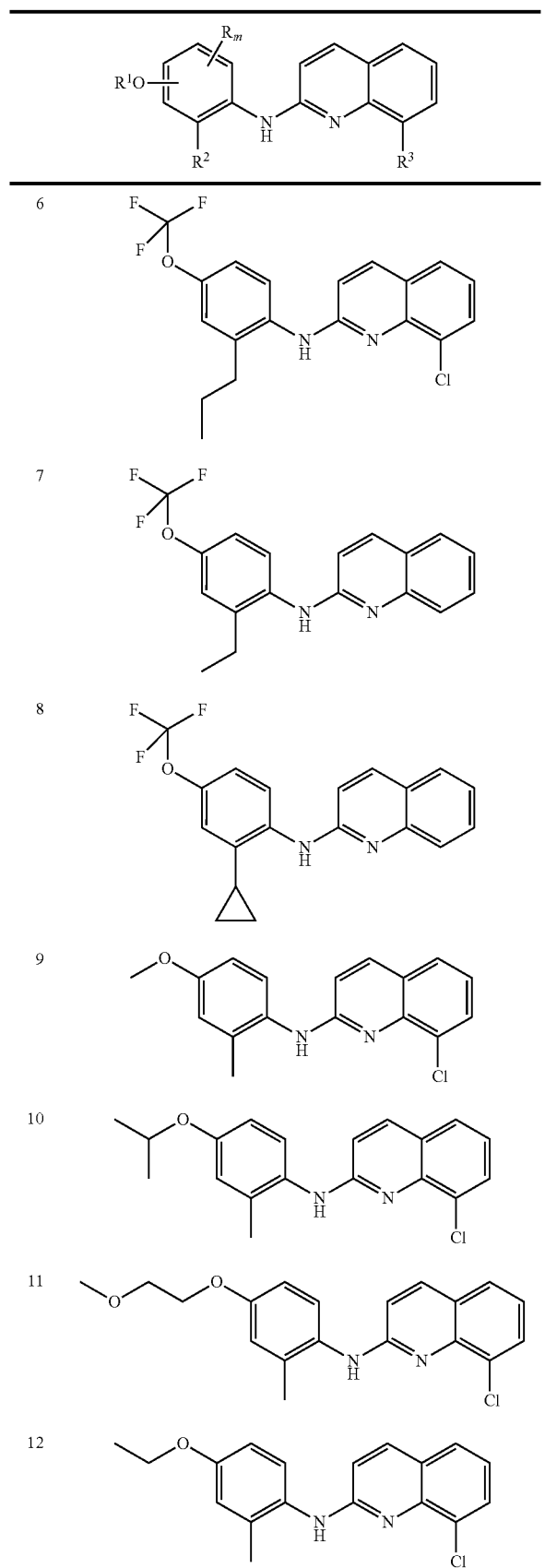
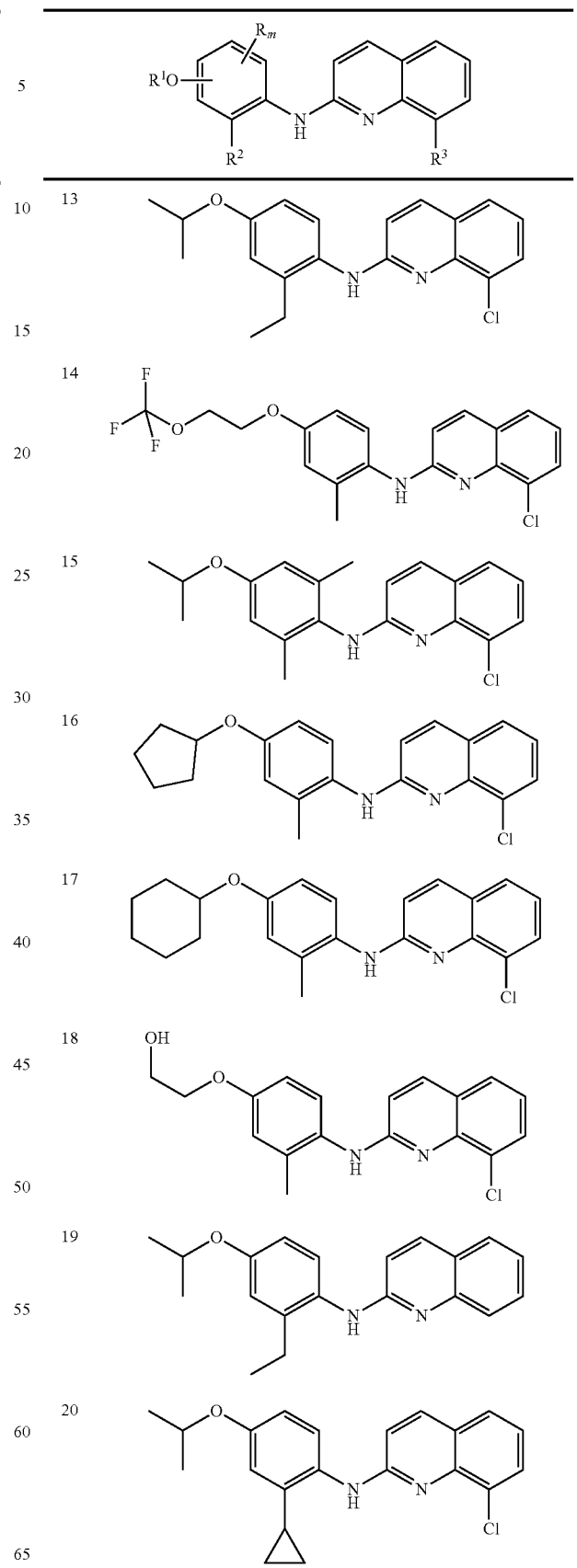

TABLE I-continued
| | | |
|---|---|---|
| 21 | 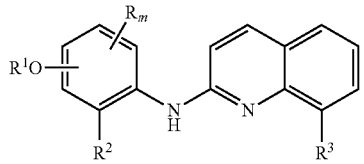 | |
| 22 | 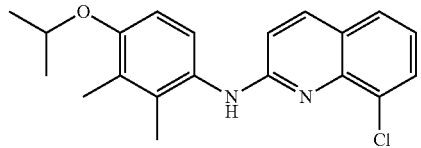 [SMILES: Cc1c(Nc2ccc3cccc(Cl)c3n2)ccc(OC(C)C)c1C] | |
| 23 | 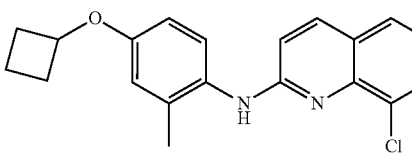 | |
| 24 | 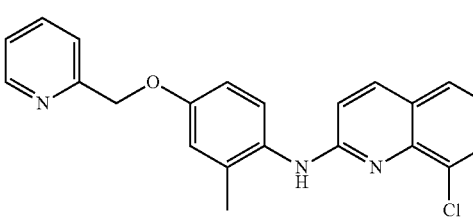 | |
| 25 | 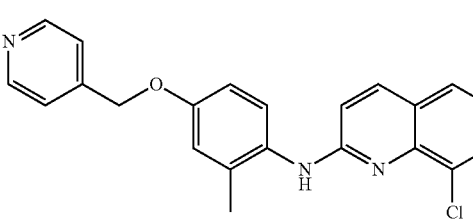 | |
| 26 | 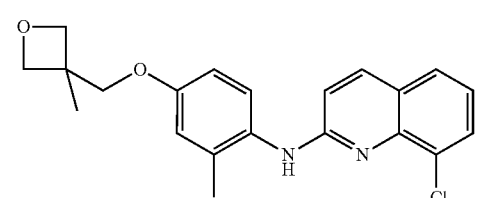 | |
| 27 | 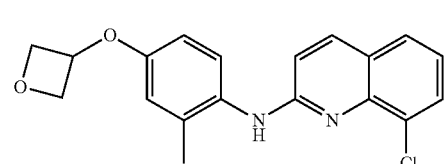 | |
| 28 | 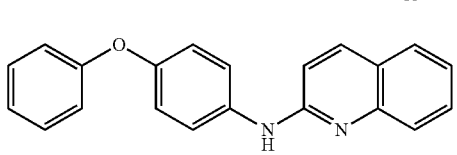 [SMILES: c1ccc(Oc2ccc(Nc3ccc4ccccc4n3)cc2)cc1] | |
| 29 | 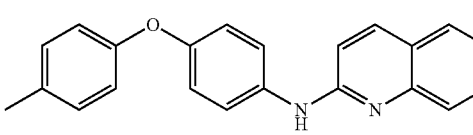 | |
| 30 | 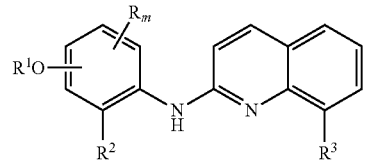 | |
| 31 | 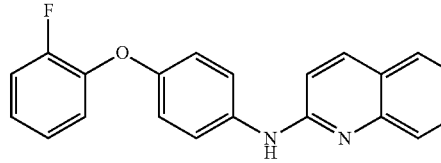 | |
| 32 | 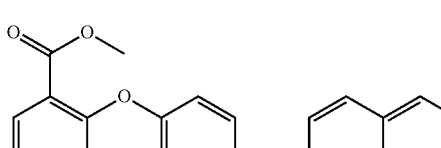 | |
| 33 | 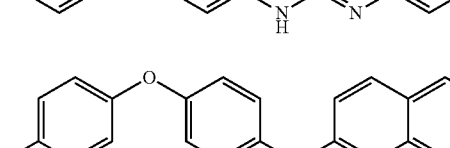 | |
| 34 | 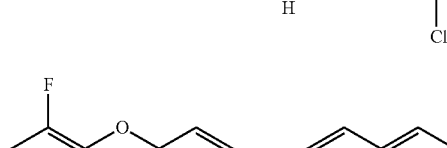 | |
| 35 | 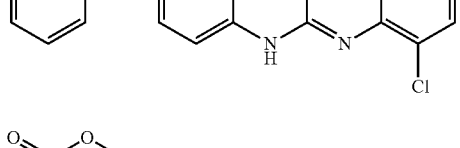 | |
| 36 | 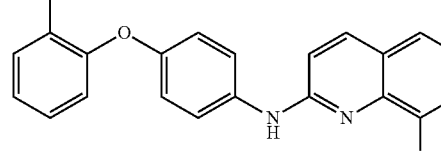 | |

TABLE I-continued
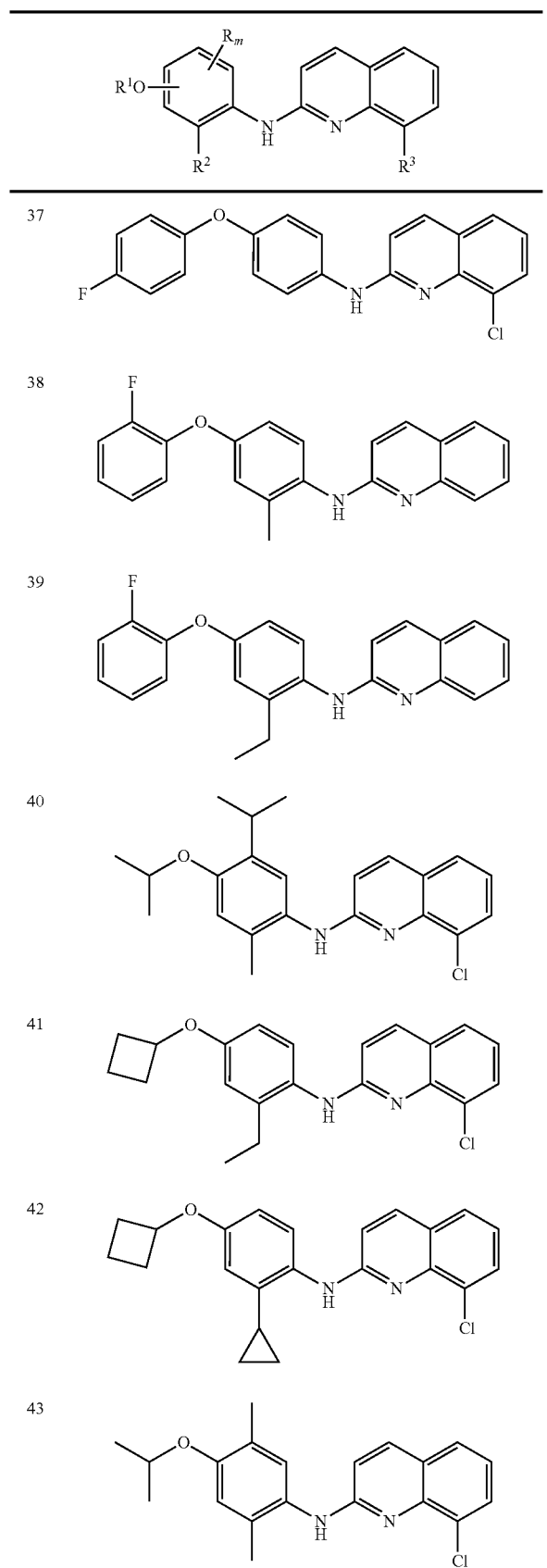
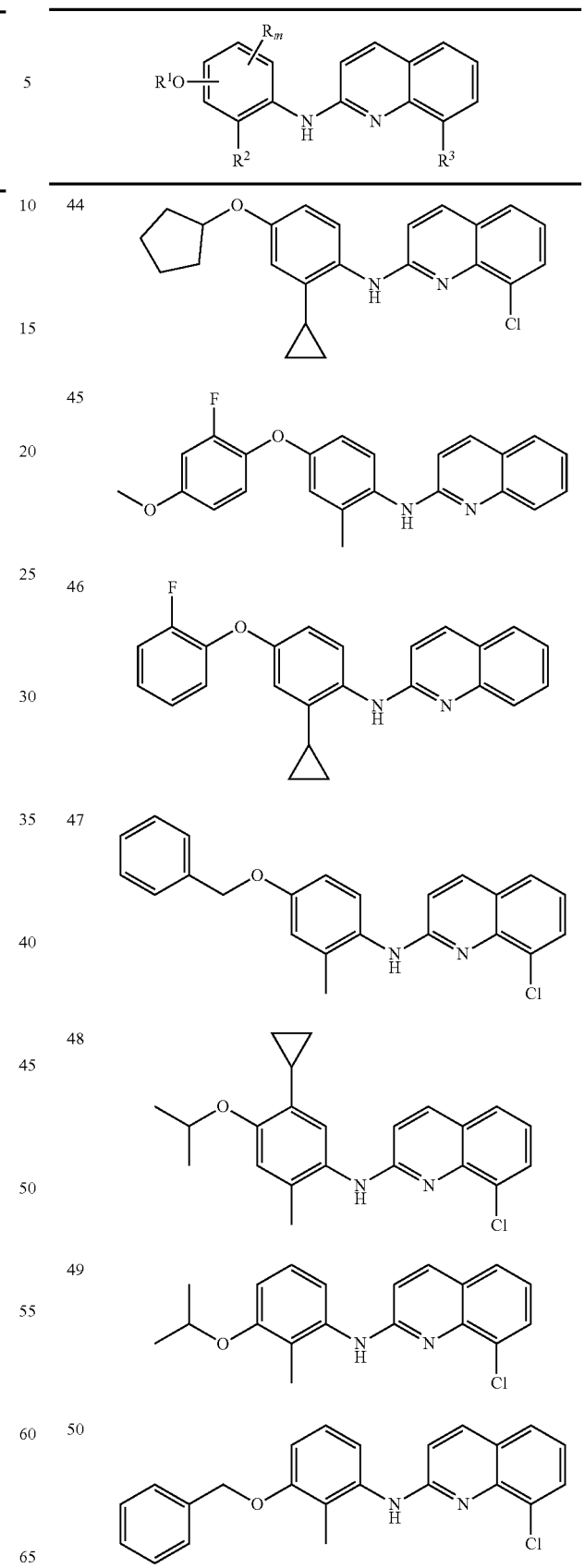

TABLE I-continued

[Structure header: R¹O-phenyl(Rm)(R²)-NH-quinoline(R³)]

| # | Structure |
|---|---|
| 51 | 4-methoxyphenoxy / 3-methyl-phenyl-NH-quinoline |
| 52 | 2-fluoro-4-methoxyphenoxy / cyclopropyl-phenyl-NH-quinoline |
| 53 | 3-fluoro-4-hydroxyphenoxy / methyl-phenyl-NH-quinoline |
| 54 | 1-naphthyloxy / methyl-phenyl-NH-(8-chloroquinoline) |
| 55 | phenoxy / methyl-phenyl-NH-(8-chloroquinoline) |
| 56 | phenoxy / methyl-phenyl-NH-(8-chloroquinoline) · CF₃CO₂H |
| 57 | 2-naphthyloxy / methyl-phenyl-NH-(8-chloroquinoline) |
| 58 | phenoxy / methyl-phenyl-NH-quinoline |
| 59 | pyridin-3-ylmethoxy / methyl-phenyl-NH-(8-chloroquinoline) |
| 60 | phenoxy / phenyl-NH-(8-chloroquinoline) |
| 61 | phenoxy / methyl-phenyl-NH-(8-chloroquinoline) |
| 62 | phenoxy / phenyl-NH-(8-chloroquinoline) |
| 63 | 2-fluorophenoxy / dimethyl-phenyl-NH-(8-chloroquinoline) · CF₃CO₂H |
| 64 | phenoxy / dimethyl-phenyl-NH-(8-chloroquinoline) |
| 65 | isopropoxy / dimethyl-phenyl-NH-quinoline |

TABLE I-continued
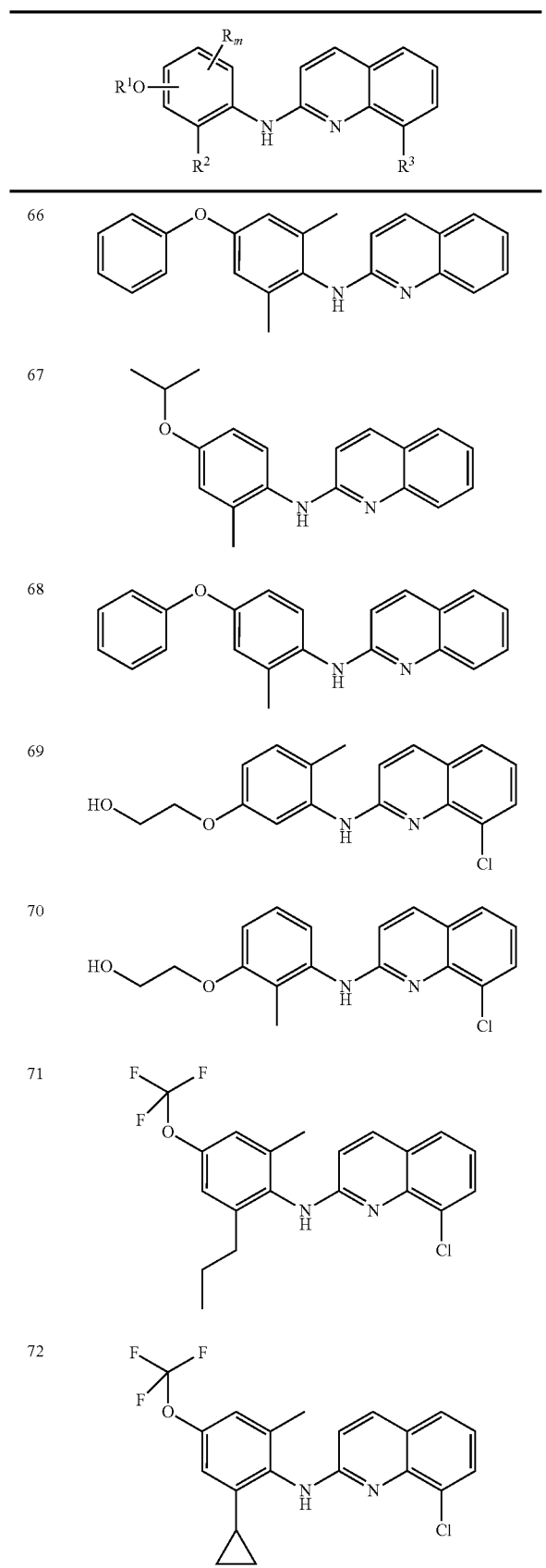
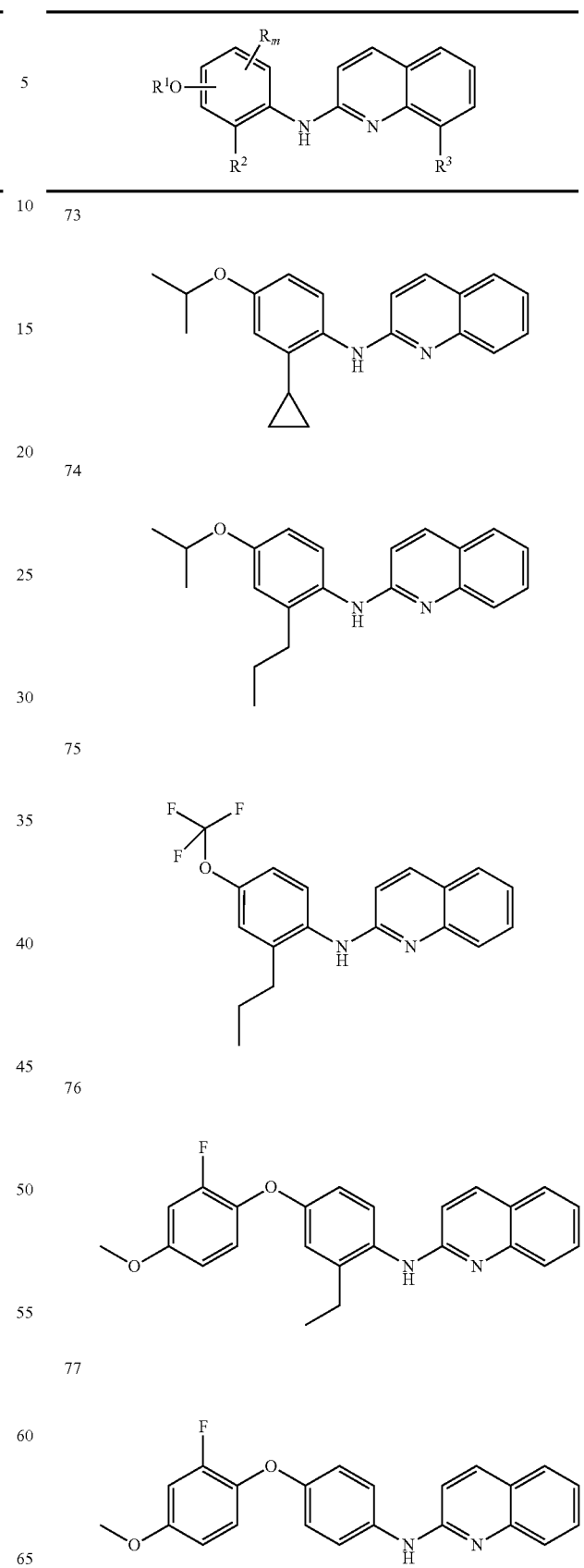

TABLE I-continued

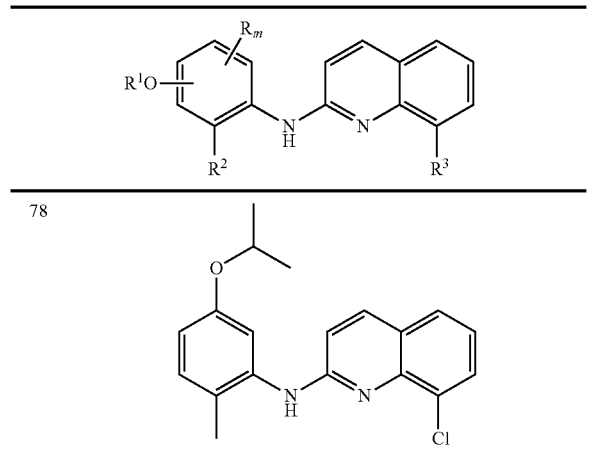

| | |
|---|---|
| 78 | (structure shown) |
| 79 | (structure shown) |

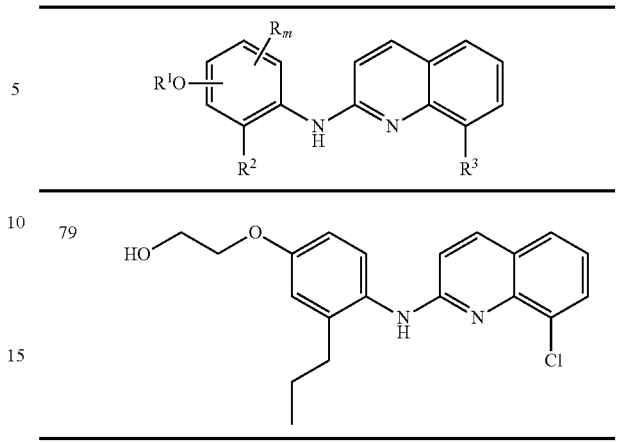

TABLE II

| Ex | Characterizations |
|---|---|
| 1 | $^1$H NMR (300 MHz, CDCl$_3$) δ 8.10 (d, J = 9.0 Hz, 1H), 7.94 (d, J = 8.9 Hz, 1H), 7.74 (dd, J = 8.0, 1.2 Hz, 1H), 7.59 (d, J = 8.0 Hz, 1H), 7.23 (t, J = 8.0 Hz, 1H), 7.19-7.10 (m, 2H), 6.87 (d, J = 8.9 Hz, 1H), 6.71 (s, 1H), 2.37 (s, 3H). |
| 2 | $^1$H NMR (300 MHz, CDCl$_3$) δ 7.96 (d, J = 9.0 Hz, 1H), 7.91 (d, J = 9.0 Hz, 1H), 7.72 (dd, J = 8.0, 1.0 Hz, 1H), 7.57 (dd, J = 8.0, 1.0 Hz, 1H), 7.21 (t, J = 8.0 Hz, 1H), 7.15-7.13 (m, 2H), 6.83 (d, J = 9.0 Hz, 1H), 6.74 (s, 1H), 2.71 (q, J = 7.5 Hz, 2H), 1.26 (t, J = 7.5 Hz, 3H).<br>$^{13}$C NMR (75 MHz, CDCl$_3$) δ 153.1, 143.7, 141.6, 136.3, 136.0, 133.5, 127.9, 127.6, 124.1, 122.9, 122.3, 120.5, 119.1, 116.9, 109.2, 22.0, 11.4<br>[M + H]$^+$ = 367.2 |
| 3 | $^1$H NMR (300 MHz, CDCl$_3$) δ 7.95 (d, J = 9.0 Hz, 1H), 7.90 (d, J = 9.0 Hz, 1H), 7.72 (dd, J = 8.0, 1.0 Hz, 1H), 7.57 (dd, J = 8.0, 1.0 Hz, 1H), 7.21 (t, J = 8.0 Hz, 1H), 7.15 (s, 1H), 7.11 (d, J = 5.1 Hz, 2H), 6.82 (d, J = 9.0 Hz, 1H), 6.71 (s, 1H), 2.56 (d, J = 7.3 Hz, 2H), 1.99-1.88 (m, 1H), 0.95 (d, J = 6.6 Hz, 6H).<br>[M + H]$^+$ = 394.9 |
| 4 | $^1$H NMR (300 MHz, CDCl$_3$) δ 8.73 (d, J = 9.0 Hz, 1H), 7.95 (d, J = 9.0 Hz, 1H), 7.74 (dd, J = 8.0, 1.2 Hz, 1H), 7.58 (dd, J = 8.0, 1.2 Hz, 1H), 7.35 (s, 1H), 7.22 (d, J = 8.0 Hz, 1H), 7.17 (d, J = 2.0 Hz, 1H), 7.01 (d, J = 2.0 Hz, 1H), 6.92 (d, J = 9.0 Hz, 1H), 1.91 (tt, J = 8.3, 5.4 Hz, 1H), 1.07 (q, J = 4.3 Hz, 2H), 0.74 (q, J = 4.3 Hz, 2H).<br>$^{13}$C NMR (75 MHz, CDCl$_3$) δ 152.1, 142.2, 141.8, 136.2, 136.0, 131.4, 128.8, 127.9, 124.3, 123.2, 121.1, 118.9, 118.8, 117.8, 117.6, 111.2, 9.5, 4.4<br>[M + H]$^+$ = 379.1 |
| 5 | $^1$H NMR (300 MHz, CDCl$_3$) δ 7.84 (d, J = 8.8 Hz, 1H), 7.71 (d, J = 6.3 Hz, 1H), 7.55 (d, J = 7.5 Hz, 1H), 7.18 (t, J = 7.5 Hz, 1H), 7.06 (s, 2H), 6.65 (s, 1H), 6.34 (d, J = 8.8 Hz, 1H), 2.66 (q, J = 7.5 Hz, 2H), 2.26 (s, 3H), 1.15 (t, J = 7.5 Hz, 3H). |
| 6 | $^1$H NMR (300 MHz, CDCl$_3$) δ 7.93 (d, J = 4.0 Hz, 1H), 7.90 (d, J = 4.0 Hz, 1H), 7.72 (dd, J = 8.0, 1.0 Hz, 1H), 7.57 (d, J = 8.0 Hz, 1H), 7.21 (t, J = 8.0 Hz, 1H), 7.14 (s, 2H), 6.83 (d, J = 8.9 Hz, 1H), 6.74 (s, 1H), 2.73-2.57 (m, 2H), 1.73-1.66 (m, 2H), 0.98 (t, J = 7.3 Hz, 3H).<br>[M + H]$^+$ = 380.9 |
| 7 | $^1$H NMR (300 MHz, CDCl$_3$) δ 7.90 (d, J = 8.9 Hz, 1H), 7.70 (d, J = 7.3 Hz, 1H), 7.64 (m, 2H), 7.57 (t, J = 8.0 Hz, 1H), 7.28 (t, J = 8.0 Hz, 1H), 7.17-7.08 (m, 2H), 6.80 (d, J = 8.9 Hz, 1H), 2.67 (q, J = 7.5 Hz, 2H), 1.22 (t, J = 7.5 Hz, 3H).<br>[M + H]$^+$ = 333.0 |
| 8 | $^1$H NMR (300 MHz, CDCl$_3$) δ 8.20 (d, J = 8.9 Hz, 1H), 7.95 (d, J = 8.9 Hz, 1H), 7.80 (d, J = 8.4 Hz, 1H), 7.66 (d, J = 8.0 Hz, 1H), 7.61 (ddd, J = 8.4, 7.0, 1.6 Hz, 1H), 7.36-7.29 (m, 1H), 7.13 (dd, J = 8.9, 1.6 Hz, 1H), 7.07 (s, 1H), 6.98 (d, J = 2.5 Hz, 1H), 6.94 (d, J = 8.9 Hz, 1H), 1.91 (tt, J = 8.4, 5.4 Hz, 1H), 1.04 (q, J = 4.3 Hz, 2H), 0.72 (q, J = 4.4 Hz, 2H).<br>$^{13}$C NMR (75 MHz, CDCl$_3$) δ 151.7, 145.1, 141.9, 136.0, 135.4, 132.2, 127.5, 125.0, 124.3, 121.8, 120.9, 118.8, 118.2, 117.1, 109.5, 9.2, 4.1<br>[M + H]$^+$ = 345.2 |
| 9 | $^1$H NMR (300 MHz, CDCl$_3$) δ 7.83 (d, J = 9.0 Hz, 1H), 7.69 (dd, J = 8.0, 1.2 Hz, 1H), 7.53 (dd, J = 8.0, 1.2 Hz, 1H), 7.42 (d, J = 8.5 Hz, 1H), 7.16 (t, J = 8.0 Hz, 1H), 6.85 (d, J = 2.7 Hz, 1H), 6.80 (dd, J = 8.5, 2.7 Hz, 1H), 6.72 (s, 1H), 6.67 (d, J = 9.0 Hz, 1H), 3.83 (s, 3H), 2.29 (s, 3H). |
| 10 | $^1$H NMR (300 MHz, CDCl$_3$) δ 7.81 (d, J = 9.0 Hz, 1H), 7.67 (dd, J = 8.0, 1.2 Hz, 1H), 7.51 (dd, J = 8.0, 1.2 Hz, 1H), 7.39 (d, J = 8.5 Hz, 1H), 7.13 (t, J = 8.0 Hz, 1H), 6.83 (d, J = 2.7 Hz, 1H), 6.77 (dd, J = 8.5, 2.7 Hz, 2H), 6.67 (d, J = 9.0 Hz, 1H), 4.62-4.46 (m, 1H), 2.25 (s, 3H), 1.35 (d, J = 6.1 Hz, 6H).<br>[M + H]$^+$ = 327.0 |
| 11 | $^1$H NMR (300 MHz, CDCl$_3$) δ 7.83 (d, J = 9.0 Hz, 1H), 7.68 (dd, J = 8.0, 1.2 Hz, 1H), 7.53 (dd, J = 8.0, 1.2 Hz, 1H), 7.42 (d, J = 8.5 Hz, 1H), 7.15 (t, J = 8.0 Hz, 1H), 6.88 (d, J = 2.7 Hz, 1H), 6.82 (dd, J = 8.5, 2.7 Hz, 1H), 6.71 (s, 1H), 6.66 (d, J = 9.0 Hz, 1H), 4.18-4.08 (m, 2H), 3.81-3.72 (m, 2H), 3.47 (s, 3H), 2.27 (s, 3H).<br>[M + H]$^+$ = 343.0 |

TABLE II-continued

| Ex | Characterizations |
|---|---|
| 12 | ¹H NMR (300 MHz, CDCl₃) δ 7.83 (d, J = 9.0 Hz, 1H), 7.69 (dd, J = 8.0, 1.2 Hz, 1H), 7.53 (dd, J = 8.0, 1.2 Hz, 1H), 7.41 (d, J = 8.5 Hz, 1H), 7.16 (t, J = 8.0 Hz, 1H), 6.85 (d, J = 2.7 Hz, 1H), 6.79 (dd, J = 8.5, 2.7 Hz, 1H), 6.73 (s, 1H), 6.67 (d, J = 9.0 Hz, 1H), 4.06 (q, J = 7.0 Hz, 2H), 2.28 (s, 3H), 1.44 (t, J = 7.0 Hz, 3H). |
| 13 | ¹H NMR (300 MHz, CDCl₃) δ 7.82 (d, J = 9.0 Hz, 1H), 7.70 (dd, J = 8.0, 1.0 Hz, 1H), 7.53 (dd, J = 8.0, 1.0 Hz, 1H), 7.34 (d, J = 8.5 Hz, 1H), 7.16 (t, J = 8.0 Hz, 1H), 6.87 (d, J = 2.7 Hz, 1H), 6.78 (dd, J = 8.5, 2.7 Hz, 1H), 6.71 (s, 1H), 6.67 (d, J = 9.0 Hz, 1H), 4.57 (dt, J = 12.1, 6.1 Hz, 1H), 2.65 (q, J = 7.5 Hz, 2H), 1.38 (d, J = 6.1 Hz, 6H), 1.19 (t, J = 7.5 Hz, 3H). |
| 14 | ¹H NMR (300 MHz, CDCl₃) δ 7.86 (d, J = 9.0 Hz, 1H), 7.70 (dd, J = 8.0, 1.2 Hz, 1H), 7.59-7.48 (m, 2H), 7.17 (t, J = 8.0 Hz, 1H), 6.88 (d, J = 2.7 Hz, 1H), 6.82 (dd, J = 8.5, 2.7 Hz, 1H), 6.75 - 6.61 (m, 2H), 4.32 (dd, J = 5.7, 3.1 Hz, 2H), 4.27-4.16 (m, 2H), 2.30 (s, 3H). |
| 15 | ¹H NMR (300 MHz, CDCl₃) δ 7.79 (d, J = 9.0 Hz, 1H), 7.69 (dd, J = 8.0, 1.2 Hz, 1H), 7.52 (dd, J = 8.0, 1.2 Hz, 1H), 7.13 (t, J = 8.0 Hz, 1H), 6.70 (s, 2H), 6.57 (s, 1H), 6.34 (d, J = 9.0 Hz, 1H), 4.56 (dt, J = 12.2, 6.1 Hz, 1H), 2.21 (s, 6H), 1.36 (d, J = 6.1 Hz, 6H). [M + H]⁺ = 341.0 |
| 16 | ¹H NMR (300 MHz, CDCl₃) δ 7.83 (d, J = 9.0 Hz, 1H), 7.69 (dd, J = 8.0, 1.0 Hz, 1H), 7.53 (dd, J = 8.0, 1.0 Hz, 1H), 7.37 (d, J = 8.5 Hz, 1H), 7.15 (t, J = 8.0 Hz, 1H), 6.82 (d, J = 2.7 Hz, 1H), 6.76 (dd, J = 8.5, 2.7 Hz, 1H), 6.72 (s, 1H), 6.67 (d, J = 9.0 Hz, 1H), 4.85-4.72 (m, 1H), 2.26 (s, 3H), 1.97-1.75 (m, 8H). [M + H]⁺ = 353.0 |
| 17 | ¹H NMR (300 MHz, CDCl₃) δ 7.83 (d, J = 9.0 Hz, 1H), 7.69 (dd, J = 8.0, 1.0 Hz, 1H), 7.53 (dd, J = 8.0, 1.0 Hz, 1H), 7.38 (d, J = 8.5 Hz, 1H), 7.15 (t, J = 8.0 Hz, 1H), 6.85 (d, J = 2.7 Hz, 1H), 6.79 (dd, J = 8.5, 2.7 Hz, 1H), 6.73 (s, 1H), 6.68 (d, J = 9.0 Hz, 1H), 4.30-4.19 (m, 1H), 2.27 (s, 3H), 2.09-1.98 (m, 2H), 1.83 (dd, J = 6.1, 4.4 Hz, 2H), 1.52-1.32 (m, 5H). |
| 18 | ¹H NMR (300 MHz, CDCl₃) δ 7.84 (d, J = 9.0 Hz, 1H), 7.70 (dd, J = 8.0, 1.0 Hz, 1H), 7.54 (dd, J = 8.0, 1.0 Hz, 1H), 7.42 (d, J = 8.5 Hz, 1H), 7.17 (t, J = 8.0 Hz, 1H), 6.85 (d, J = 2.7 Hz, 1H), 6.80 (dd, J = 8.5, 2.7 Hz, 1H), 6.69 (d, J = 9.0 Hz, 1H), 4.15-4.11 (m, 2H), 4.04-4.01 (m, 2H), 2.27 (s, 3H). |
| 19 | ¹H NMR (300 MHz, CDCl₃) δ 7.83 (d, J = 9.0 Hz, 1H), 7.69 (dd, J = 8.0, 1.0 Hz, 1H), 7.61 (dd, J = 8.0, 1.0 Hz, 1H), 7.55 (d, J = 7.2 Hz, 1H), 7.30-7.25 (m, 3H), 6.86 (d, J = 2.7 Hz, 1H), 6.77 (dd, J = 8.5, 2.7 Hz, 1H), 6.66 (d, J = 9.0 Hz, 1H), 6.46 (s, 1H), 4.64-4.49 (m, 1H), 2.63 (q, J = 7.5 Hz, 2H), 1.37 (d, J = 6.0 Hz, 6H), 1.18 (t, J = 7.5 Hz, 3H). |
| 20 | ¹H NMR (300 MHz, CDCl₃) δ 7.85 (d, J = 9.0 Hz, 1H), 7.77 (d, J = 9.0 Hz, 1H), 7.69 (dd, J = 8.0, 1.2 Hz, 1H), 7.53 (dd, J = 8.0, 1.2 Hz, 1H), 7.16 (t, J = 8.0 Hz, 1H), 7.05 (s, 1H), 6.79 (dd, J = 9.0, 4.1 Hz, 2H), 6.58 (d, J = 2.7 Hz, 1H), 4.53 (hept, J = 6.1 Hz, 1H), 2.02-1.93 (m, 1H), 1.34 (d, J = 6.1 Hz, 6H), 0.94 (q, J = 4.3 Hz, 2H), 0.68 (q, J = 4.3 Hz, 2H). ¹³C NMR (75 MHz, CDCl₃) δ 154.1, 153.0, 141.9, 135.5, 129.1, 127.5, 127.4, 124.1, 122.9, 122.6, 119.8, 117.3, 112.0, 110.8, 109.3, 67.7, 19.7, 9.1, 5.2 [M + H]⁺ = 353.2 |
| 21 | ¹H NMR (300 MHz, CDCl₃) δ 7.79 (d, J = 9.0 Hz, 1H), 7.67 (dd, J = 8.0, 1.0 Hz, 1H), 7.51 (dd, J = 8.0, 1.0 Hz, 1H), 7.17 (d, J = 8.7 Hz, 1H), 7.11 (d, J = 8.0 Hz, 1H), 6.81 (s, 1H), 6.77 (d, J = 8.7 Hz, 1H), 6.60 (d, J = 9.0 Hz, 1H), 4.59-4.42 (m, 1H), 2.20 (s, 6H), 1.36 (d, J = 6.0 Hz, 6H). |
| 22 | ¹H NMR (300 MHz, CDCl₃) δ 7.82 (d, J = 8.6 Hz, 1H), 7.68 (dd, J = 8.0, 1.2 Hz, 1H), 7.52 (dd, J = 8.0, 1.2 Hz, 1H), 7.38 (d, J = 8.6 Hz, 1H), 7.15 (t, J = 7.8 Hz, 1H), 6.76 (d, J = 2.8 Hz, 1H), 6.71 (s, 1H), 6.68 (t, J = 7.8 Hz, 2H), 4.64 (p, J = 7.0 Hz, 1H), 2.53-2.40 (m, 2H), 2.26 (s, 3H), 2.23-2.10 (m, 2H), 1.95-1.80 (m, 1H), 1.71 (tt, J = 10.2, 5.2 Hz, 1H). ¹³C NMR (75 MHz, CDCl₃) δ 154.7, 153.4, 141.9, 135.9, 133.3, 127.8, 127.5, 127.3, 124.9, 124.2, 122.6, 119.8, 115.0, 110.7, 108.2, 69.2, 28.4, 16.1, 10.9 |
| 23 | ¹H NMR (300 MHz, CDCl₃) δ 8.62 (d, J = 4.3 Hz, 1H), 7.84 (d, J = 9.0 Hz, 1H), 7.74 (dd, J = 7.7, 1.2 Hz, 1H), 7.69 (dd, J = 7.7, 1.2 Hz, 1H), 7.58-7.51 (m, 1H), 7.45 (d, J = 8.6 Hz, 2H), 7.28-7.22 (m, 1H), 7.16 (t, J = 7.8 Hz, 1H), 6.95 (d, J = 2.8 Hz, 1H), 6.88 (dd, J = 8.6, 2.8 Hz, 1H), 6.68 (d, J = 9.0 Hz, 2H), 5.23 (s, 2H), 2.28 (s, 3H). |
| 24 | ¹H NMR (300 MHz, CDCl₃) δ 8.63 (d, J = 5.9 Hz, 2H), 7.84 (d, J = 9.0 Hz, 1H), 7.69 (dd, J = 7.6, 1.2 Hz, 1H), 7.53 (d, J = 8.5 Hz, 2H), 7.37 (d, J = 5.9 Hz, 2H), 7.16 (t, J = 7.8 Hz, 1H), 6.91 (d, J = 2.9 Hz, 1H), 6.84 (dd, J = 8.5, 2.9 Hz, 1H), 6.76 (s, 1H), 6.70 (d, J = 9.0 Hz, 1H), 5.11 (s, 2H), 2.29 (s, 3H). |
| 25 | ¹H NMR (300 MHz, CDCl₃) δ 7.84 (d, J = 9.0 Hz, 1H), 7.69 (dd, J = 8.0, 1.2 Hz, 1H), 7.53 (dd, J = 8.0, 1.2 Hz, 1H), 7.46 (d, J = 8.6 Hz, 1H), 7.16 (t, J = 8.0 Hz, 1H), 6.89 (d, J = 2.8 Hz, 1H), 6.83 (dd, J = 8.6, 2.8 Hz, 1H), 6.73 (s, 1H), 6.68 (d, J = 9.0 Hz, 1H), 4.65 (d, J = 5.9 Hz, 2H), 4.48 (d, J = 5.9 Hz, 2H), 4.04 (s, 2H), 2.29 (s, 3H), 1.46 (s, 3H). [M + H]⁺ = 369.3 |
| 26 | ¹H NMR (300 MHz, CDCl₃) δ 7.85 (d, J = 9.0 Hz, 1H), 7.69 (dd, J = 8.0, 1.2 Hz, 1H), 7.56-7.47 (m, 2H), 7.17 (t, J = 8.0 Hz, 1H), 6.70-6.66 (m, 3H), 6.57 (dd, J = 8.6, 2.9 Hz, 1H), 5.26-5.17 (m, 1H), 4.99 (t, J = 6.8 Hz, 2H), 4.79 (t, J = 6.8 Hz, 2H), 2.28 (s, 3H). ¹³C NMR (75 MHz, CDCl₃) δ 156.7, 154.6, 144.4, 138.4, 135.5, 131.5, 130.1, 130.0, 127.0, 126.7, 125.2, 122.5, 119.8, 117.2, 112.6, 111.0, 78.2, 77.6, 77.2, 76.7, 70.4, 18.6 [M + H]⁺ = 341.2 |
| 27 | ¹H NMR (300 MHz, CDCl₃) δ 7.89 (d, J = 9.0, 1H), 7.76 (d, J = 8.5, 1H), 7.63 (d, J = 8.1, 1H), 7.59 (s, 1H), 7.54 (d, J = 8.8, 2H), 7.38-7.24 (m, 3H), 7.09 (d, J = 7.4, 1H), 7.02 (dd, J = 2.4, 8.8, 4H), 6.90 (d, J = 8.9, 1H). |
| 28 | ¹H NMR (300 MHz, CDCl₃) δ 7.92 (d, J = 9.0 Hz, 1H), 7.76 (d, J = 8.3 Hz, 1H), 7.65 (d, J = 7.8 Hz, 1H), 7.59 (t, J = 7.0 Hz, 1H), 7.53 (d, J = 8.8 Hz, 2H), 7.31 (t, J = 7.0 Hz, 1H), 7.15 (d, J = 8.4 Hz, 2H), 7.02 (d, J = 8.8 Hz, 2H), 6.94 (d, J = 8.4 Hz, 2H), 6.92 (d, J = 7.0 Hz, 1H), 6.70 (s, 1H), 2.34 (s, 3H). |
| 29 | ¹H NMR (300 MHz, CDCl₃) δ 7.91 (d, J = 9.0 Hz, 1H), 7.76 (d, J = 8.3 Hz, 1H), 7.64 (d, J = 8.3 Hz, 1H), 7.63-7.58 (m, 1H), 7.55 (d, J = 8.9 Hz, 2H), 7.32-7.26 (d, J = 7.9 Hz, 1H), 7.24-7.15 (m, 1H), 7.13-7.05 (m, 3H), 7.02 (d, J = 8.9 Hz, 2H), 6.91 (d, J = 9.0 Hz, 1H), 6.78 (s, 1H). |

TABLE II-continued

| Ex | Characterizations |
|---|---|
| 30 | $^1$H NMR (300 MHz, CDCl$_3$) δ 7.95-7.88 (m, 1H), 7.76 (d, J = 8.2 Hz, 1H), 7.63 (d, J = 8.2 Hz, 1H), 7.61-7.54 (m, 3H), 7.45 (t, J = 8.7 Hz, 1H), 7.30 (d, J = 8.0 Hz, 1H), 7.16 (t, J = 8.0 Hz, 1H), 7.04-6.97 (m, 3H), 6.90 (d, J = 8.9 Hz, 1H), 6.85 (s, 1H), 3.87 (s, 3H). |
| 31 | $^1$H NMR (300 MHz, CDCl$_3$) δ 7.87 (d, J = 9.0 Hz, 1H), 7.75-7.69 (m, 3H), 7.54 (d, J = 7.7 Hz, 1H), 7.20 (d, J = 7.7 Hz, 1H), 7.15 (d, J = 8.4 Hz, 2H), 7.04 (d, J = 8.9 Hz, 2H), 6.95 (d, J = 8.4 Hz, 3H), 6.89 (d, J = 9.0 Hz, 1H), 2.35 (s, 3H).<br>[M + H]$^+$ = 361.0 |
| 32 | $^1$H NMR (300 MHz, CDCl$_3$) δ 7.91 (d, J = 8.8 Hz, 1H), 7.75 (d, J = 9.0 Hz, 2H), 7.71 (dd, J = 8.0, 1.2 Hz, 1H), 7.56 (dd, J = 8.0, 1.2 Hz, 1H), 7.23-7.15 (m, 2H), 7.13-6.98 (m, 5H), 6.95-6.83 (m, 3H), 6.67 (d, J = 8.8 Hz, 1H). |
| 33 | $^1$H NMR (300 MHz, CDCl$_3$) δ 7.93 (d, J = 8.9 Hz, 2H), 7.78 (d, J = 9.0 Hz, 2H), 7.73 (dd, J = 7.7, 1.2 Hz, 1H), 7.58 (dd, J = 7.7, 1.2 Hz, 1H), 7.51-7.44 (m, 1H), 7.26-7.19 (m, 1H), 7.17 (dd, J = 1.1, 1.2 Hz, 1H), 7.07-7.01 (m, 3H), 6.94 (d, J = 8.9 Hz, 1H), 6.89 (s, 1H), 3.88 (s, 3H).<br>[M + H]$^+$ = 404.9 |
| 34 | $^1$H NMR (300 MHz, CDCl$_3$) δ 7.93 (d, J = 9.0 Hz, 1H), 7.77 (d, J = 8.2 Hz, 1H), 7.65 (d, J = 8.2 Hz, 1H), 7.60 (d, J = 8.9 Hz, 2H), 7.33-7.27 (m, 3H), 7.03 (d, J = 8.9 Hz, 2H), 6.96 (d, J = 9.0 Hz, 2H), 6.92 (d, J = 9.0 Hz, 1H), 6.70 (s, 1H). |
| 35 | $^1$H NMR (300 MHz, CDCl$_3$) δ 7.92 (d, J = 8.9 Hz, 1H), 7.76 (d, J = 8.1 Hz, 1H), 7.65 (d, J = 8.3 Hz, 1H), 7.58 (dd, J = 13.0, 6.5 Hz, 3H), 7.31 (t, J = 6.8 Hz, 1H), 7.08-6.96 (m, 6H), 6.91 (d, J = 9.0 Hz, 1H), 6.67 (s, 1H). |
| 36 | $^1$H NMR (300 MHz, CDCl$_3$) δ 7.93 (d, J = 8.7 Hz, 1H), 7.82 (d, J = 8.8 Hz, 2H), 7.72 (dd, J = 8.0, 1.0 Hz, 1H), 7.57 (dd, J = 8.0, 1.0 Hz, 1H), 7.32-7.26 (m, 2H), 7.22 (t, J = 8.0 Hz, 1H), 7.06 (d, J = 8.8 Hz, 2H), 6.97-6.91 (m, 3H), 6.87 (s, 1H).<br>[M + H]$^+$ = 380.9 |
| 37 | $^1$H NMR (300 MHz, CDCl$_3$) δ 7.92 (d, J = 8.8 Hz, 1H), 7.77 (d, J = 9.1 Hz, 2H), 7.72 (dd, J = 8.0, 1.0 Hz, 1H), 7.57 (dd, J = 8.0, 1.0 Hz, 1H), 7.21 (t, J = 8.0 Hz, 1H), 7.07-6.97 (m, 6H), 6.92 (d, J = 8.8 Hz, 1H), 6.86 (s, 1H). |
| 38 | $^1$H NMR (300 MHz, CDCl$_3$) δ 7.88 (d, J = 8.9 Hz, 1H), 7.69 (d, J = 8.2 Hz, 1H), 7.63 (d, J = 8.2 Hz, 1H), 7.60-7.53 (m, 1H), 7.49 (d, J = 8.6 Hz, 1H), 7.30-7.06 (m, 2H), 6.93 (d, J = 2.7 Hz, 1H), 6.86 (dd, J = 8.6, 2.7 Hz, 1H), 6.75 (d, J = 8.9 Hz, 1H), 6.59 (s, 1H), 2.27 (s, 3H).<br>$^{13}$C NMR (75 MHz, CDCl$_3$) δ 153.5, 152.2, 145.4, 141.5, 141.4, 135.5, 132.5, 130.8, 127.4, 125.1, 123.9, 123.7, 122.4, 122.3, 122.2, 121.5, 120.3, 119.3, 117.2, 114.8, 114.5, 113.2, 107.8, 15.9<br>[M + H]$^+$ = 345.2 |
| 39 | $^1$H NMR (300 MHz, CDCl$_3$) δ 7.86 (d, J = 8.9 Hz, 1H), 7.69 (d, J = 8.2 Hz, 1H), 7.62 (d, J = 8.2 Hz, 1H), 7.60-7.53 (m, 1H), 7.42 (d, J = 8.6 Hz, 1H), 7.30-7.26 (m, 1H), 7.25-7.14 (m, 1H), 7.16-7.08 (m, 3H), 6.98 (d, J = 2.8 Hz, 1H), 6.84 (dd, J = 8.6, 2.8 Hz, 1H), 6.73 (d, J = 8.9 Hz, 1H), 6.61 (s, 1H), 2.65 (q, J = 7.5 Hz, 2H), 1.18 (t, J = 7.5 Hz, 3H).<br>$^{13}$C NMR (75 MHz, CDCl$_3$) δ 154.1, 153.6, 152.9, 150.3, 145.5, 141.6, 141.5, 139.2, 135.7, 130.2, 127.6, 125.2, 124.9, 123.8, 122.5, 122.4, 122.4, 121.7, 120.4, 119.4, 115.8, 114.9, 114.7, 113.1, 107.7, 97.7, 22.4, 11.9<br>[M + H]$^+$ = 359.3 |
| 40 | $^1$H NMR (300 MHz, CDCl$_3$) δ 7.82 (d, J = 9.0 Hz, 1H), 7.68 (dd, J = 8.0, 1.1 Hz, 1H), 7.52 (dd, J = 8.0, 1.1 Hz, 1H), 7.36 (s, 1H), 7.14 (t, J = 8.0 Hz, 1H), 6.76 (s, 1H), 6.73 (s, 1H), 6.67 (d, J = 9.0 Hz, 1H), 4.63-4.48 (m, 1H), 3.37-3.25 (m, 1H), 2.25 (s, 3H), 1.37 (d, J = 6.0 Hz, 6H), 1.19 (d, J = 6.9 Hz, 6H).<br>[M + H]$^+$ = 369.3 |
| 41 | $^1$H NMR (300 MHz, CDCl$_3$) δ 7.80 (d, J = 9.0 Hz, 1H), 7.68 (dd, J = 8.0, 1.2 Hz, 1H), 7.51 (dd, J = 8.0, 1.2 Hz, 1H), 7.31 (d, J = 8.6 Hz, 1H), 7.14 (t, J = 8.0 Hz, 1H), 6.80 (d, J = 2.8 Hz, 1H), 6.72 (s, 1H), 6.71-6.67 (m, 1H), 6.65 (d, J = 9.0 Hz, 1H), 4.65 (p, J = 7.1 Hz, 1H), 2.63 (q, J = 7.5 Hz, 2H), 2.53-2.40 (m, 2H), 2.29-2.11 (m, 2H), 1.95-1.81 (m, 2H), 1.79-1.60 (m, 1H), 1.17 (t, J = 7.5 Hz, 3H).<br>[M + H]$^+$ = 353.2 |
| 42 | $^3$H NMR (300 MHz, CDCl$_3$) δ 7.84 (d, J = 9.0 Hz, 1H), 7.75 (d, J = 8.7 Hz, 1H), 7.68 (dd, J = 8.0, 1.1 Hz, 1H), 7.52 (dd, J = 8.0, 1.1 Hz, 1H), 7.15 (t, J = 8.0 Hz, 1H), 7.04 (s, 1H), 6.78 (d, J = 9.0 Hz, 1H), 6.69 (dd, J = 8.7, 2.8 Hz, 1H), 6.52 (d, J = 2.8 Hz, 1H), 4.62 (p, J = 7.1 Hz, 1H), 2.51-2.39 (m, 2H), 2.27-2.08 (m, 2H), 1.97 (tt, J = 8.5, 5.4 Hz, 1H), 1.92-1.79 (m, 1H), 1.76-1.61 (m, 1H), 0.97-0.88 (m, 2H), 0.70-0.63 (m, 2H).<br>[M + H]$^+$ = 365.2 |
| 43 | $^1$H NMR (300 MHz, CDCl$_3$) δ 7.80 (d, J = 9.0 Hz, 1H), 7.67 (dd, J = 8.0, 1.0 Hz, 1H), 7.50 (dd, J = 8.0, 1.0 Hz, 1H), 7.28 (s, 1H), 7.14 (d, J = 8.0 Hz, 1H), 6.75 (s, 1H), 6.72 (s, 1H), 6.67 (d, J = 9.0 Hz, 1H), 4.51 (p, J = 6.1 Hz, 1H), 2.23 (s, 3H), 2.18 (s, 3H), 1.35 (d, J = 6.1 Hz, 6H).<br>[M + H]$^+$ = 341.2 |
| 44 | $^1$H NMR (300 MHz, CDCl$_3$) δ 7.85 (d, J = 9.0 Hz, 1H), 7.73 (d, J = 8.7 Hz, 1H), 7.69 (dd, J = 8.0, 1.2 Hz, 1H), 7.53 (dd, J = 8.0, 1.2 Hz, 1H), 7.16 (t, J = 8.0 Hz, 1H), 7.03 (s, 1H), 6.82-6.72 (m, 2H), 6.56 (d, J = 2.8 Hz, 1H), 4.74 (td, J = 5.4, 2.7 Hz, 1H), 2.03-1.76 (m, 7H), 1.69-1.60 (m, 2H), 0.98-0.87 (m, 2H), 0.71-0.64 (m, 2H).<br>$^{13}$C NMR (75 MHz, CDCl$_3$) δ 154.3, 153.4, 142.0, 136.4, 135.6, 128.8, 127.6, 127.5, 124.2, 123.0, 122.7, 119.9, 117.4, 111.5, 110.5, 109.3, 77.1, 30.6, 21.7, 9.2, 5.3<br>[M + H]$^+$ = 379.2 |
| 45 | $^1$H NMR (300 MHz, CDCl$_3$) δ 7.82 (d, J = 9.0 Hz, 1H), 7.60 (t, J = 8.0 Hz, 2H), 7.54-7.47 (m, 1H), 7.41 (d, J = 8.6 Hz, 1H), 7.22 (t, J = 8.0 Hz, 1H), 7.15 (s, 1H), 7.07 (t, J = 9.0 Hz, 1H), 6.86 (d, J = 2.8 Hz, 1H), 6.82-6.73 (m, 2H), 6.72-6.64 (m, 2H), 3.78 (s, 3H), 2.21 (s, 3H).<br>[M + H]$^+$ = 375.1 |
| 46 | $^1$H NMR (300 MHz, CDCl$_3$) δ 7.88 (d, J = 8.9 Hz, 1H), 7.80 (d, J = 8.7 Hz, 1H), 7.73 (d, J = 8.2 Hz, 1H), 7.62 (d, J = 8.2 Hz, 1H), 7.59-7.54 (m, 1H), 7.29-7.24 (m, 1H), 7.21-7.15 (m, 1H), 7.12-7.00 (m, 2H), 6.88-6.81 (m, 2H), 6.77 (d, J = 2.8 Hz, 1H), 1.95 (tt, J = 8.4, 5.4 Hz, 1H), 1.01-0.85 (m, 2H), 0.69-0.60 (m, 2H).<br>$^{13}$C NMR (75 MHz, CDCl$_3$) δ 155.8, 155.4, 153.7, 147.8, 144.5, 144.4, 144.3, 137.8, 137.6, 134.8, |

TABLE II-continued

| Ex | Characterizations |
|---|---|
| | 129.9, 127.5, 126.5, 124.7, 124.6, 124.5, 124.4, 124.1, 124.0, 122.9, 121.2, 117.2, 116.9, 116.5, 115.6, 111.2, 100.0, 80.3, 11.7, 7.2<br>[M + H]⁺ = 371.2 |
| 47 | ¹H NMR (400 MHz, d₆-DMSO) δ 8.66 (s, 1H), 8.03 (d, J = 9.0 Hz, 1H), 7.87 (d, J = 8.7 Hz, 1H), 7.71-7.63 (m, 2H), 7.47 (d, J = 7.4 Hz, 2H), 7.41 (t, J = 7.4 Hz, 2H), 7.34 (t, J = 7.2 Hz, 1H), 7.18 (t, J = 7.7 Hz, 1H), 7.03 (d, J = 8.9 Hz, 1H), 6.95 (d, J = 2.5 Hz, 1H), 6.88 (dd, J = 8.8, 2.6 Hz, 1H), 5.10 (s, 2H), 2.27 (s, 3H).<br>[M + H]⁺ = 375.0 |
| 48 | ¹H NMR (400 MHz, d₆-DMSO) δ 8.49 (s, 1H), 8.03 (d, J = 9.0 Hz, 1H), 7.67 (t, J = 7.0 Hz, 2H), 7.57 (s, 1H), 7.19 (t, J = 7.7 Hz, 1H), 7.09 (d, J = 9.0 Hz, 1H), 6.85 (s, 1H), 4.53 (p, J = 6.0 Hz, 1H), 2.25 (s, 3H), 2.14 (ddd, J = 13.7, 8.4, 5.4 Hz, 1H), 1.30 (d, J = 6.0 Hz, 6H), 0.90-0.84 (m, 2H), 0.67 (q, J = 5.9 Hz, 2H).<br>[M + H]⁺ = 367.1 |
| 49 | ¹H NMR (400 MHz, CDCl₃) δ 8.00 (d, J = 9.1 Hz, 2H), 7.80 (d, J = 9.0 Hz, 2H), 7.65 (dd, J = 22.8, 7.6 Hz, 4H), 7.33-7.22 (m, 3H), 7.03 (d, J = 8.2 Hz, 1H), 6.96 (d, J = 7.8 Hz, 1H), 4.61 (p, J = 6.1 Hz, 1H), 2.03 (s, 3H), 1.40 (d, J = 6.1 Hz, 6H).<br>[M + H]⁺ = 488.3 |
| 50 | ¹H NMR (400 MHz, d₆-DMSO) δ 8.84 (s, 1H), 8.09 (d, J = 9.0 Hz, 1H), 7.70 (dd, J = 7.6, 3.1 Hz, 3H), 7.49 (d, J = 7.3 Hz, 2H), 7.41 (t, J = 7.5 Hz, 2H), 7.34 (t, J = 7.2 Hz, 1H), 7.22 (t, J = 7.8 Hz, 1H), 7.19-7.11 (m, 2H), 6.87 (d, J = 8.2 Hz, 1H), 5.16 (s, 2H), 2.20 (s, 3H).<br>[M + H]⁺ = 375.1 |
| 51 | ¹H NMR (300 MHz, CDCl₃) δ 7.87 (d, J = 8.8 Hz, 1H), 7.71 (d, J = 8.0 Hz, 1H), 7.63 (d, J = 8.3 Hz, 1H), 7.61-7.55 (m, 1H), 7.43 (d, J = 8.5 Hz, 1H), 7.02 (d, J = 9.1 Hz, 2H), 6.90 (d, J = 9.1 Hz, 2H), 6.82 (dd, J = 8.7, 2.8 Hz, 1H), 6.74 (d, J = 9.0 Hz, 1H), 6.46 (s, 1H), 3.82 (s, 4H), 2.26 (s, 3H).<br>[M + H]⁺ = 357.1 |
| 52 | ¹H NMR (300 MHz, CDCl₃) δ 7.89 (d, J = 8.9 Hz, 1H), 7.73 (d, J = 8.4 Hz, 1H), 7.68 (d, J = 8.6 Hz, 1H), 7.63 (d, J = 8.1 Hz, 1H), 7.58 (t, J = 7.7 Hz, 1H), 7.28 (d, J = 7.0 Hz, 1H), 7.04 (t, J = 9.1 Hz, 2H), 6.85 (d, J = 8.9 Hz, 2H), 6.78 (dd, J = 5.5, 2.9 Hz, 1H), 6.75-6.73 (m, 1H), 6.71 (d, J = 2.8 Hz, 1H), 6.67 (ddd, J = 9.0, 2.9, 1.4 Hz, 1H), 3.81 (s, 3H), 2.00-1.90 (m, 1H), 0.95 (td, J = 6.1, 4.2 Hz, 2H), 0.68-0.62 (td, J = 6.1, 4.2 Hz, 2H).<br>[M + H]⁺ = 401.1 |
| 53 | ³H NMR (300 MHz, CDCl₃) δ 7.99 (d, J = 9.2 Hz, 1H), 7.84 (d, J = 8.4 Hz, 1H), 7.69 (d, J = 7.6 Hz, 2H), 7.38 (t, J = 7.5 Hz, 1H), 7.19 (d, J = 8.6 Hz, 1H), 6.95 (t, J = 9.0 Hz, 1H), 6.85 (d, J = 2.6 Hz, 1H), 6.78-6.74 (m, 1H), 6.74-6.70 (m, 2H), 6.65 (d, J = 8.8 Hz, 1H), 2.23 (s, 3H).<br>[M + H]⁺ = 361.1 |
| 54 | ¹H NMR (400 MHz, d₆-DMSO) δ 8.73 (s, 1H), 8.18 (dd, J = 12.8, 8.1 Hz, 2H), 8.09 (d, J = 9.0 Hz, 1H), 7.99 (d, J = 7.2 Hz, 1H), 7.74-7.67 (m, 3H), 7.63-7.54 (m, 2H), 7.48 (t, J = 7.9 Hz, 1H), 7.22 (t, J = 7.8 Hz, 1H), 7.17 (d, J = 9.0 Hz, 1H), 7.03 (d, J = 2.7 Hz, 1H), 6.99 (d, J = 7.5 Hz, 1H), 6.92 (dd, J = 8.8, 2.8 Hz, 1H), 2.31 (s, 3H).<br>[M + H]⁺ = 411.0 |
| 55 | ¹H NMR (400 MHz, d₆-DMSO) δ 8.94 (s, 1H), 8.12 (d, J = 8.9 Hz, 1H), 8.01 (d, J = 8.1 Hz, 1H), 7.71 (d, J = 7.8 Hz, 2H), 7.40-7.31 (m, 2H), 7.29-7.20 (m, 3H), 7.07 (t, J = 7.3 Hz, 1H), 6.93 (d, J = 7.9 Hz, 2H), 6.76 (d, J = 8.0 Hz, 1H), 2.15 (s, 3H).<br>[M + H]⁺ = 361.0 |
| 56 | ¹H NMR (400 MHz, d₆-DMSO) δ 8.81 (s, 1H), 8.15 (d, J = 8.7 Hz, 1H), 8.11 (d, J = 9.0 Hz, 1H), 7.72 (dd, J = 7.7, 2.7 Hz, 2H), 7.39 (t, J = 7.9 Hz, 2H), 7.24 (t, J = 7.8 Hz, 1H), 7.18-7.09 (m, 2H), 7.02 (d, J = 8.0 Hz, 2H), 6.97 (d, J = 2.7 Hz, 1H), 6.89 (dd, J = 8.7, 2.8 Hz, 1H), 2.30 (s, 3H).<br>[M + H]⁺ = 361.1 |
| 57 | ¹H NMR (400 MHz, d₆-DMSO) δ 8.74 (s, 1H), 8.26 (d, J = 8.8 Hz, 1H), 8.10 (d, J = 9.0 Hz, 1H), 7.97 (d, J = 8.9 Hz, 1H), 7.92 (d, J = 8.0 Hz, 1H), 7.82 (d, J = 8.2 Hz, 1H), 7.71 (d, J = 7.3 Hz, 2H), 7.46 (dt, J = 23.3, 6.9 Hz, 2H), 7.38 (d, J = 2.3 Hz, 1H), 7.33 (dd, J = 8.9, 2.4 Hz, 1H), 7.27-7.16 (m, 2H), 7.04 (d, J = 2.7 Hz, 1H), 6.97 (dd, J = 8.8, 2.8 Hz, 1H), 2.33 (s, 3H).<br>[M + H]⁺ = 411.0 |
| 58 | ¹H NMR (400 MHz, d₆-DMSO) δ 8.46 (d, J = 8.8 Hz, 1H), 7.97 (d, J = 7.9 Hz, 1H), 7.86 (d, J = 8.1 Hz, 1H), 7.77 (t, J = 7.6 Hz, 1H), 7.52 (t, J = 7.4 Hz, 1H), 7.40 (q, J = 8.3 Hz, 4H), 7.31 (d, J = 9.0 Hz, 1H), 7.14 (t, J = 7.4 Hz, 1H), 7.02 (d, J = 7.9 Hz, 2H), 7.01-6.93 (m, 1H), 2.15 (s, 3H).<br>[M + H]⁺ = 327.1 |
| 59 | ¹H NMR (400 MHz, d₆-DMSO) δ 8.81 (s, 1H), 8.71 (d, J = 1.7 Hz, 1H), 8.56 (dd, J = 4.8, 1.5 Hz, 1H), 8.08 (d, J = 9.0 Hz, 1H), 7.91 (d, J = 7.9 Hz, 1H), 7.76 (d, J = 8.1 Hz, 1H), 7.70 (dd, J = 7.8, 2.5 Hz, 2H), 7.45 (dd, J = 7.8, 4.8 Hz, 1H), 6.90 (d, J = 8.2 Hz, 1H), 5.21 (s, 2H), 7.26-7.11 (m, 3H), 2.19 (s, 3H).<br>[M + H]⁺ = 375.9 |
| 60 | ¹H NMR (400 MHz, d₆-DMSO) δ 9.81 (s, 1H), 8.28 (t, J = 2.1 Hz, 1H), 8.11 (d, J = 8.9 Hz, 1H), 7.71 (d, J = 7.8 Hz, 2H), 7.66 (dd, J = 8.1, 1.5 Hz, 1H), 7.44-7.37 (m, 2H), 7.34 (t, J = 8.2 Hz, 1H), 7.25 (t, J = 7.8 Hz, 1H), 7.13 (t, J = 7.9 Hz, 2H), 7.07 (d, J = 7.9 Hz, 2H), 6.68 (dd, J = 8.0, 2.2 Hz, 1H).<br>[M + H]⁺ = 347.0 |
| 61 | ¹H NMR (400 MHz, d₆-DMSO) δ 8.60 (s, 1H), 8.54 (d, J = 2.5 Hz, 1H), 8.11 (d, J = 9.0 Hz, 1H), 7.73-7.68 (m, 1H), 7.66 (dd, J = 7.6, 1.3 Hz, 1H), 7.39-7.30 (m, 3H), 7.23 (t, J = 7.7 Hz, 2H), 7.07 (t, J = 7.4 Hz, 1H), 7.04-6.98 (m, 2H), 6.70 (dd, J = 8.2, 2.5 Hz, 1H), 2.36 (s, 3H).<br>[M + H]⁺ = 360.9 |
| 62 | ¹H NMR (400 MHz, d₆-DMSO) δ 9.74 (s, 1H), 8.22 (d, J = 9.0 Hz, 2H), 8.11 (d, J = 8.9 Hz, 1H), 7.76 (d, J = 7.6 Hz, 1H), 7.72 (d, J = 7.9 Hz, 1H), 7.41-7.34 (m, 2H), 7.26 (t, J = 7.8 Hz, 1H), 7.15-7.07 (m, 2H), 7.07-7.02 (m, 2H), 6.99 (d, J = 7.9 Hz, 2H).<br>[M + H]⁺ = 347.1 |

TABLE II-continued

| Ex | Characterizations |
|---|---|
| 63 | ¹H NMR (400 MHz, d₆-DMSO) δ 9.50 (s, 1H), 8.08 (d, J = 9.1 Hz, 1H), 7.72 (d, J = 8.0 Hz, 1H), 7.69 (d, J = 7.5 Hz, 1H), 7.32-7.22 (m, 3H), 7.21-7.14 (m, 2H), 7.03 (s, 1H), 6.77 (s, 1H), 6.64 (d, J = 9.0 Hz, 1H), 2.09 (s, 3H), 2.00 (s, 3H).<br>[M + H]⁺ = 393.2 |
| 64 | ¹H NMR (400 MHz, d₆-DMSO) δ 8.72 (s, 1H), 8.03 (d, J = 8.9 Hz, 1H), 7.66 (d, J = 7.8 Hz, 2H), 7.45-7.36 (m, 2H), 7.15 (q, J = 7.7 Hz, 2H), 7.04 (d, J = 7.8 Hz, 2H), 6.82 (s, 2H), 2.17 (s, 6H).<br>[M + H]⁺ = 375.0 |
| 65 | ¹H NMR (400 MHz, d₆-DMSO) δ 8.39 (s, 1H), 7.95 (d, J = 8.9 Hz, 1H), 7.66 (d, J = 7.7 Hz, 1H), 7.47 (dd, J = 6.0, 1.3 Hz, 2H), 7.29 (s, 1H), 7.19 (ddd, J = 8.0, 6.0, 2.1 Hz, 1H), 6.89-6.82 (m, 2H), 4.55 (hept, J = 6.0 Hz, 1H), 2.17 (s, 3H), 2.11 (s, 3H), 1.29 (d, J = 6.0 Hz, 6H).<br>[M + H]⁺ = 307.1 |
| 66 | ¹H NMR (400 MHz, d₆-DMSO) δ 8.41 (s, 1H), 7.96 (d, J = 8.9 Hz, 1H), 7.66 (d, J = 7.8 Hz, 1H), 7.56-7.33 (m, 4H), 7.26-7.10 (m, 2H), 7.06 (d, J = 7.8 Hz, 2H), 6.81 (s, 3H), 2.14 (s, 6H).<br>[M + H]⁺ = 341.0 |
| 67 | ¹H NMR (400 MHz, d₆-DMSO) δ 8.41 (s, 1H), 7.96 (d, J = 8.9 Hz, 1H), 7.66 (d, J = 7.8 Hz, 1H), 7.47 (t, J = 6.1 Hz, 3H), 7.20 (td, J = 6.9, 6.2, 1.7 Hz, 1H), 6.90 (d, J = 8.9 Hz, 1H), 6.82 (s, 1H), 6.77 (d, J = 8.6 Hz, 1H), 4.58 (hept, J = 6.1 Hz, 1H), 2.19 (s, 3H), 1.28 (d, J = 6.0 Hz, 6H).<br>[M + H]⁺ = 293.1 |
| 68 | ¹H NMR (400 MHz, d₆-DMSO) δ 8.52 (s, 1H), 8.01 (d, J = 8.9 Hz, 1H), 7.78 (d, J = 8.7 Hz, 1H), 7.70 (d, J = 7.9 Hz, 1H), 7.51 (d, J = 3.8 Hz, 2H), 7.40 (t, J = 7.9 Hz, 2H), 7.28-7.19 (m, 1H), 7.12 (t, J = 7.4 Hz, 1H), 7.03 (d, J = 8.7 Hz, 3H), 6.96 (d, J = 2.7 Hz, 1H), 6.88 (dd, J = 8.6, 2.8 Hz, 1H), 2.25 (s, 3H).<br>[M + H]⁺ = 327.2 |
| 69 | ¹H NMR (400 MHz, d₆-DMSO) δ 8.55 (s, 1H), 8.24 (d, J = 2.6 Hz, 1H), 8.11 (d, J = 9.0 Hz, 1H), 7.77-7.68 (m, 2H), 7.30 (d, J = 9.0 Hz, 1H), 7.25 (t, J = 7.8 Hz, 1H), 7.10 (d, J = 8.4 Hz, 1H), 6.58 (dd, J = 8.3, 2.6 Hz, 1H), 4.82 (t, J = 5.5 Hz, 1H), 4.03 (t, J = 5.2 Hz, 2H), 3.72 (q, J = 5.3 Hz, 2H), 2.27 (s, 3H).<br>[M + H]⁺ = 329.0 |
| 70 | ¹H NMR (400 MHz, CDCl₃) δ 7.88 (d, J = 8.9 Hz, 1H), 7.71 (d, J = 7.5 Hz, 1H), 7.56 (d, J = 7.9 Hz, 1H), 7.34 (d, J = 8.0 Hz, 1H), 7.20 (q, J = 7.7 Hz, 2H), 6.86 (d, J = 8.9 Hz, 2H), 6.77 (d, J = 8.2 Hz, 1H), 4.19-4.11 (m, 2H), 4.03 (d, J = 4.0 Hz, 2H), 2.23 (s, 3H), 2.07 (s, 1H).<br>[M + H]⁺ = 329.0 |
| 71 | ¹H NMR (300 MHz, CDCl₃) δ 7.83 (d, J = 9.0 Hz, 1H), 7.71 (dd, J = 7.5, 1.1 Hz, 1H), 7.54 (dd, J = 8.0, 0.9 Hz, 1H), 7.17 (t, J = 7.8 Hz, 1H), 7.04 (s, 2H), 6.63 (bs, 1H), 6.32 (d, J = 8.9 Hz, 1H), 2.64-2.55 (m, 2H), 2.24 (s, 3H), 1.64-1.49 (m, 2H), 0.88 (t, J = 7.3 Hz, 3H). |
| 72 | ¹H NMR (300 MHz, CDCl₃) δ 7.85 (d, J = 8.9 Hz, 1H), 7.71 (dd, J = 7.5, 1.2 Hz, 1H), 7.55 (dd, J = 8.0, 1.1 Hz, 1H), 7.17 (t, J = 7.8 Hz, 1H), 7.00 (d, J = 1.8 Hz, 1H), 6.76 (bs, 1H), 6.65 (d, J = 1.8 Hz, 1H), 6.42 (d, J = 8.9 Hz, 1H), 2.28 (s, 3H), 2.09-2.00 (m, 1H), 0.95-0.86 (m, 2H), 0.67-0.59 (m, 2H). |
| 73 | ¹H NMR (300 MHz, CDCl₃) δ 7.86 (d, J = 9.0 Hz, 1H), 7.72 (d, J = 8.4 Hz, 1H), 7.62 (d, J = 8.2 Hz, 1H), 7.57 (t, J = 7.2 Hz, 1H), 7.52 (d, J = 8.7 Hz, 1H), 7.26 (t, J = 7.2 Hz, 1H), 6.79 (d, J = 8.9 Hz, 1H), 6.76 (d, J = 8.6 Hz, 1H), 6.58 (d, J = 2.7 Hz, 1H), 4.52 (dt, J = 12.0, 6.0 Hz, 1H), 2.03-1.90 (m, 1H), 1.35 (d, J = 6.1 Hz, 6H), 0.98-0.85 (m, 2H), 0.72-0.60 (m, 2H). |
| 74 | ¹H NMR (300 MHz, CDCl₃) δ 7.82 (d, J = 9.0 Hz, 1H), 7.68 (d, J = 8.3 Hz, 1H), 7.61 (d, J = 8.0 Hz, 1H), 7.56 (t, J = 8.3 Hz, 1H), 7.27 (d, J = 8.9 Hz, 1H), 7.23 (t, J = 8.3 Hz, 1H), 6.83 (d, J = 2.8 Hz, 1H), 6.77 (dd, J = 8.6, 2.9 Hz, 1H), 6.66 (d, J = 9.0 Hz, 1H), 6.55 (bs, 1H), 4.55 (dt, J = 12.1, 6.0 Hz, 1H), 2.62-2.53 (m, 2H), 1.67-1.51 (m, 2H), 1.36 (d, J = 6.1 Hz, 6H), 0.91 (t, J = 7.3 Hz, 3H). |
| 75 | ¹H NMR (300 MHz, CDCl₃) δ 7.92 (d, J = 8.9 Hz, 1H), 7.73 (d, J = 8.4 Hz, 1H), 7.67 (d, J = 8.3 Hz, 1H), 7.65 (d, J = 7.8 Hz, 1H), 7.60 (t, J = 8.3 Hz, 1H), 7.30 (t, J = 7.9 Hz, 1H), 7.11 (d, J = 9.3 Hz, 2H), 6.83 (d, J = 8.9 Hz, 1H), 6.55 (bs, 1H), 2.64 (dd, J = 7.5 Hz, 2H), 1.65 (q, J = 7.5 Hz, 2H), 0.97 (t, J = 7.3 Hz, 3H). |
| 76 | ¹H NMR (300 MHz, CDCl₃) δ 7.85 (d, J = 9.0 Hz, 1H), 7.70 (d, J = 8.2 Hz, 1H), 7.62 (d, J = 8.3 Hz, 1H), 7.58 (t, J = 8.4 Hz, 1H), 7.36 (d, J = 8.6 Hz, 1H), 7.29-7.23 (m, 1H), 7.09 (t, J = 9.0 Hz, 1H), 6.92 (d, J = 2.9 Hz, 1H), 6.79 (dd, J = 5.6, 2.9 Hz, 1H), 6.75 (d, J = 2.4 Hz, 1H), 6.71 (d, J = 9.0 Hz, 1H), 6.72-6.66 (m, 1H), 6.44 (s, 1H), 3.82 (s, 3H), 2.63 (q, J = 7.6 Hz, 2H), 1.17 (t, J = 7.5 Hz, 3H).<br>[M + H]⁺ = 389.3 |
| 77 | ¹H NMR (300 MHz, CDCl₃) δ 7.90 (d, J = 8.9 Hz, 1H), 7.74 (d, J = 8.3 Hz, 1H), 7.63 (d, J = 7.9 Hz, 1H), 7.61-7.54 (m, 1H), 7.48 (d, J = 9.0 Hz, 2H), 7.31-7.27 (m, 1H), 7.06 (t, J = 9.1 Hz, 1H), 6.96 (d, J = 8.9 Hz, 2H), 6.89 (d, J = 8.9 Hz, 1H), 6.77 (dd, J = 12.1, 2.9 Hz, 1H), 6.69-6.65 (m, 2H), 3.81 (s, 3H).<br>[M + H]⁺ = 361.2 |
| 78 | ¹H NMR (300 MHz, CDCl₃) δ 7.93 (d, J = 8.9 Hz, 1H), 7.75 (dd, J = 8.0, 1.1 Hz, 1H), 7.73 (s, 1H), 7.60 (dd, J = 8.0, 1.1 Hz, 1H), 7.23 (t, J = 7.8 Hz, 1H), 7.17 (d, J = 8.3 Hz, 1H), 6.95 (d, J = 8.9 Hz, 1H), 6.79 (s, 1H), 6.70 (dd, J = 8.3, 2.5 Hz, 1H), 4.68 (dt, J = 12.1, 6.0 Hz, 1H), 2.30 (s, 3H), 1.39 (d, J = 6.1 Hz, 6H). |
| 79 | ¹H NMR (400 MHz, d₆-DMSO) δ 8.64 (s, 1H), 8.02 (d, J = 9.0 Hz, 1H), 7.73-7.62 (m, 3H), 7.17 (t, J = 7.8 Hz, 1H), 6.94 (d, J = 8.9 Hz, 1H), 6.88-6.78 (m, J = 3.6, 3.6 Hz, 2H), 4.85 (br. s., 1H), 4.00 (t, J = 5.0 Hz, 2H), 3.73 (t, J = 5.0 Hz, 2H), 2.65-2.57 (m, 2H), 1.62-1.49 (m, 2H), 0.86 (t, J = 7.3 Hz, 3H).<br>[M + H]⁺ = 357.3 |

The following examples are provided as illustrations and in no way limit the scope of this invention.

The following examples illustrate in detail the preparation of some compounds according to the invention. The structures of the products obtained have been confirmed by NMR spectra.

EXAMPLES

Example 1: Compound (2) in Table I

According to route (C), 2-bromo-4-trifluoromethoxyaniline (2.3 mL, 15 mmoles, 1 eq.) was placed in 1,4-dioxane (55 mL) with Pd(dppf)Cl$_2$·CH$_2$Cl$_2$ (1.2 g, 1.5 mmole, 0.1 eq.). Upon addition of Cs$_2$CO$_3$ (19.6 g, 60 mmoles, 4 eq.) and ethylboronic acid (3.3 g, 45 mmoles, 3 eq.), the reaction mixture was heated at 100° C. and stirred for 14 hours under an inert atmosphere of argon. The reaction mixture was then concentrated under reduced pressure and the resulting residue was purified by column chromatography on silica gel to afford 2-ethyl-4-(trifluoromethoxy)aniline (1.3 g, 42%).

$^1$H NMR (300 MHz, CDCl$_3$) δ 6.93 (s, 1H), 6.90 (d, J=8.5 Hz, 1H), 6.63 (d, J=8.5 Hz, 1H), 3.64 (s, 2H), 2.49 (q, J=7.5 Hz, 2H), 1.25 (t, J=7.5 Hz, 3H).

According to route (A), a reaction mixture of 2,8-dichloroquinoline (1.16 g, 5.85 mmoles, 1.0 eq.), 2-ethyl-4-(trifluoromethoxy)aniline (1.20 g, 5.85 mmoles, 1.0 eq.), Pd(OAc)$_2$ (53 mg, 0.23 mmol, 4 mol %), XantPhos (133 mg, 0.23 mmol, 4 mol %) and Cs$_2$CO$_3$ (5.46 g, 16.75 mmoles, 2.9 eq.) in t-BuOH (23.4 mL) was heated at 90° ° C. for 3 days. Upon cooling to room temperature, the reaction mixture was concentrated under reduced pressure and the resulting residue was diluted with dichloromethane. The organic phase was then washed with water, dried over MgSO$_4$, filtered and concentrated under reduced pressure. The resulting residue was purified by column chromatography on silica gel to afford a fraction which, after trituration in cyclohexane, gave 8-chloro-N-[2-ethyl-4-(trifluoromethoxy)phenyl]quinolin-2-amine (2) (626 mg, 29%).

$^1$H NMR (300 MHZ, CDCl$_3$) δ 7.96 (d, J=9.0 Hz, 1H), 7.91 (d, J=9.0 Hz, 1H), 7.72 (dd, J=8.0, 1.0 Hz, 1H), 7.57 (dd, J=8.0, 1.0 Hz, 1H), 7.21 (t, J=8.0 Hz, 1H), 7.15-7.13 (m, 2H), 6.83 (d, J=9.0 Hz, 1H), 6.74 (s, 1H), 2.71 (q, J=7.5 Hz, 2H), 1.26 (t, J=7.5 Hz, 3H).

$^{13}$C NMR (75 MHZ, CDCl$_3$) δ 153.1, 143.7, 141.6, 136.3, 136.0, 133.5, 127.9, 127.6, 124.1, 122.9, 122.3, 120.5, 119.1, 116.9, 109.2, 22.0, 11.4

[M+H]$^+$=367.2.

Example 2: Compound (4) in Table I

According to route (C), 2-bromo-4-trifluoromethoxyaniline (1.5 mL, 10 mmoles, 1 eq.) was placed in 1,4-dioxane (36 mL) with Pd(dppf)Cl$_2$·CH$_2$Cl$_2$ (817 mg, 1 mmole, 0.1 eq.). Upon addition of K$_3$PO$_4$ (8.5 g, 40 mmoles, 4 eq.) and cyclopropylboronic acid (2.6 g, 30 mmoles, 3 eq.), the reaction mixture was heated at 100° C. and stirred for 16 hours under an inert atmosphere of argon. The reaction mixture was then concentrated under reduced pressure and the resulting residue was purified by column chromatography on silica gel to afford 2-cyclopropyl-4-(trifluoromethoxy)aniline (1.09 g, 50%).

$^1$H NMR (300 MHZ, CDCl$_3$) δ 6.90 (d, J=7.0 Hz, 2H), 6.62, 6.62 (dd, J=7.0, 2.0 Hz, 1H), 3.97 (s, 2H), 1.71-1.62 (m, 1H), 0.93 (m, 2H), 0.60 (m, 2H).

According to route (A), a reaction mixture of 2,8-dichloroquinoline (638 mg, 3.22 mmoles, 1.0 eq.), 2-cyclopropyl-4-(trifluoromethoxy)aniline (700 mg, 3.22 mmoles, 1.0 eq.), Pd(OAc)$_2$ (29 mg, 0.13 mmol, 4 mol %), XantPhos (73 mg, 0.13 mmol, 4 mol %) and Cs$_2$CO$_3$ (3.0 g, 9.23 mmoles, 2.9 eq.) in t-BuOH (12.9 mL) was heated at 90° C. for 3 days under an inert atmosphere of argon. Upon cooling to room temperature, the reaction mixture was concentrated under reduced pressure and the resulting residue was diluted with dichloromethane. The organic phase was then washed with water, dried over MgSO$_4$, filtered and concentrated under reduced pressure. The resulting residue was purified by column chromatography on silica gel to afford a fraction which, after trituration in cyclohexane, gave 8-chloro-N-[2-cyclopropyl-4-(trifluoromethoxy)phenyl]quinolin-2-amine (4) (322 mg, 26%).

$^1$H NMR (300 MHz, CDCl$_3$) δ 8.73 (d, J=9.0 Hz, 1H), 7.95 (d, J=9.0 Hz, 1H), 7.74 (dd, J=8.0, 1.2 Hz, 1H), 7.58 (dd, J=8.0, 1.2 Hz, 1H), 7.35 (s, 1H), 7.22 (d, J=8.0 Hz, 1H), 7.17 (d, J=2.0 Hz, 1H), 7.01 (d, J=2.0 Hz, 1H), 6.92 (d, J=9.0 Hz, 1H), 1.91 (tt, J=8.3, 5.4 Hz, 1H), 1.07 (q, J=4.3 Hz, 2H), 0.74 (q, J=4.3 Hz, 2H).

$^{13}$C NMR (75 MHZ, CDCl$_3$) δ 152.1, 142.2, 141.8, 136.2, 136.0, 131.4, 128.8, 127.9, 124.3, 123.2, 121.1, 118.9, 118.8, 117.8, 117.6, 111.2, 9.5, 4.4

[M+H]$^+$=379.1.

Example 3: Compound (16) in Table I

According to route (B), 4-nitro-5-methylphenol (1.5 g, 10 mmoles, 1 eq.) was placed in N,N-dimethylformamide (8 mL) with K$_2$CO$_3$ (4.2 g, 30 mmoles, 3 eq.). Upon addition of bromocyclopentane (2.1 mL, 20 mmoles, 2 eq.), the reaction mixture was heated at 50° C. and stirred for 4 days under an inert atmosphere of argon. Upon cooling to room temperature, the reaction mixture was concentrated under reduced pressure and the resulting residue was partitioned between ethyl acetate and water. Upon decantation, the organic phase was washed with a saturated aqueous solution of brine, dried over MgSO$_4$, filtered and concentrated under reduced pressure to give 4-(cyclopentyloxy)-2-methyl-1-nitrobenzene (1.8 g, 81%).

$^1$H NMR (300 MHz, CDCl$_3$) δ 8.14-8.02 (m, 1H), 6.80-6.72 (m, 2H), 4.85-4.80 (m, 1H), 2.62 (s, 3H), 2.01-1.78 (m, 6H), 1.75-1.57 (m, 3H).

According to route (D), 4-(cyclopentyloxy)-2-methyl-1-nitrobenzene (1.8 g, 8.1 mmoles, 1 eq.) and tin (II) chloride dihydrate (9.2 g, 40.7 mmoles, 5 eq.) were placed in EtOH (81 mL). The reaction mixture was heated at 60° C. and stirred for 14 hours under an inert atmosphere of argon. The reaction mixture was then concentrated under reduced pressure and the resulting residue was diluted with ethyl acetate. The organic phase was washed with a 1N NaOH aqueous solution then with a saturated aqueous solution of brine, dried over MgSO$_4$, filtered and concentrated under reduced pressure to afford 4-(cyclopentyloxy)-2-methylaniline (1.4 g, 90%).

$^1$H NMR (300 MHz, CDCl$_3$) δ 6.61 (t, J=7.6 Hz, 3H), 4.65-4.61 (m, 1H), 3.33 (s, 2H), 2.62 (s, 3H), 2.01-1.78 (m, 6H), 1.75-1.57 (m, 3H).

According to route (A), a reaction mixture of 2,8-dichloroquinoline (297 mg, 1.5 mmol, 1.5 eq.), 4-(cyclopentyloxy)-2-methylaniline (191 mg, 1.0 mmol, 1 eq.), Pd(OAc)$_2$ (9 mg, 0.04 mmol, 4 mol %), XantPhos (23 mg, 0.04 mmol, 4 mol %) and Cs$_2$CO$_3$ (912 mg, 2.8 mmoles, 2.8 eq.) in t-BuOH (4 mL) was heated at 90° C. for 14 hours under an inert atmosphere of argon. Upon cooling to room temperature, the reaction mixture was concentrated under reduced pressure and the resulting residue was diluted with ethyl acetate. The organic phase was then washed with water, dried over MgSO₄, filtered and concentrated under reduced pressure. The resulting residue was purified by column chromatography on silica gel to afford 8-chloro-N-[4-(cyclopentyloxy)-2-methylphenyl]quinolin-2-amine (16) (94 mg, 27%).

¹H NMR (300 MHz, CDCl₃) δ 7.83 (d, J=9.0 Hz, 1H), 7.69 (dd, J=8.0, 1.0 Hz, 1H), 7.53 (dd, J=8.0, 1.0 Hz, 1H), 7.37 (d, J=8.5 Hz, 1H), 7.15 (t, J=8.0 Hz, 1H), 6.82 (d, J=2.7 Hz, 1H), 6.76 (dd, J=8.5, 2.7 Hz, 1H), 6.72 (s, 1H), 6.67 (d, J=9.0 Hz, 1H), 4.85-4.72 (m, 1H), 2.26 (s, 3H), 1.97-1.75 (m, 8H). [M+H]⁺=353.0.

Example 4: Compound (20) in Table I

According to route (B), 3-bromo-4-nitrophenol (2.2 g, 10 mmoles, 1 eq.) was placed in N,N-dimethylformamide (17 mL) with K₂CO₃ (4.2 g, 30 mmoles, 3 eq.). Upon addition of 2-bromopropane (1.9 mL, 20 mmoles, 2 eq.), the reaction mixture was heated at 90° C. and stirred for 14 hours under an inert atmosphere of argon. Upon cooling to room temperature, the reaction mixture was concentrated under reduced pressure and the resulting residue was partitioned between ethyl acetate and water. Upon decantation, the organic phase was washed with a saturated aqueous solution of brine, dried over MgSO₄, filtered and concentrated under reduced pressure to give 2-bromo-1-nitro-4-(propan-2-yloxy)benzene (2.3 g, 88%).

¹H NMR (300 MHZ, CDCl₃) δ 7.98 (d, J=9.1 Hz, 1H), 7.19 (d, J=2.6 Hz, 1H), 6.87 (dd, J=9.1, 2.6 Hz, 1H), 4.63 (hept, J=6.1 Hz, 1H), 1.38 (d, J=6.1 Hz, 6H).

According to route (C), 2-bromo-1-nitro-4-(propan-2-yloxy)benzene (2.3 g, 8.8 mmoles, 1 eq.) was placed in 1,4-dioxane (32 mL) with Pd(dppf)Cl₂·CH₂Cl₂ (708 mg, 0.9 mmole, 0.1 eq.). Upon addition of K₃PO₄ (7.5 g, 35 mmoles, 4 eq.) and cyclopropylboronic acid (2.3 g, 27 mmoles, 3 eq.), the reaction mixture was heated at 100° C. and stirred for 3 days under an inert atmosphere of argon. The reaction mixture was then concentrated under reduced pressure and the resulting residue was purified by column chromatography on silica gel to afford 2-cyclopropyl-1-nitro-4-(propan-2-yloxy)benzene (1.5 g, 77%).

¹H NMR (300 MHz, CDCl₃) δ 7.95 (d, J=9.1 Hz, 1H), 6.72 (dd, J=9.1, 2.7 Hz, 1H), 6.58 (d, J=2.7 Hz, 1H), 4.61 (hept, J=6.1 Hz, 1H), 2.59-2.50 (m, 1H), 1.36 (d, J=6.1 Hz, 6H), 1.05 (m, 2H), 0.69 (m, 2H).

According to route (D), 2-cyclopropyl-1-nitro-4-(propan-2-yloxy)benzene (1.5 g, 6.8 mmoles, 1 eq.) and tin (II) chloride dihydrate (7.7 g, 34 mmoles, 5 eq.) were placed in EtOH (68 mL). The reaction mixture was heated at 60° C. and stirred for 14 hours under an inert atmosphere of argon. The reaction mixture was then concentrated under reduced pressure and the resulting residue was diluted with dichloromethane. The organic phase was washed with a 1N NaOH aqueous solution then with a saturated aqueous solution of brine, dried over MgSO₄, filtered and concentrated under reduced pressure to afford 2-cyclopropyl-4-(propan-2-yloxy)aniline (1.2 g, 93%).

¹H NMR (300 MHz, CDCl₃) δ 6.65-6.58 (m, 3H), 4.36 (hept, J=6.1 Hz, 1H), 3.69 (s, 2H), 1.73-1.64 (m, 1H), 1.28 (d, J=6.1 Hz, 6H), 0.89 (m, 2H), 0.59 (m, 2H).

According to route (A), a reaction mixture of 2,8-dichloroquinoline (828 mg, 4.18 mmoles, 1.0 eq.), 2-cyclopropyl-4-(propan-2-yloxy)aniline (800 mg, 4.18 mmoles, 1.0 eq.), Pd(OAc)₂ (38 mg, 0.17 mmol, 4 mol %), XantPhos (95 mg, 0.17 mmol, 4 mol %) and Cs₂CO₃ (3.9 g, 12.0 mmoles, 2.9 eq.) in t-BuOH (17 mL) was heated at 90° ° C. for 14 hours under an inert atmosphere of argon. Upon cooling to room temperature, the reaction mixture was concentrated under reduced pressure and the resulting residue was diluted with dichloromethane. The organic phase was then washed with water, dried over MgSO₄, filtered and concentrated under reduced pressure. The resulting residue was purified by column chromatography on silica gel to afford 8-chloro-N-[2-cyclopropyl-4-(propan-2-yloxy)phenyl]quinolin-2-amine (20) (626 mg, 42%).

¹H NMR (300 MHZ, CDCl₃) δ 7.85 (d, J=9.0 Hz, 1H), 7.77 (d, J=9.0 Hz, 1H), 7.69 (dd, J=8.0, 1.2 Hz, 1H), 7.53 (dd, J=8.0, 1.2 Hz, 1H), 7.16 (t, J=8.0 Hz, 1H), 7.05 (s, 1H), 6.79 (dd, J=9.0, 4.1 Hz, 2H), 6.58 (d, J=2.7 Hz, 1H), 4.53 (hept, J=6.1 Hz, 1H), 2.02-1.93 (m, 1H), 1.34 (d, J=6.1 Hz, 6H), 0.94 (q, J=4.3 Hz, 2H), 0.68 (q, J=4.3 Hz, 2H). ¹³C NMR (75 MHz, CDCl₃) δ 154.1, 153.0, 141.9, 135.5, 129.1, 127.5, 127.4, 124.1, 122.9, 122.6, 119.8, 117.3, 112.0, 110.8, 109.3, 67.7, 19.7, 9.1, 5.2

[M+H]⁺=353.2.

Example 5: Compound (22) in Table I

According to route (B), 4-nitro-5-methylphenol (1.5 g, 10 mmoles, 1 eq.) was placed in N,N-dimethylformamide (8 mL) with K₂CO₃ (4.2 g, 30 mmoles, 3 eq.). Upon addition of cyclobutyl bromide (1.9 mL, 20 mmoles, 2 eq.), the reaction mixture was heated at 90° C. and stirred for 14 hours under an inert atmosphere of argon. Upon cooling to room temperature, the reaction mixture was concentrated under reduced pressure and the resulting residue was partitioned between ethyl acetate and water. Upon decantation, the organic phase was washed with a saturated aqueous solution of brine, dried over MgSO₄, filtered and concentrated under reduced pressure to give 4-cyclobutoxy-2-methyl-1-nitrobenzene (1.8 g, 89%).

¹H NMR (300 MHz, CDCl₃) δ 8.08-8.02 (m, 1H), 6.72-6.63 (m, 2H), 4.70 (p, J=7.1 Hz, 1H), 2.61 (s, 3H), 2.53-2.43 (m, 2H), 2.28-2.10 (m, 2H), 1.98-1.83 (m, 1H), 1.81-1.65 (m, 1H).

According to route (D), 4-cyclobutoxy-2-methyl-1-nitrobenzene (1.0 g, 4.8 mmoles, 1 eq.) and tin (II) chloride dihydrate (5.4 g, 23.9 mmoles, 5 eq.) were placed in EtOH (48 mL). The reaction mixture was heated at 60° C. and stirred for 14 hours under an inert atmosphere of argon. The reaction mixture was then concentrated under reduced pressure and the resulting residue was diluted with dichloromethane. The organic phase was washed with a 1N NaOH aqueous solution then with a saturated aqueous solution of brine, dried over MgSO₄, filtered and concentrated under reduced pressure to afford 4-cyclobutoxy-2-methylaniline (846 mg, 99%).

¹H NMR (300 MHz, CDCl₃) δ 6.60-6.58 (m, 2H), 6.55-6.51 (m, 1H), 4.53 (p, J=6.9 Hz, 1H), 3.33 (s, 2H), 2.45-2.34 (m, 2H), 2.14 (s, 3H), 2.13-2.05 (m, 2H), 1.88-1.75 (m, 1H), 1.70-1.53 (m, 1H).

According to route (A), a reaction mixture of 2,8-dichloroquinoline (297 mg, 1.5 mmol, 1 eq.), 4-cyclobutoxy-2-methylaniline (266 mg, 1.5 mmol, 1 eq.), Pd(OAc)₂ (14 mg, 0.06 mmol, 4 mol %), XantPhos (34 mg, 0.06 mmol, 4 mol %) and Cs₂CO₃ (1.4 g, 4.3 mmoles, 2.9 eq.) in t-BuOH (6 mL) was heated at 90° C. for 14 hours under an inert atmosphere of argon. Upon cooling to room temperature, the reaction mixture was concentrated under reduced pressure and the resulting residue was diluted with dichloromethane. The organic phase was then washed with water, dried over MgSO₄, filtered and concentrated under reduced pressure. The resulting residue was purified by column chromatography on silica gel to afford 8-chloro-N-(4-cyclobutoxy-2-methylphenyl)quinolin-2-amine (22) (248 mg, 49%).

$^1$H NMR (300 MHz, CDCl$_3$) δ 7.82 (d, J=8.6 Hz, 1H), 7.68 (dd, J=8.0, 1.2 Hz, 1H), 7.52 (dd, J=8.0, 1.2 Hz, 1H), 7.38 (d, J=8.6 Hz, 1H), 7.15 (t, J=7.8 Hz, 1H), 6.76 (d, J=2.8 Hz, 1H), 6.71 (s, 1H), 6.68 (t, J=7.8 Hz, 2H), 4.64 (p, J=7.0 Hz, 1H), 2.53-2.40 (m, 2H), 2.26 (s, 3H), 2.23-2.10 (m, 2H), 1.95-1.80 (m, 1H), 1.71 (tt, J=10.2, 5.2 Hz, 1H).

$^{13}$C NMR (75 MHZ, CDCl$_3$) δ 154.7, 153.4, 141.9, 135.9, 133.3, 127.8, 127.5, 127.3, 124.9, 124.2, 122.6, 119.8, 115.0, 110.7, 108.2, 69.2, 28.4, 16.1, 10.9

Example 6: Compound (38) in Table I

According to route (E), 2-fluorophenol (1.8 g, 16 mmoles, 1 eq.) was placed in N,N-dimethylformamide (50 mL) with K$_2$CO$_3$ (4.5 g, 32 mmoles, 2 eq.). Upon addition of 4-fluoro-2-methyl-1-nitrobenzene (2.5 g, 16 mmoles, 1 eq.), the reaction mixture was heated at 70° C. and stirred for 3 days under an inert atmosphere of argon. Upon cooling to room temperature, the reaction mixture was partitioned between ethyl acetate and water. Upon decantation, the organic phase was washed with a saturated aqueous solution of brine, dried over MgSO$_4$, filtered and concentrated under reduced pressure. The resulting residue was purified by column chromatography on silica gel to afford 4-(2-fluorophenoxy)-2-methyl-1-nitrobenzene (2.8 g, 70%).

$^1$H NMR (300 MHz, CDCl$_3$) δ 8.05 (d, J=8.7 Hz, 1H), 7.28-7.13 (m, 4H), 6.86-6.78 (m, 2H), 2.60 (s, 3H).

According to route (D), 4-(2-fluorophenoxy)-2-methyl-1-nitrobenzene (2.8 g, 11.3 mmoles, 1 eq.) and tin (II) chloride dihydrate (7.7 g, 34.0 mmoles, 3 eq.) were placed in EtOH (91 mL). The reaction mixture was heated at 60° C. and stirred for 20 hours under an inert atmosphere of argon. The reaction mixture was then concentrated under reduced pressure and the resulting residue was diluted with ethyl acetate. The organic phase was washed with a IN NaOH aqueous solution then with a saturated aqueous solution of brine, dried over MgSO$_4$, filtered and concentrated under reduced pressure. The resulting residue was purified by column chromatography on silica gel to afford 4-(2-fluorophenoxy)-2-methylaniline (1.5 g, 61%).

$^1$H NMR (300 MHz, CDCl$_3$) δ 7.17-7.10 (m, 1H), 7.02-6.97 (m, 2H), 6.93-6.87 (m, 1H), 6.78 (d, J=2.7 Hz, 1H), 6.74 (dd, J=8.5, 2.7 Hz, 1H), 6.64 (d, J=8.5 Hz, 1H), 3.50 (br s, 2H), 2.15 (s, 3H).

According to route (A), a reaction mixture of 2-chloroquinoline (527 mg, 3.22 mmol, 1 eq.), 4-(2-fluorophenoxy)-2-methylaniline (700 mg, 3.22 mmol, 1 eq.), Pd(OAc)$_2$ (15 mg, 0.06 mmol, 2 mol %), XantPhos (37 mg, 0.06 mmol, 2 mol %) and Cs$_2$CO$_3$ (2.9 g, 9.0 mmoles, 2.8 eq.) in t-BuOH (13 mL) was heated at 90° C. for 16 hours under an inert atmosphere of argon. Upon cooling to room temperature, the reaction mixture was concentrated under reduced pressure and the resulting residue was diluted with dichloromethane. The organic phase was then washed with water, dried over MgSO$_4$, filtered and concentrated under reduced pressure. The resulting residue was purified by column chromatography on silica gel to afford N-[4-(2-fluorophenoxy)-2-methylphenyl]quinolin-2-amine (38) (385 mg, 35%).

$^1$H NMR (300 MHz, CDCl$_3$) δ 7.88 (d, J=8.9 Hz, 1H), 7.69 (d, J=8.2 Hz, 1H), 7.63 (d, J=8.2 Hz, 1H), 7.60-7.53 (m, 1H), 7.49 (d, J=8.6 Hz, 1H), 7.30-7.06 (m, 4H), 6.93 (d, J=2.7 Hz, 1H), 6.86 (dd, J=8.6, 2.7 Hz, 1H), 6.75 (d, J=8.9 Hz, 1H), 6.59 (s, 1H), 2.27 (s, 3H).

$^{13}$C NMR (75 MHZ, CDCl$_3$) δ 153.5, 152.2, 145.4, 141.5, 141.4, 135.5, 132.5, 130.8, 127.4, 125.1, 123.9, 123.7, 122.4, 122.3, 122.2, 121.5, 120.3, 119.3, 117.2, 114.8, 114.5, 113.2, 107.8, 15.9

[M+H]$^+$=345.2.

Example 7: Compound (46) in Table I

According to route (E), 2-fluorophenol (1.8 g, 16 mmoles, 1 eq.) was placed in N,N-dimethylformamide (50 mL) with K$_2$CO$_3$ (4.5 g, 32 mmoles, 2 eq.). Upon addition of 2-bromo-4-fluoro-1-nitrobenzene (3.5 g, 16 mmoles, 1 eq.), the reaction mixture was heated at 70° C. and stirred for 16 hours under an inert atmosphere of argon. Upon cooling to room temperature, the reaction mixture was partitioned between ethyl acetate and water. Upon decantation, the organic phase was washed with a saturated aqueous solution of brine, dried over MgSO$_4$, filtered and concentrated under reduced pressure. The resulting residue was purified by column chromatography on silica gel to afford 2-bromo-4-(2-fluorophenoxy)-1-nitrobenzene (3.8 g, 77%).

$^1$H NMR (300 MHz, CDCl$_3$) δ 7.95 (d, J=9.1 Hz, 1H), 7.30-7.15 (m, 5H), 6.95 (dd, J=9.1, 2.6 Hz, 1H).

According to route (C), 2-bromo-4-(2-fluorophenoxy)-1-nitrobenzene (1.0 g, 3.2 mmoles, 1 eq.) was placed in 1,4-dioxane (12 mL) with Pd(dppf)Cl$_2$·CH$_2$Cl$_2$ (262 mg, 0.1 mmole, 0.1 eq.). Upon addition of K$_3$PO$_4$ (2.7 g, 12.8 mmoles, 4 eq.) and cyclopropylboronic acid (826 mg, 9.6 mmoles, 3 eq.), the reaction mixture was heated at 100° C. and stirred for 20 hours under an inert atmosphere of argon. The reaction mixture was then concentrated under reduced pressure and the resulting residue was purified by column chromatography on silica gel to afford 2-cyclopropyl-4-(2-fluorophenoxy)-1-nitrobenzene (830 mg, 95%).

$^1$H NMR (300 MHz, CDCl$_3$) δ 7.90 (d, J=9.6 Hz, 1H), 7.26-7.11 (m, 4H), 6.74-6.69 (m, 2H), 2.56-2.47 (m, 1H), 1.11-1.01 (m, 2H), 0.73-0.61 (m, 2H).

According to route (D), 2-cyclopropyl-4-(2-fluorophenoxy)-1-nitrobenzene (830 mg, 3.0 mmoles, 1 eq.) and tin (II) chloride dihydrate (3.4 g, 15.2 mmoles, 5 eq.) were placed in EtOH (30 mL). The reaction mixture was heated at 60° C. and stirred for 14 hours under an inert atmosphere of argon. The reaction mixture was then concentrated under reduced pressure and the resulting residue was diluted with ethyl acetate. The organic phase was washed with a IN NaOH aqueous solution then with a saturated aqueous solution of brine, dried over MgSO$_4$, filtered and concentrated under reduced pressure to afford 2-cyclopropyl-4-(2-fluorophenoxy)aniline (736 mg, 100%).

$^1$H NMR (300 MHZ, CDCl$_3$) δ 7.18-7.10 (m, 1H), 7.03-6.95 (m, 2H), 6.91-6.84 (m, 1H), 6.78-6.71 (m, 2H), 6.64 (d, J=8.4 Hz, 1H), 3.85 (br s, 2H), 1.74-1.63 (m, 1H), 0.93-0.87 (m, 2H), 0.61-0.55 (m, 2H).

According to route (A), a reaction mixture of 2-chloroquinoline (164 mg, 1.0 mmol, 1 eq.), 2-cyclopropyl-4-(2-fluorophenoxy)aniline (243 mg, 1.0 mmol, 1 eq.), Pd(OAc)$_2$ (9 mg, 0.04 mmol, 4 mol %), XantPhos (23 mg, 0.04 mmol, 4 mol %) and Cs$_2$CO$_3$ (933 mg, 2.9 mmoles, 2.9 eq.) in t-BuOH (4 mL) was heated at 90° C. for 14 hours under an inert atmosphere of argon. Upon cooling to room temperature, the reaction mixture was concentrated under reduced pressure and the resulting residue was diluted with dichloromethane. The organic phase was then washed with water, dried over MgSO$_4$, filtered and concentrated under reduced pressure. The resulting residue was purified by column chromatography on silica gel to afford N-[2-cyclopropyl-4-(2-fluorophenoxy)phenyl]quinolin-2-amine (46) (121 mg, 33%).

$^1$H NMR (300 MHz, CDCl$_3$) δ 7.88 (d, J=8.9 Hz, 1H), 7.80 (d, J=8.7 Hz, 1H), 7.73 (d, J=8.2 Hz, 1H), 7.62 (d, J=8.2 Hz, 1H), 7.59-7.54 (m, 1H), 7.29-7.24 (m, 1H), 7.21-7.15 (m, 1H), 7.12-7.00 (m, 2H), 6.88-6.81 (m, 2H), 6.77 (d, J=2.8 Hz, 1H), 1.95 (tt, J=8.4, 5.4 Hz, 1H), 1.01-0.85 (m, 2H), 0.69-0.60 (m, 2H).

$^{13}$C NMR (75 MHZ, CDCl$_3$) δ 155.8, 155.4, 153.7, 147.8, 144.5, 144.4, 144.3, 137.8, 137.6, 134.8, 129.9, 127.5, 126.5, 124.7, 124.6, 124.5, 124.4, 124.1, 124.0, 122.9, 121.2, 117.2, 116.9, 116.5, 115.6, 111.2, 100.0, 80.3, 11.7, 7.2

[M+H]$^+$=371.2

Pharmacological Data

Example 8: Chikungunya Virus

The compounds of the invention have been the subject of pharmacological tests which have demonstrated their relevance as active substances in therapy and in particular for preventing, inhibiting or treating Chikungunya virus infection.

Material and Methods

Inhibition of Chikungunya Virus (CHIKV) Production in Infected HEK293T Cell Line.

The ability of the compounds to inhibit viral replication was assessed with an experiment in which infected cells were treated by compounds of formula (I) at 1 μM. As a positive control for inhibition of Chikungunya, Ribavirin was used. Toxicity of the compounds was assessed in parallel.

· Amplification of Cells

Human embryonic kidney cells 293T (HEK293T, CRL-11268) were maintained in Dulbecco's modified Eagle's Medium (DMEM, 31966-021, Thermo Fisher Scientific) supplemented with 10% of fetal bovine serum (FBS), penicillin and streptomycin. After removal of the medium, cells were washed with a Ca$^{2+}$- and Mg$^{2+}$-free salt solution to remove all traces of serum. After aspiration of wash solution, cells were dissociated with 0.25% Trypsin-EDTA solution and incubated 30 s at least in 37° ° C. incubator. Concentration of cell suspension was determined by an automatic cell counter (EVE, NanoEntek) and, if needed, adjusted to 0.33×10$^6$ cells/mL with DMEM medium supplemented with 10% FBS.

• Preparation of the Compounds

100 μL of the cell suspension were dispatched in a ViewPlate-96 Black (6005182, PerkinElmer) and in a transparent 96-well cell culture plate (655180, Greiner bio-one). After an incubation for 24 h at 37° C. under 5% of CO$_2$, compounds were added at the proper concentration.

• Screen at 1 μM

An intermediate dilution was prepared with DMSO (D8418, Sigma) at 2 mM in a 96-well V-bottom microplate from the stock solution:

Mix 1 μL of the 50 mM stock library in 25 μL of DMSO.
Mix 2 μL of the 25 mM stock library in 25 μL of DMSO.

• Determination of IC$_{50}$ Values

An intermediate dilution was prepared with DMSO (D8418, Sigma) at 25 mM in a 96-well V-bottom microplate from the stock solution:

Mix 2 μL of the 50 mM stock library in 2 μL of DMSO.

Serial dilutions were performed in 2 μL of DMSO 13 times to reach 0.0015 mM as follows in table III:

TABLE III

| | Concentration (mM) | Volume of DMSO 100% (μL) | Volume of solution |
|---|---|---|---|
| A | 12.5 | 2 | 2 μL of 50 mM solution |
| B | 6.25 | 2 | 2 μL of solution A |
| C | 3.125 | 2 | 2 μL of solution B |
| D | 1.56 | 2 | 2 μL of solution C |
| E | 0.78 | 2 | 2 μL of solution D |
| F | 0.39 | 2 | 2 μL of solution E |
| G | 0.195 | 2 | 2 μL of solution F |
| H | 0.0976 | 2 | 2 μL of solution G |
| I | 0.0488 | 2 | 2 μL of solution H |
| J | 0.0244 | 2 | 2 μL of solution I |
| K | 0.0122 | 2 | 2 μL of solution J |
| L | 0.0061 | 2 | 2 μL of solution K |
| M | 0.0030 | 2 | 2 μL of solution L |
| N | 0.0015 | 2 | 2 μL of solution M |

For both screen and determination of IC$_{50}$ 1 μL of each solution was added in a 1 mL Masterblock 96 wells (Greiner bio-one, 780261) containing 1 mL of DMEM medium. As a positive control, 5 μL of a 80 mM Ribavirin solution (R9644, Sigma) is added to 1 mL of DMEM. On the other hand, DMSO is used as a negative control.

• Infection

Cells were infected with 30 μL of CHIKV strain of La Réunion outbreak (LR2006-OPY1) with GFP modification in 5' (CHIK 5'LR) (Tsetsarkin K, Higgs S, McGee C E, De Lamballerie X, Charrel R N, Vanlandingham D L. Infectious Clones of Chikungunya Virus (La Réunion Isolate—Ref-SKU: 001N-EVA249 (PMID: 17187566) available at the following address: https://www.european-virus-archive-.com/nucleic-acid/chikv-lr-5gfp-infectious-clone) for Vector Competence Studies. Vector Borne Zoonotic Dis. 2006; 6(4)). This modified virus was used to infect cells at MOI 0.1. The LR2006-OPY1 strain of CHIKV (CHIKV-LR) was obtained from the World Reference Center for Arboviruses at the University of Texas Medical Branch, Galveston, TX. This strain was originally isolated from the serum of a febrile French patient returning from La Réunion Island.

• Cell Lysis

Medium was removed after 22 h at 37° ° C. under 5% of CO$_2$ and cells were washed as described above. 60 μL of RIPA buffer (50 mM Tris-HCl pH8, 100 mM NaCl, 1 mM MgCl$_2$, 1% Triton X-100) was added to cells and incubated for at least 20 min before reading fluorescence signal. Pierce 660 nm Protein Assay Reagent (22660, Thermo scientific) was used to normalize fluorescence signal by protein quantity.

CellTiter 96® AQueous One Solution Cell Proliferation Assay (MTS) (G3581, Promega) was used to check the toxicity of the compounds. We added 20 μL of MTS solution and read absorbance at 492 nm one hour later.

Results

A first round of experiments has been performed wherein the results are expressed as inhibition percentage, which is calculated as follows, through the following steps:

1. Fluorescence intensity (FI) 509 nm/Absorbance 660 nm (A660)=A

This ratio allows considering the infection (GFP virus) to the protein amount.

2. A'=A—background noise of non-infected plate,

3. B=Fluorescence intensity (FI)/Absorbance 660 nm (A660) of infected but non treated plates, 4. C=A'/B which is then converted as the percentage of infection after treatment, compared to non-treated sample, and subsequently as the infection percentage. For instance, a value of 100 in Table IV here below means that, after treatment, the signal attributed to GFP fluorescence is abolished, which is correlated to the absence of infection.

5. C'=100−C

This value corresponds to the inhibition's percentage.

The following Table IV encompasses said C' value for some compounds as calculated above with a mean of 2 experiments, and the corresponding standard deviation.

Some values were originally above 100. In these cases, the value has been lowered to 100. This means that some molecules also have an impact on the viability of the cells. In other words, the A value may be lower than the background noise.

Moreover, for each measure, the test was performed with Ribavirin as control. The value of the inhibition percentage was checked, giving 100%.

TABLE IV

| | % CHIKV Inhibition | |
|---|---|---|
| Ex | Mean (n = 2) | Standard deviation (n = 2) |
| 1 | 97 | 4 |
| 2 | 100 | 0 |
| 3 | 100 | 0 |
| 4 | 100 | 0 |
| 6 | 100 | 0 |
| 7 | 99 | 2 |
| 8 | 100 | 0 |
| 10 | 100 | 0 |
| 12 | 95 | 5 |
| 13 | 100 | 1 |
| 14 | 91 | 12 |
| 16 | 98 | 2 |
| 17 | 100 | 0 |
| 20 | 99 | 1 |
| 21 | 100 | 0 |
| 22 | 100 | 0 |
| 23 | 82 | 23 |
| 29 | 97 | 4 |
| 31 | 93 | 10 |
| 32 | 90 | 10 |
| 38 | 98 | 1 |
| 39 | 99 | 2 |

A second round of experiments has been performed giving the results as $IC_{50}$ values.

The $IC_{50}$ values range between 0.1 nM and 1 μM, in particular between 0.5 and 500 nM and even more particularly between 1 and 400 nM, for example between 1 and 200 nM. For example, compounds 2, 4, 6, 10, 13, 16, 17, 20, 21, 22, 38, 39, 40, 41, 42, 43, 44, 45 and 46, have an $IC_{50}$ value ranging between 1 and 200 nM.

Conclusion

Based on the previous results, it can be concluded that the compounds of formula (I) are suitable chemical compounds for treating and/or preventing RNA virus infections caused by RNA viruses of group IV, more particularly, *Alphavirus* infections, and most particularly Chikungunya virus infections.

Example 9: RSV Virus

The compounds of the invention have been the subject of pharmacological tests which have demonstrated their relevance as active substances in therapy and in particular for preventing, inhibiting or treating RSV virus infection.

Material and Methods

Protocol for Screening Antiviral Compounds for RSV Inhibition and Cytotoxicity Using Viral ToxGlo Assay HEp-2 cells were maintained in Eagle's minimum essential medium (EMEM) with Earle's BSS adjusted to contain 2 mM L-glutamine, 10% fetal bovine serum, 100 U/ml penicillin and 100 μg/ml streptomycin. For the purposes of the screening assay they were grown to 90% confluency, trypsinized and recovered. The trypsin was neutralised with cell culture media and cells were centrifuged at 150×g for 5 minutes before discarding the supernatant and resuspending cell pellet in assay media (EMEM with Earle's BSS adjusted to contain 2 mM L-glutamine, 2% fetal bovine serum and 100 U/ml penicillin and 100 μg/ml streptomycin). The cells were seeded into white clear-bottomed cell culture plates at a density of $1.5 \times 10^4$ cells/well in 50 μl and $4 \times 10^3$ cells/well in 25 μl for 96 well plates and 384 well plates respectively. For the media/background control column assay media only was added. Cell plates were placed in a humid chamber and incubated overnight at 37° C./5% $CO_2$. After overnight incubation cells were checked for confluency and healthy appearance.

Test articles were made up at 10× test concentration in a maximum DMSO concentration of 10% (final assay concentration maximal 1% DMSO) and added to the cell plates in volumes of 10 μl for 96 well plates and 5 μl for 384 well plates. For cell control and virus control wells the test article solvent only was added. Virus or assay media for cytotoxicity test wells and media/cell control wells was added immediately after test articles at an MOI of 0.5, 40 or 20 μl for 96 and 384 well plates respectively. Virus suspension was prepared by thawing RSV A2 frozen stocks and diluting to the required concentration of plaque forming units in assay media on ice.

Cell plates were further incubated inside a humid chamber for 72 h p.i at 37° C./5% $CO_2$. After the incubation period cells were observed under the microscope to check for characteristic cytopathic effect in virus control wells and healthy cells in the cell control wells. After plates were adjusted to room temperature 20/40 μl Viral ToxGlo (Promega) was added to each well of the 384/96 well cell plates. Plates were incubated at room temperature, protected from light on a plate rocker for 20 minutes before measuring the luminescence on a spectrophotometer (Biotek Synergy HTX).

RSV inhibition was calculated as percentage of cytopathic effect inhibition relative to the virus control and cytotoxicity as percentage of cell survival relative to cell control wells. This allowed $EC_{50}$ values to be calculated for each test article where a virus inhibition or cytotoxic dose response was identified. $EC_{50}$ values ranging between 0.001 UM and 5 μM could thus be determined for compounds 1, 6, 10, 13, 28, 38, 43, 47, 48, 49, 50, 51, 52, 53, 54, 55, 56 and 57.

TABLE V

| Ex | $EC_{50}$ (nM) |
|---|---|
| 1 | 3311 |
| 6 | 1212 |
| 10 | 585 |
| 13 | 1175 |

TABLE V-continued

| Ex | EC$_{50}$ (nM) |
|---|---|
| 28 | 1785 |
| 38 | 200 |
| 43 | 348 |
| 47 | 420 |
| 48 | 360 |
| 49 | 513 |
| 50 | 283 |
| 51 | 412 |
| 52 | 344 |
| 53 | 196 |
| 54 | 94 |
| 55 | 192 |
| 56 | 132 |
| 57 | 473 |

Conclusion

Based on the previous results, it can be concluded that the compounds of formula (I) are suitable chemical compounds for treating and/or preventing RNA virus infections caused by RNA viruses of group V, more particularly, pneumovirus infections, and most particularly RSV virus infections.

Example 10: Dengue 2 Virus

The compounds of the invention have been the subject of pharmacological tests which have demonstrated their relevance as active substances in therapy and in particular for preventing, inhibiting or treating Dengue 2 virus infection.

Material and Methods

Protocol for Screening Antiviral Compounds for DENV-2 Inhibition and Cytotoxicity Using Viral ToxGlo Assay A549 cells were maintained in Dulbecco's Modified Eagle Medium (DMEM) supplemented with 10% fetal bovine serum, 100 U/ml penicillin and 100 µg/ml streptomycin. For the purposes of the screening assay they were grown to 90% confluency, trypsinized and recovered. The trypsin was neutralised with cell culture media and cells were centrifuged at 150×g for 5 minutes before discarding the supernatant and resuspending cell pellet in assay media (DMEM supplemented with 2% fetal bovine serum and 100 U/ml penicillin and 100 µg/ml streptomycin). The cells were seeded into 96-well white clear-bottomed cell culture plates at a density of 1.0×10$^4$ cells/well in 50 µl. For the media/background control column assay media only was added. Cell plates were placed in a humid chamber and incubated overnight at 37° C./5% CO$_2$. After overnight incubation cells were checked for confluency and healthy appearance.

Test compounds were prepared at a final concentration of 10 µM, in a maximum DMSO concentration of 1% (final assay concentration maximal 0.1% DMSO) and added to the cell plates in volumes of 10 µl. For cell control and virus control wells the test article solvent only was added. As a positive inhibition control, 7-Deaza-2'-C-methyladenosine was added at 100 µM in 3 wells. Virus (DENV-2 strain 16681) or assay media for cytotoxicity test wells and media/cell control wells was added immediately after test articles at an MOI of 0.5, 40 for 96 well plates respectively. Virus suspension was prepared by thawing DENV-2 frozen stocks and diluting to the required concentration of plaque forming units in assay media.

Cell plates were further incubated inside a humid chamber for 5 days p.i at 37° C./5% CO$_2$. After the incubation period cells were observed under the microscope to check for characteristic cytopathic effect in virus control wells and healthy cells in the cell control wells. After plates were adjusted to room temperature 20 µl Viral ToxGlo (Promega) was added to each well of the 96-well cell plates. Plates were incubated at room temperature for 5 minutes before measuring the luminescence on a spectrophotometer (Envision, PerkinElmer).

DENV-2 inhibition was calculated as percentage of cytopathic effect inhibition relative to the virus control and cytotoxicity as percentage of cell survival relative to cell control wells.

TABLE VI

| Ex | % DENV-2 Inhibition Mean (n = 3) |
|---|---|
| 5 | 156 |
| 10 | 79 |
| 12 | 129 |
| 13 | 117 |
| 16 | 77 |
| 20 | 94 |
| 22 | 82 |
| 39 | 104 |
| 40 | 97 |
| 42 | 84 |
| 43 | 68 |
| 44 | 94 |
| 46 | 104 |
| 47 | 82 |
| 54 | 69 |
| 56 | 76 |
| 63 | 74 |
| 76 | 78 |
| 77 | 87 |

Conclusion

Based on the previous results, it can be concluded that the compounds of formula (I) are suitable chemical compounds for treating and/or preventing RNA virus infections caused by RNA viruses of group IV, more particularly, *Flavivirus* infections, and most particularly Dengue 2 virus infections.

The present invention further relates to a pharmaceutical composition comprising at least one new compound as defined above or any of its pharmaceutically acceptable salts, or at least any of compounds (2) to (26) and (28) to (79) as defined above or in claim 3, more preferably compounds 2 to 8, 10, 12 to 14, 16, 17, 20 to 23, 28, 29, 31, 32, and 38 to 57, 63, 76 and 77, or any of its pharmaceutically acceptable salts, and also at least one pharmaceutically acceptable excipient.

Pharmaceutical compositions of the invention can contain one or more compound(s) of the invention in any form described herein.

Still a further object of the present invention consists of the use of at least one compound of formula (I), as defined above, or of at least any of compounds (1) to (79) as defined above, more preferably compounds 2 to 8, 10, 12 to 14, 16, 17, 20 to 23, 28, 29, 31, 32, and 38 to 57, 63, 76 and 77, or one of their pharmaceutically acceptable salts according to the present invention for preparing a drug to prevent or treat, in a patient, a RNA virus infection, and most preferably a RNA virus infection caused by a RNA virus from group IV or Group V according to the Baltimore classification, and for example a Chikungunya infection, a Dengue infection, an Influenza infection or a RSV infection.

Therefore, the present invention relates to one compound of formula (I), as defined above, and compounds (1) to (79), more preferably compounds 1 to 8, 10, 12 to 14, 16, 17, 20 to 23, 28, 29, 31, 32, and 38 to 57, 63, 76 and 77, or one of their acceptable salts as an agent for inhibiting, preventing or treating a RNA virus infection, and most preferably a RNA virus infection from group IV or V, and for example a Chikungunya infection, a Dengue infection, an Influenza infection or a RSV infection.

According to a particular embodiment, the treatment is continuous or non-continuous.

A "continuous treatment" means a long-term treatment which can be implemented with various administration frequencies, such as once every day, every three days, once a week, or once every two weeks or once every month.

According to one embodiment, the compound of formula (I), or any of its pharmaceutically acceptable salts, is administered at a dose varying from 0.1 to 1000 mg, in particular varying from 0.1 to 10 mg, or for example varying from 10 to 200 mg, or for example varying from 200 to 1000 mg.

Another object of the invention relates to a therapeutic method for treating and/or preventing a patient from a RNA virus infection, more preferably a RNA virus infection from group IV or V, still more preferably a Chikungunya infection, a Dengue infection, an Influenza infection or a RSV infection, and even more preferably a RSV viral infection comprising the administration of a therapeutically effective amount of a compound of formula (I), or of compounds (1) to (79), as defined above, or one of their acceptable salts.

In a specific embodiment, the invention provides a use of a compound of formula (I) according to the invention or a pharmaceutically acceptable salt thereof or a pharmaceutically active derivative thereof or a method according to the invention wherein the compound of formula (I) is to be administered in combination with a co-agent useful in the treatment of said RNA virus infection, more preferably said RNA virus infection from group IV or V, and for example Chikungunya infection, Dengue infection, Influenza infection or RSV infection, in particular RSV infection.

The compounds can be administered through any mode of administration such as, for example, intramuscular, intravenous, intranasal or oral route, etc.

Compounds of the present invention may, in appropriate cases, be administered as prodrugs, such as esters, of compounds with which the invention is concerned. "Prodrug" means a compound which is convertible in vivo by metabolic means (e.g. by hydrolysis, reduction or oxidation) to a compound of the present invention. For example, an ester prodrug of a compound of the present invention may be convertible by hydrolysis in vivo to the parent molecule. Suitable esters of compounds of the present invention are for example acetates, citrates, lactates, tartrates, malonates, oxalates, salicylates, propionates, succinates, fumarates, maleates, methylene-bis-ß-hydroxynaphthoates, gentisates, isethionates, di-p-toluoyltartrates, methanesulphonates, ethanesulphonates, benzenesulphonates, p-toluenesulphonates, cyclohexylsulfamates and quinates. Examples of ester prodrugs are those described by F. J. Leinweber, Drug Metab. Res., 1987, 18, 379. As used herein, references to the compounds of the present invention are meant to also include any prodrug or metabolite form.

The inventive composition can further include one or more additives such as diluents, excipients, stabilizers and preservatives. Such additives are well known to those skilled in the art and are described notably in "*Ullmann's Encyclopedia of Industrial Chemistry, 6th Ed.*" (various editors, 1989-1998, Marcel Dekker) and in "*Pharmaceutical Dosage Forms and Drug Delivery Systems*" (ANSEL et al., 1994, WILLIAMS & WILKINS).

The aforementioned excipients are selected according to the dosage form and the desired mode of administration.

According to an embodiment, compositions of this invention may be administered in any manner, including, but not limited to, orally, parenterally, sublingually, transdermally, vaginally, rectally, transmucosally, topically, intranasally via inhalation, via buccal or intranasal administration, or combinations thereof. Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v. infusion.

For example, a compound of formula (I) can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

In a particular embodiment, a compound of formula (I) according to the invention is administered orally.

Oral route of administration is in particular preferred in the prophylaxis or treatment aspect of the invention.

According to another embodiment, pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

The invention claimed is:

1. A method for treating a patient with a RNA virus infection caused by a RNA virus belonging to group IV or V of the Baltimore classification, the RNA virus infection caused by a RNA virus belonging to a group IV or V of the Baltimore classification being chosen among a RSV viral infection, a Chikungunya viral infection, a Dengue viral infection, and an Influenza viral infection, the method comprising:

administering a therapeutically effective amount of a compound of formula (I) or a pharmaceutically acceptable salt thereof to the patient

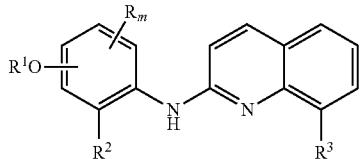

(I)

wherein
m is 0, 1 or 2,
$R^3$ represents a chlorine atom or a hydrogen atom,
R represents a $(C_1-C_4)$alkyl group, a $(C_3-C_6)$cycloalkyl group, a halogen atom, a $(C_1-C_5)$alkoxy group, a $-SO_2-NR_aR_b$ group, a $-SO_3H$ group, a $-OH$ group, a $-O-SO_2-OR_c$ group or a $-O-P(=O)-(OR_c)(OR_d)$ group,
$R^1$ represents
(i) a $CF_3$ group,
(ii) a $(C_1-C_{10})$alkyl group, one carbon atom of the $(C_1-C_{10})$alkyl group being optionally replaced by an oxygen atom and the $(C_1-C_{10})$alkyl group being optionally substituted by one or more of a $-CF_3$ group, halogen atom, pyridyl group, phenyl group, $(C_3-C_6)$cycloalkyl group, $(C_3-C_6)$heterocycloalkyl group or hydroxy group,
(iii) a $(C_3-C_6)$cycloalkyl group or a $(C_3-C_6)$heterocycloalkyl group, each of which is optionally substituted by one or two group(s) independently selected from a $(C_1-C_2)$alkyl group or a fluorine atom, or
(iv) a phenyl group or a naphthyl group, each of which is optionally substituted by one or two group(s) independently selected from a $(C_1-C_4)$ alkyl group, a halogen atom, a $-COOR'$ group, a $(C_1-C_5)$alkoxy group, a $-SO_2-NR_aR_b$ group, a $-SO_3H$ group, a $-OH$ group, a $-O-SO_2-OR_c$ group or a $-O-P(=O)-(OR_c)(OR_d)$ group,
$R^2$ represents a $(C_1-C_{10})$alkyl group, a $(C_3-C_6)$cycloalkyl or a $(C_3-C_6)$heterocycloalkyl group, the $(C_3-C_6)$cycloalkyl or $(C_3-C_6)$heterocycloalkyl groups being optionally substituted by one or two group(s) independently selected from a $(C_1-C_2)$alkyl group or a fluorine atom,
the $OR^1$ group is in para or meta position on the phenyl with respect to the $-NH-$ group,
$R'$, $R_a$ and $R_b$ independently represent a hydrogen atom, a $(C_1-C_5)$alkyl group or a $(C_3-C_6)$cycloalkyl group, and
$R_c$ and $R_d$ independently represent a hydrogen atom, Li, Na, K, $N(R_a)_4$ or a benzyl group.

2. The method according to claim 1, wherein m is 0 or 1.
3. The method according to claim 1, wherein R represents a $(C_1-C_4)$alkyl group or a $(C_3-C_6)$cycloalkyl group.
4. The method according to claim 1, wherein
$R^1$ represents
(i) a $CF_3$ group,
(ii) a $(C_1-C_{10})$alkyl group, one carbon atom of the $(C_1-C_{10})$alkyl group being optionally replaced by an oxygen atom and the $(C_1-C_{10})$alkyl group being optionally substituted by one or more of a $-CF_3$ group, pyridyl group, phenyl group, $(C_3-C_6)$heterocycloalkyl group or hydroxy group,
(iii) a $(C_3-C_6)$cycloalkyl group or a $(C_3-C_6)$heterocycloalkyl group, or
(iv) a phenyl group or a naphthyl group, each of which is optionally substituted by one or two group(s) independently selected from a $(C_1-C_4)$alkyl group, a halogen atom, a $-COOR'$ group, a $(C_1-C_5)$alkoxy group, or a $-OH$ group, $R'$ being a $(C_1-C_5)$alkyl group, and the $OR^1$ group being in para or meta position on the phenyl with respect to the $-NH-$ group.

5. The method according to claim 1, wherein $R^2$ represents a $(C_1-C_{10})$alkyl group, group or a $(C_3-C_6)$cycloalkyl group.

6. The method according to claim 1, wherein
m is 0 or 1 and R is a methyl group, and
$R^1$ represents
(i) a $CF_3$ group,
(ii) a $(C_1-C_6)$alkyl group, one carbon atom of the $(C_1-C_6)$alkyl group being optionally replaced by an oxygen atom and the $(C_1-C_6)$alkyl group being optionally substituted by a $-CF_3$ group, a pyridyl group, a phenyl group, a $(C_3-C_6)$heterocycloalkyl group or a hydroxy group, or
(iii) a $(C_3-C_6)$cycloalkyl group or a $(C_3-C_6)$heterocycloalkyl group,
(iv) a phenyl group or a naphthyl group, each of which is optionally substituted by one or two group(s) independently selected from a $(C_1-C_4)$alkyl group, a $-COOR'$ group, a $(C_1-C_4)$alkoxy group, a hydroxy group or a halogen atom,
$R^2$ represents a $(C_1-C_4)$alkyl group,
$R'$ represents a $(C_1-C_2)$alkyl group.

7. The method according to claim 1, wherein $R^2$ represents a $(C_1-C_{10})$alkyl group or a $(C_3-C_6)$cycloalkyl, the $(C_3-C_6)$cycloalkyl group being optionally substituted by one or two group(s) independently selected from a $(C_1-C_2)$alkyl group or a fluorine atom.

8. The method according to claim 1, wherein the compound of formula (I) is chosen among:

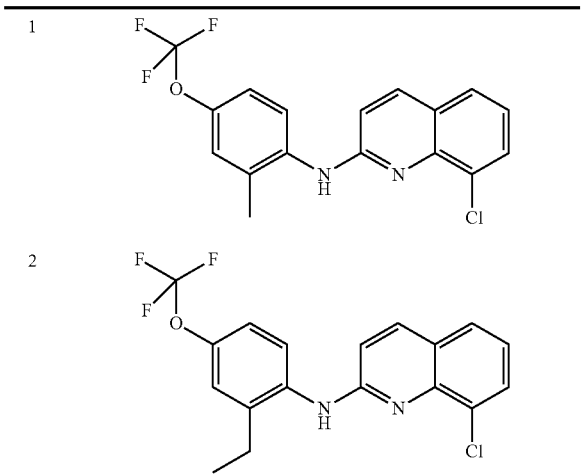

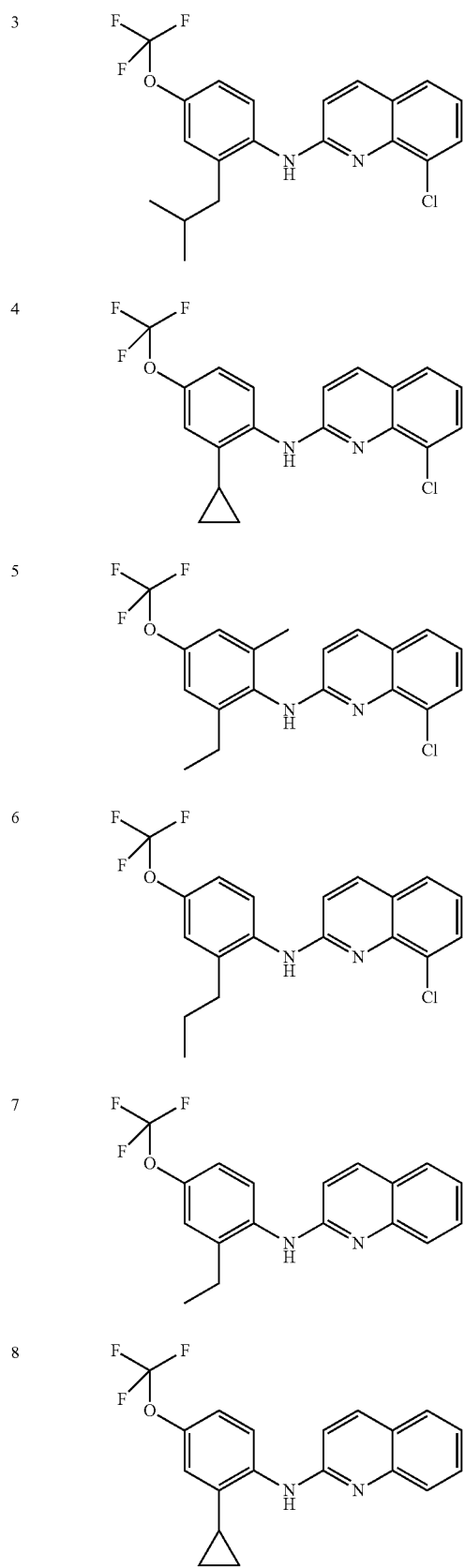
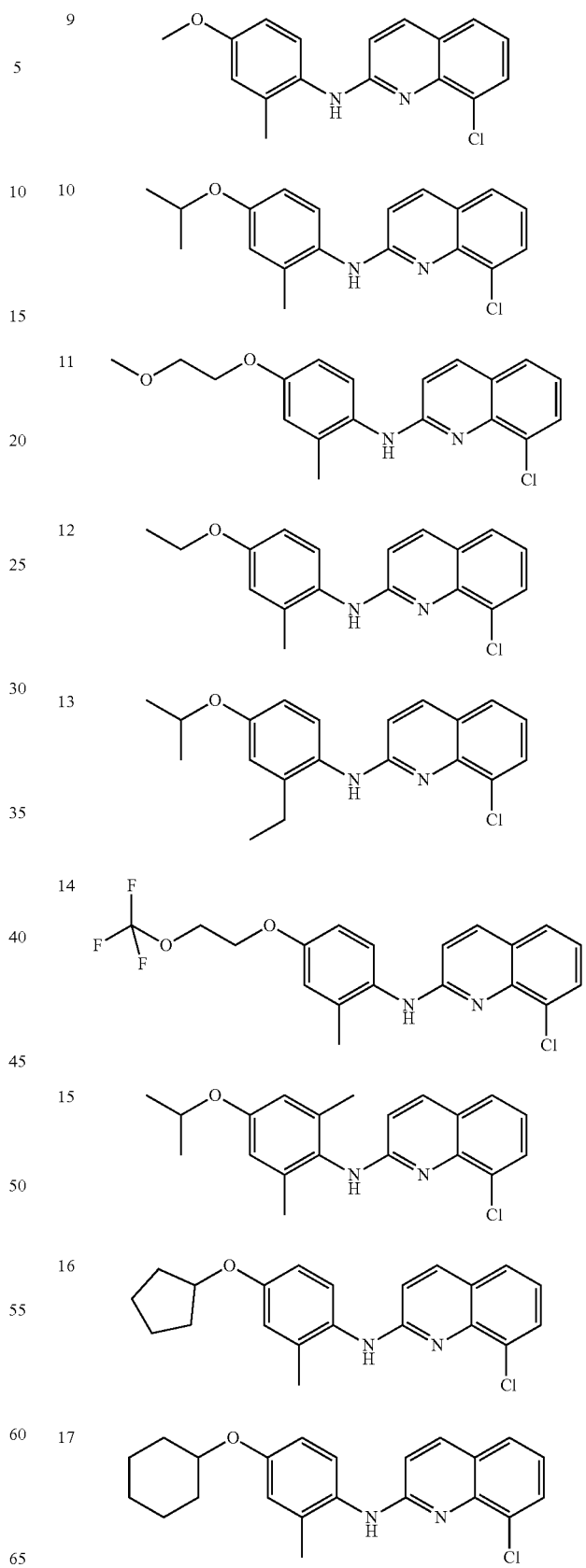

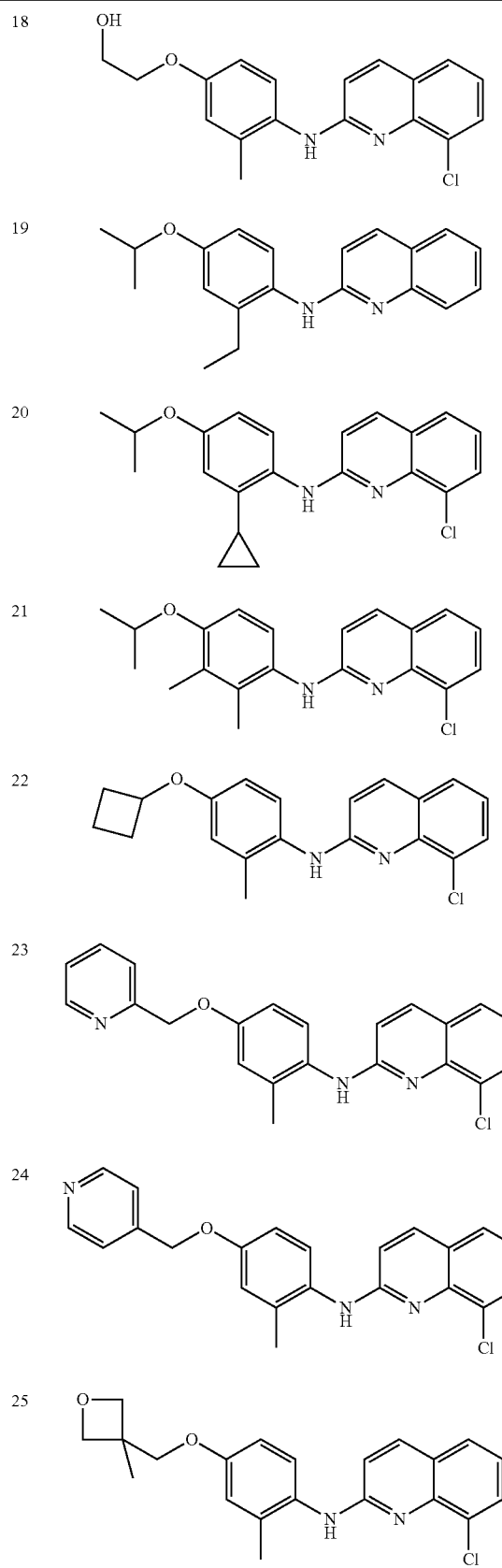
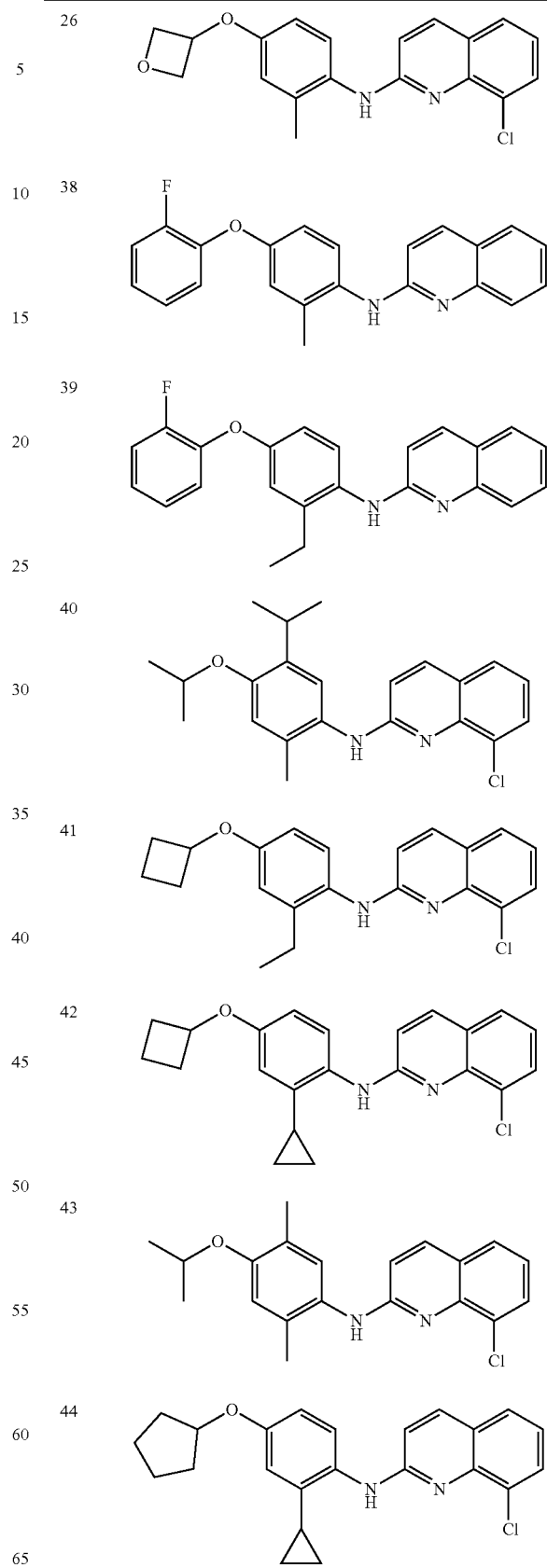

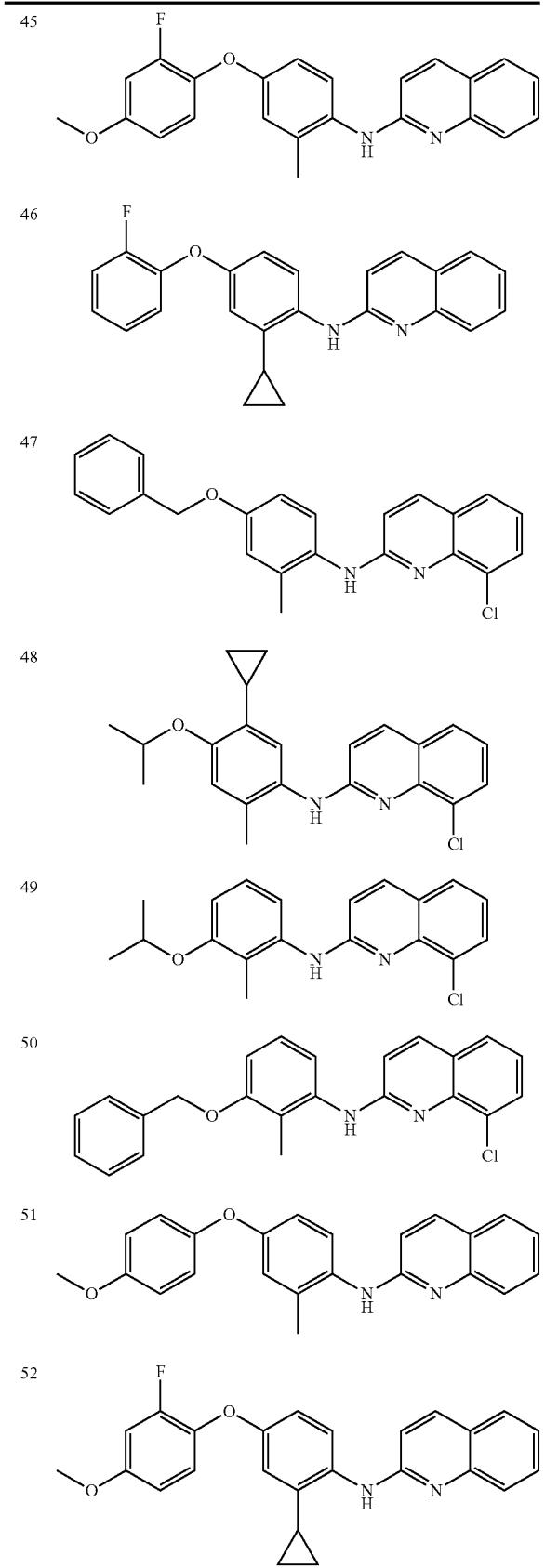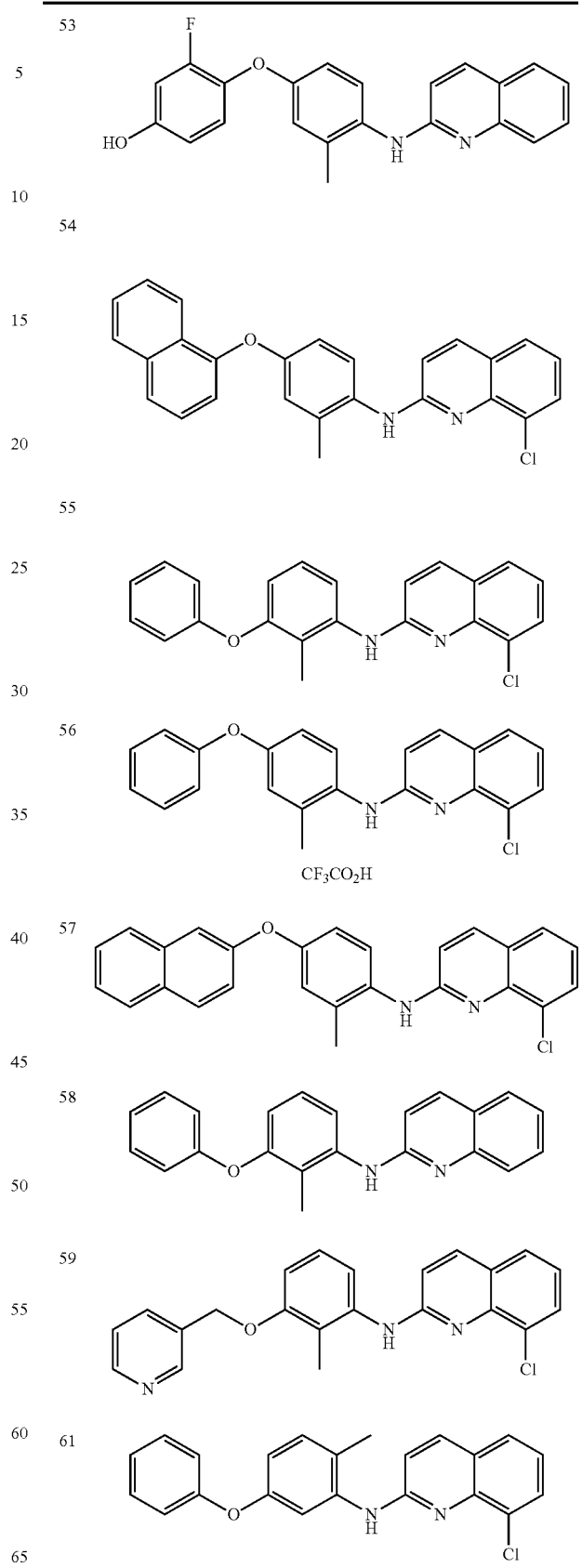

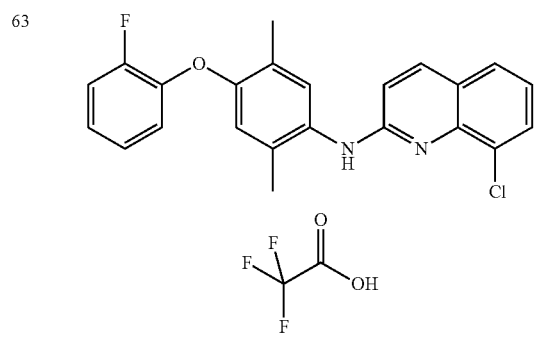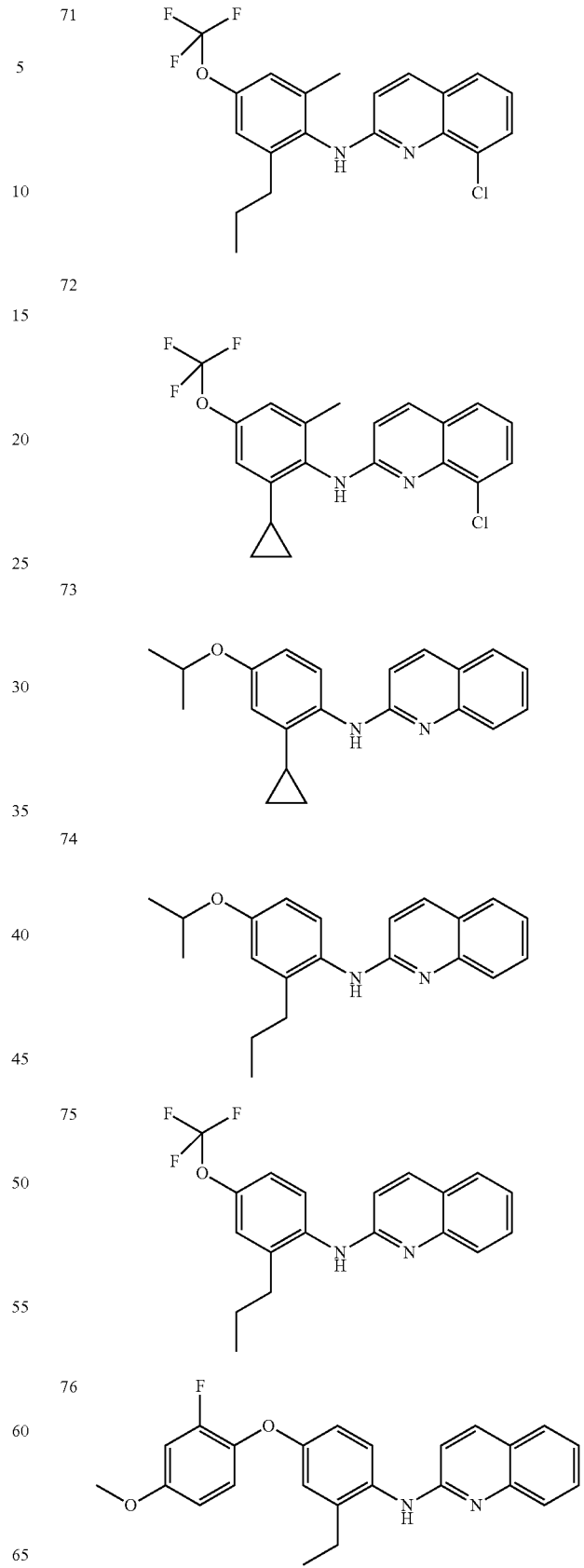

78

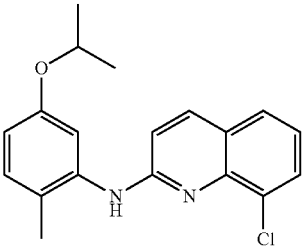 [SMILES: Cc1ccc(OC(C)C)cc1Nc1ccc2cccc(Cl)c2n1]

79

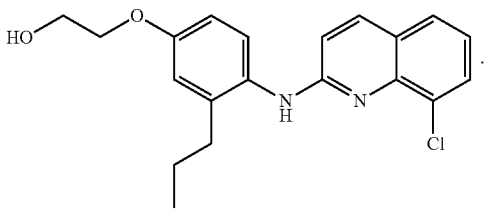 [SMILES: CCCc1cc(OCCO)ccc1Nc1ccc2cccc(Cl)c2n1]

9. The method according to claim 1, wherein the RNA virus infection caused by the RNA virus belonging to group IV or V of the Baltimore classification is chosen among a RSV viral infection, a Chikungunya viral infection and a Dengue viral infection.

10. A compound of formula (I) or a pharmaceutically acceptable salt thereof

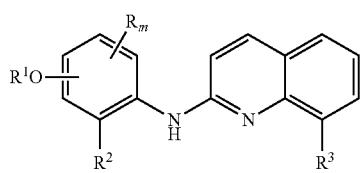

wherein m is 0, 1 or 2, $R^3$ represents a chlorine atom or a hydrogen atom,

R represents a $(C_1$-$C_4)$alkyl group, a $(C_3$-$C_6)$cycloalkyl group, a halogen atom, a $(C_1$-$C_5)$alkoxy group, a —$SO_2$—$NR_aR_b$ group, a —$SO_3H$ group, a —OH group, a —O—$SO_2$—$OR_c$ group or a —O—P(=O)—$(OR_c)(OR_d)$ group, $R^1$ represents
- (i) a $CF_3$ group,
- (ii) a $(C_1$-$C_{10})$alkyl group, one carbon atom of the $(C_1$-$C_{10})$alkyl group being optionally replaced by an oxygen atom and the $(C_1$-$C_{10})$alkyl group being optionally substituted by one or more of a —$CF_3$ group, halogen atom, pyridyl group, phenyl group, $(C_3$-$C_6)$cycloalkyl group, $(C_3$-$C_6)$heterocycloalkyl group or hydroxy group,
- (iii) a $(C_3$-$C_6)$cycloalkyl group or a $(C_3$-$C_6)$heterocycloalkyl group, each of which is optionally substituted by one or two group(s) independently selected from a $(C_1$-$C_2)$alkyl group or a fluorine atom, or
- (iv) a phenyl group or a naphthyl group, each of which is optionally substituted by one or two group(s) independently selected from a $(C_1$-$C_4)$alkyl group, a halogen atom, a —COOR' group, a $(C_1$-$C_5)$alkoxy group, a —$SO_2$—$NR_aR_b$ group, a —$SO_3H$ group, a —OH group, a —O—$SO_2$—$OR_c$ group or a —O—P(=O)—$(OR_c)(OR_d)$ group, $R^2$ represents a $(C_3$-$C_6)$cycloalkyl group or a $(C_3$-$C_6)$heterocycloalkyl group, each of which is optionally substituted by one or two group(s) independently selected from a $(C_1$-$C_2)$alkyl group or a fluorine atom, the $OR^1$ group is in para or meta position on the phenyl with respect to the —NH— group, R', $R_a$ and $R_b$ independently represent a $(C_1$-$C_5)$alkyl group or a $(C_3$-$C_6)$cycloalkyl group, and $R_c$ and $R_d$ independently represent a hydrogen atom, Li, Na, K, $N(R_a)_4$ or a benzyl group.

11. The compound of formula (I) or the pharmaceutically acceptable salt thereof according claim 10, wherein $R^1$ represents
- (i) a $CF_3$ group,
- (ii) a $(C_1$-$C_{10})$alkyl group, one carbon atom of the $(C_1$-$C_{10})$alkyl group being optionally replaced by an oxygen atom and the $(C_1$-$C_{10})$alkyl group being optionally substituted by one or more of a —$CF_3$ group, halogen atom, or
- (iii) a $(C_3$-$C_6)$cycloalkyl or a $(C_3$-$C_6)$heterocycloalkyl group, each of which is optionally substituted by one or two $(C_1$-$C_2)$alkyl group or fluorine atom.

12. A pharmaceutical composition comprising:
the compound of formula (I) according to claim 10 or the pharmaceutically acceptable salt thereof, and
at least one pharmaceutically acceptable excipient.

* * * * *